(12) United States Patent
Norman et al.

(10) Patent No.: US 8,680,289 B2
(45) Date of Patent: Mar. 25, 2014

(54) COMPLEXES OF IMIDAZOLE LIGANDS

(75) Inventors: John Anthony Thomas Norman, Encinitas, CA (US); Melanie K. Perez, San Diego, CA (US); Xinjian Lei, Vista, CA (US); Daniel P. Spence, Carlsbad, CA (US); Sergei Vladimirovich Ivanov, Schnecksville, PA (US); Wade Hampton Bailey, III, Emmaus, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 22 days.

(21) Appl. No.: 13/363,918

(22) Filed: Feb. 1, 2012

(65) Prior Publication Data

US 2013/0078391 A1    Mar. 28, 2013

Related U.S. Application Data

(62) Division of application No. 13/152,885, filed on Jun. 3, 2011.

(60) Provisional application No. 61/354,023, filed on Jun. 11, 2010.

(51) Int. Cl.
*C07F 15/00* (2006.01)
*C23C 16/18* (2006.01)

(52) U.S. Cl.
USPC ..................... 548/101; 427/255.28

(58) Field of Classification Search
USPC ..................... 548/101; 427/255.28
See application file for complete search history.

(56) References Cited

U.S. PATENT DOCUMENTS

| | | |
|---|---|---|
| 7,037,872 B2 | 5/2006 | Aubert et al. |
| 2009/0200524 A1 | 8/2009 | Thompson et al. |
| 2009/0202740 A1 | 8/2009 | Thompson et al. |
| 2009/0209777 A1 | 8/2009 | Thompson et al. |
| 2009/0312561 A1 | 12/2009 | Eastham et al. |
| 2011/0120875 A1 | 5/2011 | Norman |
| 2012/0035351 A1 | 2/2012 | Norman |

FOREIGN PATENT DOCUMENTS

WO    2009086263 A1    7/2009

OTHER PUBLICATIONS

Perera et al. "î•5-Imidazolato Complexes of Ruthenium" Organometallics, 2000, vol. 19, pp. 5263-5265.*
Blanco, Fernando, N-σ versus π configuration in mono- and bis-pyrrole and imidazole derivatives of alkaline earth metals, Journal of Physical Organic Chemistry, 2009, pp. 747-755, vol. 22.
Perera, Jayani R., n5-Imidazolato Complexes of Ruthenium, Organometallics, 2000, pp. 5263-5265, vol. 19.
Spencer, Elinor C., Pressure-Induced Cooperative Bond Rearrangement in a Zinc Imidazolate Framework: A High-Pressure Single-Crystal X-Ray Diffraction Study, Journal American Chemical Society, 2009, vol. 131, pp. 4022-4026.
Tadokoro, Makoto, Cesium(I)-Mediated 3-D Superstructures by One-Pot Self-Organization of Hydrogen-Bonded Nickel Complexes, Inorganic Chemistry, 2001, vol. 40, pp. 5476-5478.
Huang, Hsiao-Wen, New Members of a Class of Dinitrosyliron Complexes (DNICs): Interconversion and Spectroscopic Discrimination of the Anionic {Fe(NO)2}9 [(NO)2Fe(C3H3N2)2]- and [(NO)2Fe(C3H3N2)(SR)]-(C3H3N2 = Deprotonated Imidazole; R = tBu, Et, Ph), Inorganic Chemistry, 2008 vol. 47 pp. 2196-2204.

* cited by examiner

*Primary Examiner* — Joseph Kosack
(74) *Attorney, Agent, or Firm* — Rosaleen P. Morris-Oskanian

(57)    ABSTRACT

Metal imidazolate complexes are described where imidazoles ligands functionalized with bulky groups and their anionic counterpart, i.e., imidazolates are described. Compounds comprising one or more such polyalkylated imidazolate anions coordinated to a metal or more than one metal, selected from the group consisting of alkali metals, transition metals, lanthanide metals, actinide metals, main group metals, including the chalcogenides, are contemplated. Alternatively, multiple different imidazole anions, in addition to other different anions, can be coordinated to metals to make new complexes. The synthesis of novel compounds and their use to form thin metal containing films is also contemplated.

32 Claims, 27 Drawing Sheets

COMPLEXES OF IMIDAZOLE LIGANDS

CROSS REFERENCE TO RELATED APPLICATION

The present patent application is a division of U.S. patent application Ser. No. 13/152,885 filed Jun. 3, 2011 and claims the benefit of prior U.S. Provisional Patent Application Ser. No. 61/354,023 filed Jun. 11, 2010.

BACKGROUND OF THE INVENTION

The semiconductor fabrication industry continues to source volatile metal containing precursors for vapor deposition processes, including chemical vapor deposition (CVD) and atomic layer deposition (ALD), plasma-enhanced ALD (PEALD) pulsed CVD, plasma enhanced CVD (PECVD) for fabricating conformal metal containing films on substrates, such as: silicon, metal, metal nitride, metal silicon nitride, metal oxide and other metal-containing layers, using these metal-containing precursors. The range of metals include those of the main group elements, transition metals, lanthanides and actinides. There is also a growing interest in volatile sources of chalcogenide based films containing such elements as germanium, antimony and tellurium for the growth of Phase Change Materials (PCM) for advanced memory applications. Additionally, any of these films can also be grown by super critical fluid deposition where the precursor is dissolved in a super critical fluid and a thin film grown from it.

For a metal compound to be useful as a volatile source for growing a metal containing film using the above mentioned processes it is typically important that it is stable enough to readily evaporate at elevated temperatures without decomposing, and similarly that its vapor is also thermally stable. This is acutely important for deposition processes such as ALD where the precursor vapor must be able to endure very high temperatures with no thermal decomposition occurring so that the film growth only occurs when the ALD reagent is cyclically added during the processing to build the growing film one layer at a time. If thermal decomposition of the precursor occurs then this effectively adds an undesired CVD component to the process and the step coverage of the growing film is degraded. In this respect, thermal stability of a precursor is highly prized. However, many precursors fall short of this ideal situation by decomposing at elevated temperatures. Currently, a major use of ALD in the semiconductor industry is the growth of metal oxides such as titanium oxide, zirconium oxide and lanthanide oxides. Often these processes are required to grow perfectly conformal films into deeply bored cylindrical volumes (vias) where it is imperative that there is no thermal decomposition or CVD component that will degrade conformality. One major mechanism by which precursors thermally degrade is when the anionic ligand to which the metal coordinates starts to decompose. Thus, making metal precursors which are coordinated to anions which are thermally robust is highly desirable.

Prior art in this field includes; WO 20099/086263 A1; US20090209777; US20090202740; US 2009/0200524; Journal of the American Chemical Society, 131, 4022-4026, 2009; M. Tadokoro, T. Shiomi, K. Isob, K. Nakasuji, *Inorganic Chem.* 40 5476-5478 (2001); Inorg. Chem. 2008, 47, 2196-2204; applicant's own pending patent applications U.S. Ser. No. 12/785,041 priority May 29, 2009 and U.S. Ser. No. 61/301,824 filed Feb. 5, 2010.

The prior art has attempted to provide precursors for these applications. However, none of the metal complexes in the prior art share the special characteristic of the complexes disclosed in the present invention. The compounds disclosed herein are exceptional in their volatility and thermal stability under conditions of vaporization. This makes them highly effective as precursors for thin film growth and any other application which requires volatile sources of metal, metalloids or chalcogenides.

BRIEF SUMMARY OF THE INVENTION

The present invention provides new metal complexes utilizing sterically hindered imidazolate ligands where at least one of carbons of the imidazolate are substituted with $C_1$-$C_{10}$ primary, secondary or tertiary alkyl; $C_1$-$C_{10}$ primary, secondary or tertiary alkoxy; $C_1$-$C_{10}$ primary, secondary or tertiary alkylamine; $C_1$-$C_{10}$ primary, secondary or tertiary alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ primary, secondary or tertiary alkyl functionalized with an ester group and mixtures thereof. These ring substituted groups are sufficiently bulky to induce 'eta-5' bonding of the imidazolate with metals, or eta-4, or eta-3 or eta-2 or eta-1 bonding to the metal. In addition, the bulk of the groups substituted on the imidazole anion is also carefully selected to be complementary to the bulk of other substituted imidazolates present and/or the bulk of other non-imidazolate anions and neutral ligands present so as to provide a coordinating environment to the metal which permits the formation of volatile monomeric or dimeric complexes, rather than involatile polymeric complexes.

DETAILED DESCRIPTION OF THE INVENTION

Figure 1:
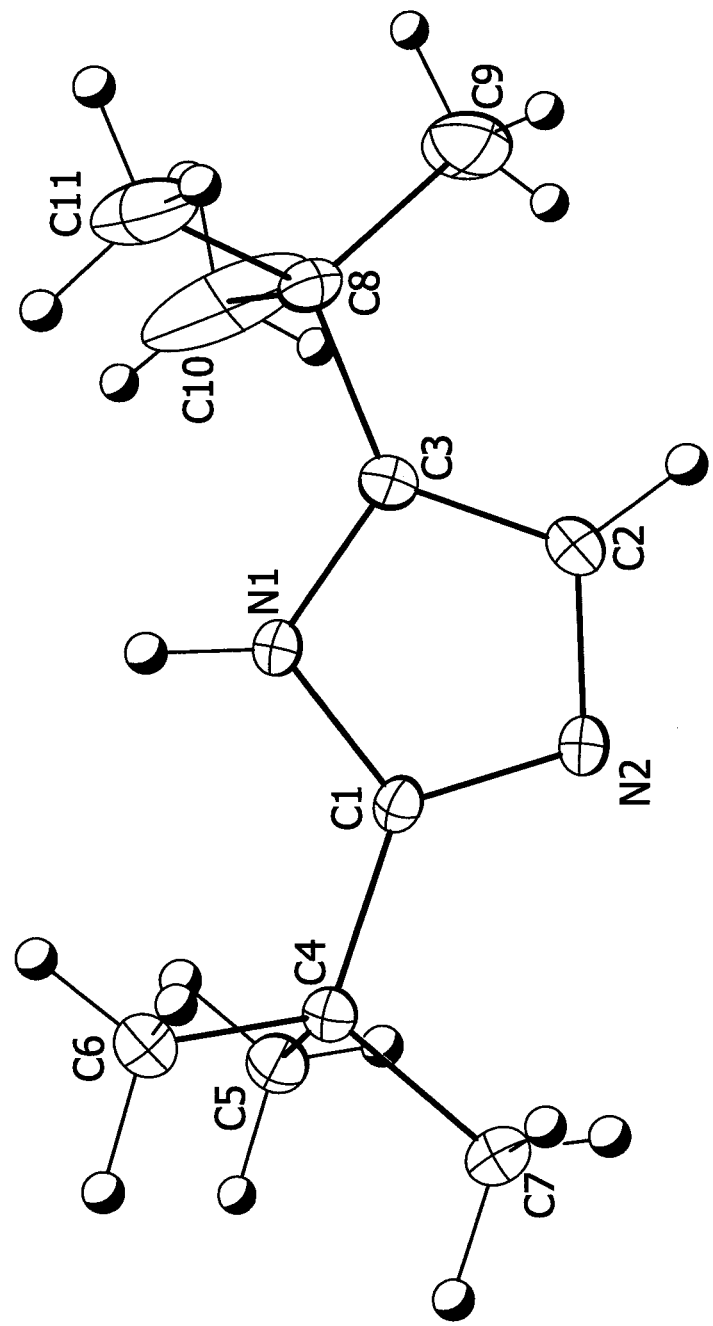
FIG. 1 shows the structure of 2,4-di-tert-butylimidazole, as determined by X-ray crystallography.

The present invention provides new monomeric or dimeric Group 3 to Group 16 metal complexes comprising sterically hindered mono-negative imidazolate, derived by deprotonation of imidazole ligands, represented by the formula below

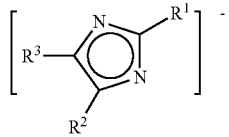

$R^{1-3}$ can be selected from hydrogen, linear or cyclic or branched $C_{1-10}$ alkyls, $C_{1-10}$ alkoxyalkyl, $C_{1-10}$ aminoalkyl, aromatic, and optionally further derivatized with other functional groups, such as; amine, hydroxyl, carboxylic, substituted amine and similar derivatives, wherein at least one of $R^1$, $R^2$ or $R^3$ is not hydrogen; preferably at least $R^1$ and $R^2$ are not hydrogen, and most preferably $R^1$, $R^2$ and $R^3$ are not hydrogen.

For the purpose of this invention sterically hindered mono-negative imidazolate ligands are selected to prevent formation of metal coordination polymers and to provide new monomeric or dimeric imidazolate metal complexes. For the purpose of this invention monomeric and dimeric complexes are metal complexes which readily form monomers and dimers at sufficiently low temperature <300° C. While it is well understood that higher order of coordination can be present when compounds of this invention are solids, steric hinderence around imidazolate ligands prevents strong intermolecular interactions between individual molecules. Thus, imidazolate complexes of this invention exists in monomeric or dimeric form already below 300° C., which allows these complexes to be sufficiently volatile with vapor pressure >0.01 torr at 200° C., preferably >0.1 torr at 200° C., and have low melting point <300° C., preferably <200° C., and more preferably <100° C. These physical properties are highly desirable for use of these materials for chemical vapor deposition of metal containing films.

The monomeric or dimeric metal imidazole complexes of this invention also evaporate cleanly by thermogravimetric analysis (TGA) with involatile residues <20 wt %, preferably <10 wt %, more preferably <5 wt %.

In contrast imidazolate complexes of the prior art do not have enough steric hinderance around the imidazolate ligands to prevent bridging of metal cations. Imidazolate complexes of the prior art tend to form strong polymeric complexes, known in the art as zeolitic imidazolate frameworks, as for example illustrated in Formula A. These complexes of the prior art are highly associated, and as such are involatile.

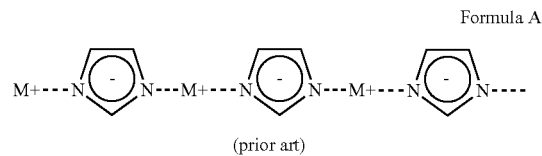

Formula A (prior art)

However, the metal imidazolate complexes of this disclosure overcome the above tendency towards polymerization by utilizing imidazole ligands which contain at least one substituent, preferably at the 2 position, to help disrupt coordination polymer formation, as above. As explained by the examples of this invention, for some metal complexes, it is advantageous to have bulky groups such as tert-butyl bonded to the 2, 4, and 5 carbon atoms of imidazole ring. For some ions, it is advantageous to have alkyl groups bonded to the 2, 4 and 5 carbon atoms that are smaller. In these examples, the alkyl groups can enable improved liquidity properties, while also providing lower molecular weight for improved volatility. Alkyl groups such as, but not limited to: methyl, ethyl, vinyl, propyl, isopropyl can be incorporated into the 2, 4 and/or 5 positions to optimize the properties for a given imidazolate anion to induce it to coordinate to a metal ion in novel ways, such as eta-5 as shown below in Formula B, thereby avoiding coordination polymer formation.

Thus, bulky groups for the purpose of the present invention are groups, which have sufficient 3-dimensional spacial form to create enough steric hindrance to preclude the bonding illustrated in Formula A, so that metals bonding with the imidazolates of the present invention are enabled to be preferably bonded in the 'eta-5' bonding or end on eta-1 bonding (no-coplanar bonding), as illustrated in Formulae B, C and D, respectively. Other bonding modes between these two extremes are also possible, such as eta-2, eta-3 and eta-4.

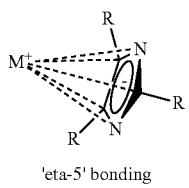

'eta-5' bonding

Formula B

The structure depicted in Formula B represents an unexpected result, in that the vast preponderance of imidazole anions (ie imidazolates) do not bind in an 'eta-5' or sideways manner, but rather 'end on' only through both the imidazolate's nitrogen atoms, as in Formula A. Direct evidence of this eta-5 coordination is provided by single crystal X-ray analysis in Examples 22, 23, 29, 30, 32, 33, 38 and 39 herein. In the Cambridge crystallographic data base, there is only one example of an eta-5 metal-to-imidazolate ion coordination (M. Tadokoro, T. Shiomi, K. Isob, K. Nakasuji, Inorganic Chem. 40 5476-5478 (2001)), and it occurs in an involatile mixed metal polymeric coordination compound, rather than in the discreet and volatile metal complexes of the present invention, further underscoring the unique character of the present invention's novel imidazole ligands.

In addition to the novel 'eta-5' bonding described above, the imidazolate ligands of this disclosure can also bind in a novel 'end on' mode where just one of the two nitrogens of the imidazolate bind to a metal center, as shown below in Formula C. Direct evidence of this eta-1 coordination is provided by single crystal X-ray analysis in Examples 16, 18, 19 and 20 herein. In the Cambridge data base, there is also only one example of an eta-1 binding imidazolate anion, but this occurs in a bimetallic iron/sodium imidazolate/nitrate 18-crown-6 complex, not reported as volatile, in contrast to the volatile molecules containing imidazole based anions, as described in this disclosure.

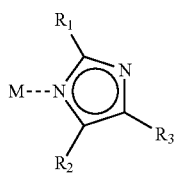

Formula C

In addition, when the steric requirements of the imidazole substituents are met, as above, an additional unique bridging mode exists, where the metal-to-imidazolate anion bonds are non-coplanar with the plane of the imidazolate anion, but with both metal-to imidazolate bonds oriented towards the same face of the imidazolate anion. In this way, a dimeric structure containing two metal ions can be prepared. Examples of this are depicted, below, in Formula D.

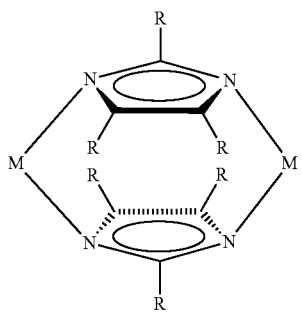

Formula D

To understand the unique character of the novel metal imidazolate compounds of this disclosure, it is instructive to consider the structure and substitutional numbering system of unsubstituted imidazole, as shown in Formula E, and imidazolate anion shown in Formula F. Note that the ring numbering system indicates that when all three carbon atoms of the imidazole ring are substituted with alkyl groups, then the resulting molecule would be called a 2,4,5-trialkylimidazole.

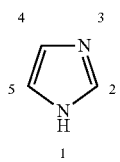

Formula E

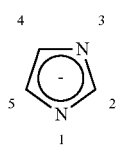

Formula F

When the N—H group of imidazole is deprotonated at position 1, the resulting formal negative charge of the anion thus created is delocalized throughout the five membered ring. However, if such an anion coordinates to metal cations, it will typically only do so through both of the nitrogen atoms, not involving the three carbon atoms of the ring. In this way, the imidazole anion most typically behaves as a 'bridging anion' between metal centers.

Bulky groups can comprise $C_{3-12}$ groups, preferably branched alkyl, cyclic or aromatic, and optionally further derivatized with other functional groups, such as; amine, hydroxyl, carboxylic, substituted amine and similar derivatives. Alkanes, alkenes, alkynes, cyclic forms of the same, aromatics, and their derivatives are all contemplated as bulky groups, as long as they meet the requirement of having sufficient bulk in the form of 3-dimensional spacial form to induce 'eta-5' bonding of the imidazole with metals, or eta-4, or eta-3 or eta-2 or eta-1 bonding to the metal. Other suitable bulky alkyl groups include, but not limited to; methyl, ethyl, propyl, isopropyl, tert-amyl, neopentyl, adamantly, hexyl, cyclohexyl, propyl, butyl, isobutyl, tertbutyl, pentyl, isopentyl, neopenty, norbornyl, bicyclo[2.2.1]heptyl, amido, nitro; $C_9$-$C_{20}$ alkylphenyl, $C_1$-$C_{10}$ alkoxy; alkylamine; $C_1$-$C_{10}$ alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ alkyl functionalized with an ester group and mixtures thereof.

This invention discloses the complexation of sterically hindered imidazolate anions to alkali metals, transition metals, lanthanide metal, actinide metals, and main group elements, including chalcogenides, to form new volatile molecules that can enjoy a wide range of utility, such as volatile precursors for thin film deposition by ALD/CVD.

The novel imidazolate based metal complexes of this disclosure are demonstrated to be of high thermal stability. The alkyl substituted imidazoles do not contain oxygen, which is a desirable property for metal-ligand systems, when used for metal and non-oxide dielectric depositions. The lack of oxygen within the ligand system can prevent oxidation, and the imidazoles should perform significantly better than their oxygen-containing counterparts in this regard. This invention discloses metal imidazolate compounds, where the imidazolate anion does not coordinate to multiple metal centers to form compounds of high nuclearity or polymers, which are either of low volatility or are involatile. So, in summation, the anionic imidazolate ligands need to coordinate a relatively low number of metal centers, such as 1 or 2; and are thermally very resilient against degradation.

To achieve such a highly stable anionic ligand also means that its formal negative charge needs to be stabilized by the structure of the ligand. The novel metal imidazolate compounds of this application are stabilized, due to the stability of the imidazolate anions upon which they are based. This stems from the ability of the imidazolate anions of this disclosure to stabilize their negative charge by being a five membered ring aromatic anion, which contains two nitrogen atoms. The electronegativity of the latter two atoms also increase the stability of the formal negative charge. Other five membered aromatic ring anions exist, such as cyclopentadienyl, but these are not as stable as the imidazolate anions of this disclosure. Also important is the shape of the imidazolate anion, because if its structure bears large bulky groups, such as tert-butyl, these can allow the nuclearity of the resulting metal complexes to be low, since bonding access to the ligand will be limited to 1 or 2 metal centers. This allows the novel imidazolate compounds of this disclosure to be volatile and highly useful as precursors.

Besides these features, it is also important that the novel imidazolate metal complexes of this disclosure include those that utilize asymmetrically substituted imidazole ligands. This helps to lower the symmetry of the imidazolate complex, which in turn can lower the crystal lattice packing energies and lower the melting point of the metal complex. It is particularly important to make pure metal complexes of lowered melting point or a liquid, since liquid precursors are easier to evaporate than solid precursors, and low melting point solids tend to be more soluble in solvents, to permit precursor delivery by DLI.

An example of the efficacy of this approach is found in the comparison of the melting points of ruthenium(trimethylimidazolate)(pentamethylcyclopentadienide) and ruthenium(2-ethyl-4-methylimidazolate)(pentamethylcyclopentadienide), as listed in Examples 31 and 32, respectively. Whereas the symmetrical trimethylimidazolate complex melts at 130.6° C., the asymmetric 2-ethyl-4-methylimidazolate containing complex melts at 64.1° C.

Metal complexes of sterically hindered imidazole ligands are disclosed, along with the syntheses of the same, which are highly volatile and stable complexes, that are exceptionally useful as precursor molecules for CVD, ALD, and the like, thin film deposition processes.

Compounds are described comprised of one or more polyalkylated imidazolate anions coordinated to a metal selected from the group consisting of a transition metal, a lanthanide metal, an actinide metal or main group element, including chalcogenides or mixtures thereof.

Alternatively, metal compounds can be made where a number of different imidazolate anions may be coordinated to the metal. In other embodiments, one or more imidazolate anions are coordinated to a metal and additional different anionic ligands are then also coordinated to the metal to balance its positive charge. Thus, if the metal is M and its cationic charge is (n+), imidazole anion is (I) and (X), (Y) and (Z) are a non-imidazolate anions, then the new and novel metal compounds of this disclosure are expressed as:

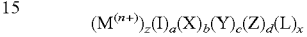

where (n) can be 1-6, (z) can be one or two, (b), (c) and (d) can individually range from zero to five, (a) can be from one to six with the provision that a, b, c, d, n and z are selected to make metal complex electroneutral. When X, Y and Z are monoanions than (a)+(b)+(c)+(d)=(z)×(n). Additionally, when (a) is greater than unity, the imidazolate anions can be the same or different, i.e., two or more unique imidazolate anions coordinate to the metal. L is a neutral coordinating molecule, such as; an ether, polyether, furans, amine, polyamine or alkoxyamine, pyridine etc. (L) can also be an unsaturated molecule, such as; an olefin, diolefin, triolefin or polyolefin, alkyne, silylolefin, silyalkyne, which can form a stabilizing organometallic bond to the metal. Similarly, (L) can also be carbon monoxide, nitrile, isonitrile, silylnitrile or isocyanide, alkyl phosphine, aromatic phosphine. Exemplary imidazoles from which the metal imidazolate complexes of this invention can be synthesized are as follows.

2-methylimidazole
2-ethylimidazole
2-propylimidazole
2-isopropylimidazole
2-tert-butylimidazole
2-(1,1-dimethylpropyl)imidazole
2,5-dimethylimidazole
2-ethyl-4-methylimidazole
2-propyl-4-methylimidazole
2-isopropyl-4-methylimidazole
2-tert-butyl-4-methylimidazole
2-(1,1-dimethylpropyl)-4-methylimidazole
2-methyl-4-ethylimidazole
2,4-diethylimidazole
2-propyl-4-ethylimidazole
2-isopropyl-4-ethylimidazole
2-tert-butyl-4-ethylimidazole
2-(1,1-dimethylpropyl)-4-ethylimidazole
2-methyl-4-propylimidazole
2-ethyl-4-propylimidazole
2,4-dipropylimidazole
2-isopropyl-4-propylimidazole
2-tert-butyl-4-propylimidazole
2-(1,1-dimethylpropyl)-4-propylimidazole
2-methyl-4-isopropylimidazole
2-ethyl-4-isopropylimidazole
2-propyl-4-isopropylimidazole
2,4-diisopropylimidazole
2-tert-butyl-4-isopropylimidazole
2-(1,1-dimethylpropyl)-4-isopropylimidazole
2-methyl-4-tert-butylimidazole
2-ethyl-tert-butylimidazole
2-propyl-tert-butylimidazole
2-isopropyl-4-tert-butylimidazole 2,4-di-tert-butylimidazole
2-(1,1-dimethylpropyl)-4-tert-butylimidazole
2-methyl-4-(1,1-dimethylpropyl)imidazole
2-ethyl-4-(1,1-dimethylpropyl)imidazole
2-propyl-4-(1,1-dimethylpropyl)imidazole
2-isopropyl-4-(1,1-dimethylpropyl)imidazole
2-tert-butyl-4-(1,1-dimethylpropyl)imidazole
2,4-di(1,1-dimethylpropyl)imidazole
2,4,5-trimethylimidazole
2-ethyl-4,5-dimethylimidazole
2-propyl-4,5-dimethylimidazole
2-isopropyl-4,5-dimethylimidazole
2-tert-butyl-4,5-dimethylimidazole
2-(1,1-dimethylpropyl)-4,5-dimethyl midazole
2,4-dimethyl-5-ethylimidazole
2,4-diethyl-5-methylimidazole
2-propyl-4-methyl-5-ethylimidazole
2-isopropyl-4-methyl-5-ethylimidazole
2-tert-butyl-4-methyl-5-ethyl imidazole
2-(1,1-dimethylpropyl)-4-methyl-5-ethylimidazole
2,4-dimethyl-5-propylimidazole
2-ethyl-4-methyl-5-propylimidazole
2,4-dipropyl-5-methylimidazole
2-isopropyl-4-methyl-5-propy imidazole
2-tert-butyl-4-methyl-5-propylimidazole
2-(1,1-dimethylpropyl)4-methyl-5-propylimidazole
2-methyl-4-ethyl-5-propylimidazole
2,4-diethyl-5-propylimidazole
2,4-dipropyl-5-ethylimidazole
2-isopropyl-4-ethyl-5-propyl imidazole
2-tert-butyl-4-ethyl-5-propylimidazole
2-(1,1-dimethylpropyl)-4-ethyl-5-propylimidazole
2-methyl-4,5-diethylimidazole
2,4,5-triethylethylimidazole
2-propyl-4,5-diethylimidazole
2-isopropyl-4,5-diethylimidazole
2-tert-butyl-4,5-diethylimidazole
2-(1,1-dimethylpropyl)-4,5-diethylimidazole
2-methyl-4,5-dipropylimidazole
2-ethyli-4,5-dipropylmidazole
2,4,5-tripropylimidazole
2-isopropyl-4,5-dipropylimidazole
2-tert-buty-4,5-dipropylimidazole
2-(1,1-dimethylpropyl)-4,5-dipropylimidazole
2,4,5-tri-tert-butylimidazole
2-tert-butyl-4,5-di-(1,1-dimethylpropyl)imidazole
2-tert-butyl-4,5-di-(1,1-dimethylbutyl)imidazole
2-tert-butyl-4,5-di-(1,1-dimethylpentyl)imidazole
2-tert-butyl-4,5-di-(1,1-dimethylhexyl)imidazole
2-(1,1-dimethylpropyl)-4,5-di-tert-butylimidazole
2,4,5-tri-(1,1-dimethylpropyl)imidazole
2-(1,1-dimethylpropyl)-4,5-di-(1,1-dimethylbutyl)imidazole
2-(1,1-dimethylpropyl)-4,5-di-(1,1-dimethylpentyl)imidazole
2-(1,1-dimethylpropyl)-4,5-di-(1,1-dimethylhexyl)imidazole
2-(1,1-dimethylbutyl)-4,5-di-tert-butylimidazole
2-(1,1-dimethylbutyl)-4,5-di-(1,1-dimethylpropyl)
2,4,5-tri-(1,1-dimethylbutyl)imidazole
2-(1,1-dimethylbutyl)-4,5-di-(1,1-dimethylpentyl)imidazole
2-(1,1-dimethylbutyl)-4,5-di-(1,1-dimethylhexyl)imidazole
2-(1,1-dimethylpentyl)-4,5-di-tert-butylimidazole
2-(1,1-dimethylpentyl)-4,5-di-(1,1-dimethylpropyl)limidazole
2-(1,1-dimethylpentyl)-4,5-di-(1,1-dimethylbutyl)limidazole
2,4,5-tri-(1,1-dimethylpentyl)imidazole
2-(1,1-dimethylpentyl)-4,5-di-(1,1-dimethylhexyl)limidazole
2-(1,1-dimethylhexyl)-4,5-di-tert-butylimidazole
2-(1,1-dimethylhexyl)-4,5-di-(1,1-dimethylpropyl)imidazole
2-(1,1-dimethylhexyl)-4,5-di-(1,1-dimethylbutyl)imidazole
2-(1,1-dimethylhexyl)-4,5-di-(1,1-dimethylpentyl)imidazole
2,4,5-tri-(1,1-dimethylhexyl)imidazole
2,4-di-tert-butyl-5-(1,1-dimethylpropyl)imidazole
2,5-di-tert-butyl-4-(1,1-dimethylpropyl)imidazole
2,4-di-tert-butyl-5-(1,1-dimethylbutyl)imidazole
2,5-di-tert-butyl-4-(1,1-dimethylbutyl)imidazole
2,4-di-tert-butyl-5-(1,1-dimethylpentyl)imidazole
2,5-di-tert-butyl-4-(1,1-dimethylpentyl)imidazole
2,4-di-tert-butyl-5-(1,1-dimethylhexyl)imidazole
2,5-di-tert-butyl-4-(1,1-dimethylhexyl)imidazole
2-tert-butyl-4-(1,1-dimethylpropyl)-5-(1,1-dimethylbutyl) imidazole
2-tert-butyl-4-(1,1-dimethylbutyl)-5-(1,1-dimethylpropyl) imidazole
2-tert-butyl-4-(1,1-dimethylpropyl)-5-(1,1-dimethylpentyl) imidazole
2-tert-butyl-4-(1,1-dimethylpentyl)-5-(1,1-dimethylpropyl) imidazole
2-tert-butyl-4-(1,1-dimethylpropyl)-5-(1,1-dimethylhexyl) imidazole
2-tert-butyl-4-(1,1-dimethylhexyl)-5-(1,1-dimethylpropyl) imidazole
2-tert-butyl-4-(1,1-dimethylpentyl)-5-(1,1-dimethylbutyl) imidazole
2-tert-butyl-4-(1,1-dimethylbutyl)-5-(1,1-dimethylpentyl) imidazole
2-tert-butyl-4-(1,1-dimethylpentyl)-5-(1,1-dimethylhexyl) imidazole
2-tert-butyl-4-(1,1-dimethylhexyl)-5-(1,1-dimethylpentyl) imidazole
2-(1,1-dimethylpropyl)-4-tert-butyl-5-(1,1-dimethylpropyl) imidazole
2-(1,1-dimethylpropyl)-4-(1,1-dimethylpropyl)-5-tert-butyl-imidazole
2-(1,1-dimethylpropyl)-4-tert-butyl-5-(1,1-dimethylbutyl) imidazole
2-(1,1-dimethylpropyl)-4-(1,1-dimethylbutyl)-5-tert-butyl-imidazole
2-(1,1-dimethylpropyl)-4-tert-butyl-5-(1,1-dimethylpentyl) imidazole
2-(1,1-dimethylpropyl)-4-(1,1-dimethylpentyl)-5-tert-butyl-imidazole
2-(1,1-dimethylpropyl)-4-tert-butyl-5-(1,1-dimethylhexyl) imidazole
2-(1,1-dimethylpropyl)-4-(1,1-dimethylhexyl)-5-tert-butyl-imidazole
2,4-di-(1,1-dimethylpropyl)-5-(1,1-dimethylbutyl)imidazole
2,5-di-(1,1-dimethylpropyl)-4-(1,1-dimethylbutyl)imidazole
2,4-di-(1,1-dimethylpropyl)-5-(1,1-dimethylpentyl)imidazole
2,5-di-(1,1-dimethylpropyl)-4-(1,1-dimethylpentyl)imidazole
2,4-di-(1,1-dimethylpropyl)-5-(1,1-dimethylhexyl)imidazole
2,5-di-(1,1-dimethylpropyl)-4-(1,1-dimethylhexyl)imidazole 2-(1,1-dimethylpropyl)-4-(1,1-dimethylpentyl)-5-(1,1-dimethylbutyl)imidazole
2-(1,1-dimethylpropyl)-4-(1,1-dimethylbutyl)-5-(1,1-dimethylpentyl)imidazole
2-(1,1-dimethylpropyl)-4-(1,1-dimethylpentyl)-5-(1,1-dimethylhexyl)imidazole
2-(1,1-dimethylpropyl)-4-(1,1-dimethylhexyl)-5-(1,1-dimethylpentyl)imidazole
2-(1,1-dimethylbutyl)-4-tert-butyl-5-(1,1-dimethylbutyl)imidazole
2-(1,1-dimethylbutyl)-4-(1,1-dimethylbutyl)-5-tert-butyl-imidazole
2,4-di(1,1-dimethylbutyl)-5-tert-butyl-imidazole
2,5-di(1,1-dimethylbutyl)-4-tert-butyl-imidazole
2-(1,1-dimethylbutyl)-4-tert-butyl-5-(1,1-dimethylpentyl)imidazole
2-(1,1-dimethylbutyl)-4-(1,1-dimethylpentyl)-5-tert-butyl imidazole
2-(1,1-dimethylbutyl)-4-tert-butyl-5-(1,1-dimethylhexyl)imidazole
2-(1,1-dimethylbutyl)-4-(1,1-dimethylhexyl)-5-tert-butyl-imidazole
2,4-di(1,1-dimethylbutyl)-5-(1,1-dimethylpropylimidazole
2,5-di(1,1-dimethylbutyl)-4-(1,1-dimethylpropyl)imidazole
2-(1,1-dimethylbutyl)-4-(1,1-dimethylpropyl)-5-(1,1-dimethylpentyl)imidazole
2-(1,1-dimethylbutyl)-4-(1,1-dimethylpentyl)-5-(1,1-dimethylpropyl)imidazole
2-(1,1-dimethylbutyl)-4-(1,1-dimethylpropyl)-5-(1,1-dimethylhexyl)imidazole
2-(1,1-dimethylbutyl)-4-(1,1-dimethylhexyl)-5-(1,1-dimethylpropyl)imidazole
2,4-(1,1-dimethylbutyl)-5-(1,1-dimethylbutyl)imidazole
2,5-(1,1-dimethylbutyl)-4-(1,1-dimethylbutyl)imidazole
2-(1,1-dimethylbutyl)-4-(1,1-dimethylpentyl)-5-(1,1-dimethylhexyl)imidazole
2-(1,1-dimethylbutyl)-4-(1,1-dimethylhexyl)-5-(1,1-dimethylpentyl)imidazole
2-(1,1-dimethylpentyl)-4-tert-butyl-5-(1,1-dimethylpropyl)imidazole
2-(1,1-dimethylpentyl)-4-(1,1-dimethylpropyl)-5-tert-butyl-imidazole
2-(1,1-dimethylpentyl)-4-tert-butyl-5-(1,1-dimethylbutyl)imidazole
2-(1,1-dimethylpentyl)-4-(1,1-dimethylbutyl)-5-tert-butyl-imidazole
2-(1,1-dimethylpentyl)-4-tert-butyl-5-(1,1-dimethylpentyl)imidazole
2-(1,1-dimethylpentyl)-4-(1,1-dimethylpentyl)-5-tert-butyl-imidazole
2-(1,1-dimethylpentyl)-4-tert-butyl-5-(1,1-dimethylhexyl)imidazole
2-(1,1-dimethylpentyl)-4-(1,1-dimethylhexyl)-5-tert-butyl-imidazole
2-(1,1-dimethylpentyl)-4-(1,1-dimethylpropyl)-5-(1,1-dimethylbutyl)imidazole
2-(1,1-dimethylpentyl)-4-(1,1-dimethylbutyl)-5-(1,1-dimethylpropyl)imidazole
2,4-di-(1,1-dimethylpentyl)-5-(1,1-dimethylpropyl)imidazole
2,5-di-(1,1-dimethylpentyl)-4-(1,1-dimethylpropyl)imidazole
2-(1,1-dimethylpentyl)-4-(1,1-dimethylpropyl)-5-(1,1-dimethylhexyl)imidazole
2-(1,1-dimethylpentyl)-4-(1,1-dimethylhexyl)-5-(1,1-dimethylpropyl)imidazole
2,4-(1,1-dimethylpentyl)-5-(1,1-dimethylbutyl)imidazole
2,5-(1,1-dimethylpentyl)-4-(1,1-dimethylbutyl)imidazole
2,4-(1,1-dimethylpentyl)-5-(1,1-dimethylhexyl)imidazole
2,5-(1,1-dimethylpentyl)-4-(1,1-dimethylhexyl)imidazole
2-(1,1-dimethylhexyl)-4-tert-butyl-5-(1,1-dimethylpropyl)imidazole
2-(1,1-dimethylhexyl)-4-(1,1-dimethylpropyl)-5-tert-butyl-imidazole
2-(1,1-dimethylhexyl)-4-tert-butyl-5-(1,1-dimethyl butyl)imidazole
2-(1,1-dimethylhexyl)-4-(1,1-dimethyl butyl)-5-tert-butyl-imidazole
2-(1,1-dimethylhexyl)-4-tert-butyl-5-(1,1-dimethylpentyl)imidazole
2-(1,1-dimethylhexyl)-4-(1,1-dimethylpentyl)-5-tert-butyl-imidazole
2-(1,1-dimethylhexyl)-4-tert-butyl-5-(1,1-dimethyl hexyl)imidazole
2-(1,1-dimethylhexyl)-4-(1,1-dimethyl hexyl)-5-tert-butyl-imidazole
2-(1,1-dimethylhexyl)-4-(1,1-dimethylpropyl)-5-(1,1-dimethyl butyl)imidazole
2-(1,1-dimethylhexyl)-4-(1,1-dimethyl butyl)-5-(1,1-dimethylpropyl)imidazole
2-(1,1-dimethylhexyl)-4-(1,1-dimethylpropyl)-5-(1,1-dimethylpentyl)imidazole
2-(1,1-dimethylhexyl)-4-(1,1-dimethylpentyl)-5-(1,1-dimethylpropyl)imidazole
2,4-di(1,1-dimethylhexyl)-5-(1,1-dimethylpropyl)imidazole
2,5-di(1,1-dimethylhexyl)-4-(1,1-dimethylpropyl)imidazole
2-(1,1-dimethylhexyl)-4-(1,1-dimethylpentyl)-5-(1,1-dimethyl butyl)imidazole
2-(1,1-dimethylhexyl)-4-(1,1-dimethyl butyl)-5-(1,1-dimethylpentyl)imidazole
2,4-di(1,1-dimethylhexyl)-5-(1,1-dimethylpentyl)imidazole
2,5-di(1,1-dimethylhexyl)-4-(1,1-dimethylpentyl)imidazole
2-(1-methylethyl)-4,5-di-tert-butylimidazole
2-(1-methylethyl)-4,5-di(1,1-dimethylpropyl)imidazole
2-(1-methylethyl)-4,5-di(1,1-dimethylbutyl)imidazole
2-(1-methylethyl)-4,5-di(1,1-dimethylpentyl)imidazole
2-(1-methylethyl)-4,5-di(1,1-dimethylhexyl)imidazole
2,4,5-tri(1-methylethyl)imidazole
2-(1-methylethyl)-4-tert-butyl-5-(1,1-dimethylpropyl)imidazole
2-(1-methylethyl)-4-(1,1-dimethylpropyl)-5-tert-butylimidazole
2-(1-methylethyl)-4-(1,1-dimethylbutyl)-5-tert-butylimidazole
2-(1-methylethyl)-4-tert-butylimidazole-5-(1,1-dimethylbutyl)imidazole
2-(1-methylethyl)-4-(1,1-dimethylpentyl)-5-tert-butylimidazole
2-(1-methylethyl)-4-tert-butylimidazole-5-(1,1-dimethylpentyl)imidazole
2-(1-methylethyl)-4-(1,1-dimethylhexyl)-5-tert-butylimidazole
2-(1-methylethyl)-4-tert-butylimidazole-5-(1,1-dimethylhexyl)imidazole
2-(1-methylethyl)-4-(1,1-dimethylhexyl)-5-tert-butylimidazole
2-(1-methylethyl)-4-(1,1-dimethylpropyl)-5-(1,1-dimethylbutyl)imidazole
2-(1-methylethyl)-4-(1,1-dimethylbutyl)-5-(1,1-dimethylpropyl)-imidazole
2-(1-methylethyl)-4-(1,1-dimethylpropyl)-5-(1,1-dimethylpentyl)imidazole
2-(1-methylethyl)-4-(1,1-dimethylpentyl)-5-(1,1-dimethylpropyl)-imidazole 2-(1-methylethyl)-4-(1,1-dimethylpropyl)-5-(1,1-dimethylhexyl)imidazole
2-(1-methylethyl)-4-(1,1-dimethylhexyl)-5-(1,1-dimethylpropyl)-imidazole
2-(1-methylethyl)-4-(1,1-dimethylpentyl)-5-(1,1-dimethylbutyl)-imidazole
2-(1-methylethyl)-4-(1,1-dimethylbutyl)-5-(1,1-dimethylpentyl)-imidazole
2-(1-methylethyl)-4-(1,1-dimethylpentyl)-5-(1,1-dimethylhexyl)-imidazole
2-(1-methylethyl)-4-(1,1-dimethylhexyl)-5-(1,1-dimethylpentyl)-imidazole
2,4-di-tert-butyl-5-(1-methylethyl)imidazole
2,5-di-tert-butyl-4-(1-methylethyl)imidazole
2-tert-butyl-4-(1,1-dimethylpropyl)-5-(1-methylethyl)imidazole
2-tert-butyl-4-(1-methylethyl)-5-(1,1-dimethylbutyl)imidazole
2-tert-butyl-4-(1,1-dimethylbutyl)-5-(1-methylethyl)imidazole
2-tert-butyl-4-(1-methylethyl)-5-(1,1-dimethylpentyl)imidazole
2-tert-butyl-4-(1,1-dimethylpentyl)-5-(1-methylethyl)imidazole
2-tert-butyl-4-(1-methylethyl)-5-(1,1-dimethylhexyl)imidazole
2-tert-butyl-4-(1,1-dimethylhexyl)-5-(1-methylethyl)imidazole
2-(1,1-dimethylpropyl)-4-tert-butyl-5-(1-methylethyl)imidazole
2-(1,1-dimethylpropyl)-4-(1-methylethyl)-5-tert-butylimidazole
2-(1,1-dimethylpropyl)-4-tert-butyl-5-(1-methylethyl)imidazole
2,4-di(1,1-dimethylpropyl)-5-(1-methylethyl)-imidazole
2,5-di(1,1-dimethylpropyl)-4-(1-methylethyl)-imidazole
2-(1,1-dimethylpropyl)-4-(1,1-dimethylethyl)-5-(1,1-dimethylbutyl)imidazole
2-(1,1-dimethylpropyl)-4-(1,1-dimethylbutyl)-5-(1,1-dimethylethyl)imidazole
2-(1,1-dimethylpropyl)-4-(1,1-dimethylethyl)-5-(1,1-dimethylpentyl)imidazole
2-(1,1-dimethylpropyl)-4-(1,1-dimethylpentyl)-5-(1,1-dimethylethyl)imidazole
2-(1,1-dimethylpropyl)-4-(1,1-dimethylethyl)-5-(1,1-dimethylhexyl)imidazole
2-(1,1-dimethylpropyl)-4-(1,1-dimethylhexyl)-5-(1,1-dimethylethyl)imidazole
2-(1,1-dimethylbutyl)-4-tert-butyl-5-(1-methylethyl)imidazole
2-(1,1-dimethylbutyl)-4-(1-methylethyl)-5-tert-butyl-5-imidazole
2-(1,1-dimethylbutyl)-4-(1-methylethyl)-5-(1,1-dimethylpropyl)imidazole
2-(1,1-dimethylbutyl)-4-(1,1-dimethylpropyl)-5-(1-methylethyl)imidazole
2-(1,1-dimethylbutyl)-4-(1-methylethyl)-5-(1,1-dimethylbutyl)imidazole
2-(1,1-dimethylbutyl)-4-(1,1-dimethylbutyl)-5-(1-methylethyl)imidazole
2-(1,1-dimethylbutyl)-4-(1-methylethyl)-5-(1,1-dimethylpentyl)imidazole
2-(1,1-dimethylbutyl)-4-(1,1-dimethylpentyl)-5-(1-methylethyl)imidazole
2-(1,1-dimethylbutyl)-4-(1-methylethyl)-5-(1,1-dimethylhexyl)imidazole
2-(1,1-dimethylbutyl)-4-(1,1-dimethylhexyl)-5-(1-methylethyl)imidazole
2-(1,1-dimethylpentyl)-4-(1,1-dimethylethyl)-5-tert-butylimidazole
2-(1,1-dimethylpentyl)-4-tert-butyl-5-(1,1-dimethylethyl)imidazole
2-(1,1-dimethylpentyl)-4-(1,1-dimethylethyl)-5-tert-butylimidazole
2-(1,1-dimethylpentyl)-4-(1,1-dimethylpropyl)-5-(1,1-dimethylethyl)imidazole
2-(1,1-dimethylpentyl)-4-(1,1-dimethylethyl)-5-(1,1-dimethylpropyl)-5-midazole
2-(1,1-dimethylpentyl)-4-(1,1-dimethylbutyl)-5-(1,1-dimethylethyl)imidazole
2-(1,1-dimethylpentyl)-4-(1,1-dimethylethyl)-5-(1,1-dimethylbutyl)-5-midazole
2-(1,1-dimethylpentyl)-4-(1,1-dimethylbutyl)-5-(1,1-dimethylethyl)imidazole
2,4-di(1,1-dimethylpentyl)-5-(1,1-dimethylethyl)imidazole
2,5-di(1,1-dimethylpentyl)-4-(1,1-dimethylethyl)imidazole
2-(1,1-dimethylpentyl)-4-(1,1-dimethylethyl)-5-(1,1-dimethylhexyl)-5-midazole
2-(1,1-dimethylpentyl)-4-(1,1-dimethylhexyl)-5-(1,1-dimethylethyl)imidazole
2-(1,1-dimethylhexyl)-4-tert-butyl-5-(1,1-dimethylethyl)imidazole
2-(1,1-dimethylhexyl)-4-(1,1-dimethylethyl)-5-tert-butylimidazole
2-(1,1-dimethylhexyl)-4-(1,1-dimethylpropyl)-5-(1,1-dimethylethyl)imidazole
2-(1,1-dimethylhexyl)-4-(1,1-dimethylethyl)-5-(1,1-dimethylpropyl)imidazole
2-(1,1-dimethylhexyl)-4-(1,1-dimethylbutyl)-5-(1-methylethyl)imidazole
2-(1,1-dimethylhexyl)-4-(1-methylethyl)-5-(1,1-dimethylbutyl)-5 imidazole
2-(1,1-dimethylhexyl)-4-(1,1-dimethylpentyl)-5-(1-methylethyl)imidazole
2-(1,1-dimethylhexyl)-4-(1-methylethyl)-5-(1,1-dimethylpentyl) imidazole
2,4-di(1,1-dimethylhexyl)-5-(1-methylethyl)imidazole
2,5-di(1,1-dimethylhexyl)-4-(1-methylethyl)imidazole
2,4-(1-methylethyl)-5-tert-butylimidazole
2,5-(1-methylethyl)-4-tert-butylimidazole
2,4-(1-methylethyl)-5-(1,1-dimethylpropyl)imidazole
2,5-(1-methylethyl)-4-(1,1-dimethylpropyl)imidazole
2,4-(1-methylethyl)-5-(1,1-dimethylbutyl)imidazole
2,5-(1-methylethyl)-4-(1,1-dimethylbutyl)imidazole
2,4-(1-methylethyl)-5-(1,1-dimethylpentyl)imidazole
2,5-(1-methylethyl)-4-(1,1-dimethylpentyl)imidazole
2,4-(1-methylethyl)-5-(1,1-dimethylhexyl)imidazole
2,5-(1-methylethyl)-4-(1,1-dimethylhexyl)imidazole
2-(1,2-dimethylpropyl)-4,5-di-tert-butylimidazole
2-(1,2-dimethylpropyl)-4,5-di-(1,1-dimethylpropyl)imidazole
2-(1,2-dimethylpropyl)-4,5-di-(1,1-dimethylbutyl)imidazole
2-(1,2-dimethylpropyl)-4,5-di-(1,1-dimethylpentyl)imidazole
2-(1,2-dimethylpropyl)-4,5-di-(1,1-dimethylhexyl)imidazole
2-(1,2-dimethylpropyl)-4,5-di-(1-methylethyl)imidazole
2-(1,2-dimethylpropyl)-4-tert-butyl-5-(1,1-dimethylpropyl) imidazole
2-(1,2-dimethylpropyl)-4-(1,1-dimethylpropyl)-5-tert-butylimidazole 2-(1,2-dimethylpropyl)-4-tert-butyl-5-(1,1-dimethylbutyl) imidazole
2-(1,2-dimethylpropyl)-4-(1,1-dimethylbutyl)-5-tert-butylimidazole
2-(1,2-dimethylpropyl)-4-tert-butyl-5-(1,1-dimethylpentyl) imidazole
2-(1,2-dimethylpropyl)-4-(1,1-dimethylpentyl)-5-tert-butylimidazole
2-(1,2-dimethylpropyl)-4-tert-butyl-5-(1,1-dimethylhexyl) imidazole
2-(1,2-dimethylpropyl)-4-(1,1-dimethylhexyl)-5-tert-butylimidazole
2-(1,2-dimethylpropyl)-4-(1,1-dimethylpropyl)-5-(1,1-dimethylbutyl)imidazole
2-(1,2-dimethylpropyl)-4-(1,1-dimethylbutyl)-5-(1,1-dimethylpropyl)imidazole
2-(1,2-dimethylpropyl)-4-(1,1-dimethylpropyl)-5-(1,1-dimethylpentyl)imidazole
2-(1,2-dimethylpropyl)-4-(1,1-dimethylpentyl)-5-(1,1-dimethylpropyl)imidazole
2-(1,2-dimethylpropyl)-4-(1,1-dimethylpropyl)-5-(1,1-dimethylhexyl)imidazole
2-(1,2-dimethylpropyl)-4-(1,1-dimethylhexyl)-5-(1,1-dimethylpropyl)imidazole
2-(1,2-dimethylpropyl)-4-(1,1-dimethylpentyl)-5-(1,1-dimethylbutyl)imidazole
2-(1,2-dimethylpropyl)-4-(1,1-dimethylbutyl)-5-(1,1-dimethylpentyl)imidazole
2-(1,2-dimethylpropyl)-4-(1,1-dimethylhexyl)-5-(1,1-dimethylbutyl)imidazole
2-(1,2-dimethylpropyl)-4-(1,1-dimethylbutyl)-5-(1,1-dimethylhexyl)imidazole
2-(1,2-dimethylpropyl)-4-tert-butyl-5-(1-methylethyl)imidazole
2-(1,2-dimethylpropyl)-4-(1-methylethyl)-5-tert-butylimidazole
2-(1,2-dimethylpropyl)-4-tert-butyl-5-(1-methylethyl)imidazole
2-(1,2-dimethylpropyl)-4-(1-methylethyl)-5-(1,1-dimethylpropyl)imidazole
2-(1,2-dimethylpropyl)-4-(1,1-dimethylpropyl)-(1-methylethyl)imidazole
2-(1,2-dimethylpropyl)-4-(1-methylethyl)-5-(1,1-dimethylbutyl)imidazole
2-(1,2-dimethylpropyl)-4-(1,1-dimethylbutyl)-(1-methylethyl)imidazole
2-(1,2-dimethylpropyl)-4-(1-methylethyl)-5-(1,1-dimethylpentyl)imidazole
2-(1,2-dimethylpropyl)-4-(1,1-dimethylpentyl)-5-(1-methylethyl)imidazole
2-(1,2-dimethylpropyl)-4-(1-methylethyl)-5-(1,1-dimethylhexyl)imidazole
2-(1,2-dimethylpropyl)-4-(1,1-dimethylhexyl)-5-(1-methylethyl)imidazole
2,4-di-tert-butyl-5-(1,2-dimethylpropyl)imidazole
2,5-di-tert-butyl-4-(1,2-dimethylpropyl)imidazole
2-tert-butyl-4-(1,1-dimethylpropyl)-5-(1,2-dimethylpropyl) imidazole
2-tert-butyl-4-(1,2-dimethylpropyl)-5-(1,1-dimethylpropyl) imidazole
2-tert-butyl-4-(1,1-dimethylbutyl)-5-(1,2-dimethylpropyl) imidazole
2-tert-butyl-4-(1,2-dimethylpropyl)-5-(1,1-dimethylbutyl) imidazole
2-tert-butyl-4-(1,1-dimethylpentyl)-5-(1,2-dimethylpropyl) imidazole
2-tert-butyl-4-(1,2-dimethylpropyl)-5-(1,1-dimethylpentyl) imidazole
2-tert-butyl-4-(1,1-dimethylhexyl)-5-(1,2-dimethylpropyl) imidazole
2-tert-butyl-4-(1,2-dimethylpropyl)-5-(1,1-dimethylhexyl) imidazole
2-tert-butyl-4-(1-methylethyl)-5-(1,2-dimethylpropyl)imidazole
2-tert-butyl-4-(1,2-dimethylpropyl)-5-(1-methylethyl)imidazole
2-(1,1-dimethylpropyl)-4-tert-butyl-5-(1,2-dimethylpropyl) imidazole
2-(1,1-dimethylpropyl)-4-(1,2-dimethylpropyl)-5-tert-butylimidazole
2,4-(1,1-dimethylpropyl)-5-(1,2-dimethylpropyl)imidazole
2,5-(1,1-dimethylpropyl)-4-(1,2-dimethylpropyl)imidazole
2-(1,1-dimethylpropyl)-4-(1,2-dimethylpropyl)-5-(1,1-dimethylbutyl)imidazole
2-(1,1-dimethylpropyl)-4-(1,1-dimethylbutyl)-5-(1,2-dimethylpropyl)imidazole
2-(1,1-dimethylpropyl)-4-(1,2-dimethylpropyl)-5-(1,1-dimethylpentyl)imidazole
2-(1,1-dimethylpropyl)-4-(1,1-dimethylpentyl)-5-(1,2-dimethylpropyl)imidazole
2-(1,1-dimethylpropyl)-4-(1,2-dimethylpropyl)-5-(1,1-dimethylhexyl)imidazole
2-(1,1-dimethylpropyl)-4-(1,1-dimethylhexyl)-5-(1,2-dimethylpropyl)imidazole
2-(1,1-dimethylpropyl)-4-(1,2-dimethylpropyl)-5-(1-methylethyl)imidazole
2-(1,1-dimethylpropyl)-4-(1-methylethyl)-5-(1,2-dimethylpropyl)imidazole
2-(1,1-dimethylpropyl)-4-tert-butyl-5-(1,2-dimethylpropyl) imidazole
2-(1,1-dimethylbutyl)-4-(1,2-dimethylpropyl)-5-tert-butylimidazole
2-(1,1-dimethylbutyl)-4-tert-butyl-5-(1,2-dimethylpropyl)-5-imidazole
2-(1,1-dimethylbutyl)-4-(1,2-dimethylpropyl)-5-(1,1-dimethylpropyl)imidazole
2-(1,1-dimethylbutyl)-4-(1,1-dimethylpropyl)-5-(1,2-dimethylpropyl)imidazole
2,4-di(1,1-dimethylbutyl)-5-(1,2-dimethylpropyl)imidazole
2,5-di(1,1-dimethylbutyl)-4-(1,2-dimethylpropyl)imidazole
2-(1,1-dimethylbutyl)-4-(1,1-dimethylpentyl)-5-(1,2-dimethylpropyl)imidazole
2-(1,1-dimethylbutyl)-4-(1,2-dimethylpropyl)-5-(1,1-dimethylpentyl)-5-imidazole
2-(1,1-dimethylbutyl)-4-(1,1-dimethylhexyl)-5-(1,2-dimethylpropyl)imidazole
2-(1,1-dimethylbutyl)-4-(1,2-dimethylpropyl)-5-(1,1-dimethylhexyl)-5-imidazole
2-(1,1-dimethylbutyl)-4-(1-methylethyl)-5-(1,2-dimethylpropyl)imidazole
2-(1,1-dimethylbutyl)-4-(1,2-dimethylpropyl)-5-(1-methylethyl)-5-imidazole
2-(1,1-dimethylpentyl)-4-tert-butyl-5-(1,2-dimethylpropyl) imidazole
2-(1,1-dimethylpentyl)-4-(1,2-dimethylpropyl)-5-tert-butylimidazole
2-(1,1-dimethylpentyl)-4-(1,2-dimethylpropyl)-5-(1,1-dimethylpropyl)imidazole
2-(1,1-dimethylpentyl)-4-(1,1-dimethylpropyl)-5(-1,2-dimethylpropyl)-5imidazole
2-(1,1-dimethylpentyl)-4-(1,2-dimethylpropyl)-5-(1,1-dimethylbutyl)imidazole 2,4-di(1,1-dimethylpentyl)-5-(1,2-dimethylpropyl))imidazole
2,5-di(1,1-dimethylpentyl)-4-(1,2-dimethylpropyl))imidazole
2-(1,1-dimethylpentyl)-4-(1,1-dimethylhexyl)-5-(1,2-dimethylpropyl)imidazole
2-(1,1-dimethylpentyl)-4-(1,2-dimethylpropyl)-5-(1,1-dimethylhexyl)imidazole
2-(1,1-dimethylpentyl)-4-(1-methylethyl)-5-(1,2-dimethylpropyl)imidazole
2-(1,1-dimethylpentyl)-4-(1,2-dimethylpropyl)-5-(1-methylethyl)imidazole
2-(1,1-dimethylhexyl)-4-(1,2-dimethylpropyl)-5-tert-butylimidazole
2-(1,1-dimethylhexyl)-4-tert-butyl-5-(1,2-dimethylpropyl)imidazole
2-(1,1-dimethylhexyl)-4-(1,2-dimethylpropyl)-5-(1,1-dimethylpropyl)imidazole
2-(1,1-dimethylhexyl)-4-(1,1-dimethylpropyl)-5-(1,2-dimethylpropyl)imidazole
2-(1,1-dimethylhexyl)-4-(1,2-dimethylpropyl)-5-(1,1-dimethylbutyl)imidazole
2-(1,1-dimethylhexyl)-4-(1,1-dimethylbutyl)-5-(1,2-dimethylpropyl)imidazole
2-(1,1-dimethylhexyl)-4-(1,2-dimethylpropyl)-5-(1,1-dimethylpentyl)imidazole
2-(1,1-dimethylhexyl)-4-(1,1-dimethylpentyl)-5-(1,2-dimethylpropyl)imidazole
2,4-di(1,1-dimethylhexyl)-5-(1,2-dimethylpropyl)imidazole
2,5-di(1,1-dimethylhexyl)-4-(1,2-dimethylpropyl)imidazole
2-(1,1-dimethylhexyl)-4-(1,2-dimethylpropyl)-5-(1-methylethyl)imidazole
2-(1,1-dimethylhexyl)-4-(1-methylethyl)-5-(1,2-dimethylpropyl)imidazole
2-(1-methylethyl)-4-tert-butyl-5-(1,2-dimethylpropyl)imidazole
2-(1-methylethyl)-4-(1,2-dimethylpropyl)-5-tert-butyl-imidazole
2-(1-methylethyl)-4-tert-butyl-5-(1,2-dimethylpropyl)imidazole
2-(1-methylethyl)-4-(1,2-dimethylpropyl)-5-(1,1-dimethylpropyl)imidazole
2-(1-methylethyl)-4-(1,1-dimethylpropyl)-5-(1,2-dimethylpropyl)imidazole
2-(1-methylethyl)-4-(1,2-dimethylpropyl)-5-(1,1-dimethylbutyl)imidazole
2-(1-methylethyl)-4-(1,1-dimethylbutyl)-5-(1,2-dimethylpropyl)imidazole
2-(1-methylethyl)-4-(1,2-dimethylpropyl)-5-(1,1-dimethylpentyl)imidazole
2-(1-methylethyl)-4-(1,1-dimethylpentyl)-5-(1,2-dimethylpropyl)imidazole
2-(1-methylethyl)-4-(1,2-dimethylpropyl)-5-(1,1-dimethylhexyl)imidazole
2-(1-methylethyl)-4-(1,1-dimethylhexyl)-5-(1,2-dimethylpropyl)imidazole
2,4-di(1-methylethyl)-5-(1,2-dimethylpropyl)imidazole
2,5-di(1-methylethyl)-4-(1,2-dimethylpropyl)imidazole
2,4-di(1,2-dimethylpropyl)-5-tert-butylimidazole
2,5-di(1,2-dimethylpropyl)-4-tert-butylimidazole
2,4-di(1,2-dimethylpropyl)-5-(1,1-dimethylpropyl)imidazole
2,5-di(1,2-dimethylpropyl)-4-(1,1-dimethylpropyl)imidazole
2,4-di(1,2-dimethylpropyl)-5-(1,1-dimethylbutyl)imidazole
2,5-di(1,2-dimethylpropyl)-4-(1,1-dimethylbutyl)imidazole
2,4-di(1,2-dimethylpropyl)-5-(1,1-dimethylpentyl)imidazole
2,5-di(1,2-dimethylpropyl)-4-(1,1-dimethylpentyl)imidazole
2,4-di(1,2-dimethylpropyl)-5-(1,1-dimethylhexyl)imidazole
2,5-di(1,2-dimethylpropyl)-4-(1,1-dimethylhexyl)imidazole
2,4-di(1,2-dimethylpropyl)-5-(1-methylethyl)imidazole
2,5-di(1,2-dimethylpropyl)-4-(1-methylethyl)imidazole
Preferably the imidazole is
2,4,5-tri-tert-butylimidazole
2-tert-butyl-4,5-di-(1,1-dimethylpropyl)imidazole
2-tert-butyl-4,5-di-(1,1-dimethylbutyl)imidazole
2-tert-butyl-4,5-di-(1,1-dimethylpentyl)imidazole
2-tert-butyl-4,5-di-(1,1-dimethylhexyl)imidazole
2-(1,1-dimethylpropyl)-4,5-di-tert-butylimidazole
2,4,5-tri-(1,1-dimethylpropyl)imidazole
2-(1,1-dimethylpropyl)-4,5-di-(1,1-dimethylbutyl)imidazole
2-(1,1-dimethylpropyl)-4,5-di-(1,1-dimethylpentyl)imidazole
2-(1,1-dimethylpropyl)-4,5-di-(1,1-dimethylhexyl)imidazole
2-(1,1-dimethylbutyl)-4,5-di-tert-butylimidazole
2-(1,1-dimethylbutyl)-4,5-di-(1,1-dimethylpropyl)
2,4,5-tri-(1,1-dimethylbutyl)imidazole
2-(1,1-dimethylbutyl)-4,5-di-(1,1-dimethylpentyl)imidazole
2-(1,1-dimethylbutyl)-4,5-di-(1,1-dimethylhexyl)imidazole
2-(1,1-dimethylpentyl)-4,5-di-tert-butylimidazole
2-(1,1-dimethylpentyl)-4,5-di-(1,1-dimethylpropyl)limidazole
2-(1,1-dimethylpentyl)-4,5-di-(1,1-dimethylbutyl)limidazole
2,4,5-tri-(1,1-dimethylpentyl)imidazole
2-(1,1-dimethylpentyl)-4,5-di-(1,1-dimethylhexyl)limidazole
2-(1,1-dimethylhexyl)-4,5-di-tert-butylimidazole
2-(1,1-dimethylhexyl)-4,5-di-(1,1-dimethylpropyl)imidazole
2-(1,1-dimethylhexyl)-4,5-di-(1,1-dimethylbutyl)imidazole
2-(1,1-dimethylhexyl)-4,5-di-(1,1-dimethylpentyl)imidazole
2,4,5-tri-(1,1-dimethylhexyl)imidazole
2,4-di-tert-butyl-5-(1,1-dimethylpropyl)imidazole
2,5-di-tert-butyl-4-(1,1-dimethylpropyl)imidazole
2,4-di-tert-butyl-5-(1,1-dimethylbutyl)imidazole
2,5-di-tert-butyl-4-(1,1-dimethylbutyl)imidazole
2,4-di-tert-butyl-5-(1,1-dimethylpentyl)imidazole
2,5-di-tert-butyl-4-(1,1-dimethylpentyl)imidazole
2,4-di-tert-butyl-5-(1,1-dimethylhexyl)imidazole
2,5-di-tert-butyl-4-(1,1-dimethylhexyl)imidazole
2-tert-butyl-4-(1,1-dimethylpropyl)-5-(1,1-dimethylbutyl)imidazole
2-tert-butyl-4-(1,1-dimethylbutyl)-5-(1,1-dimethylpropyl)imidazole
2-tert-butyl-4-(1,1-dimethylpropyl)-5-(1,1-dimethylpentyl)imidazole
2-tert-butyl-4-(1,1-dimethylpentyl)-5-(1,1-dimethylpropyl)imidazole
2-tert-butyl-4-(1,1-dimethylpropyl)-5-(1,1-dimethylhexyl)imidazole
2-tert-butyl-4-(1,1-dimethylhexyl)-5-(1,1-dimethylpropyl)imidazole
2-tert-butyl-4-(1,1-dimethylpentyl)-5-(1,1-dimethylbutyl)imidazole
2-tert-butyl-4-(1,1-dimethylbutyl)-5-(1,1-dimethylpentyl)imidazole 2-tert-butyl-4-(1,1-dimethylpentyl)-5-(1,1-dimethylhexyl)imidazole
2-tert-butyl-4-(1,1-dimethylhexyl)-5-(1,1-dimethylpentyl)imidazole
2-(1,1-dimethylpropyl)-4-tert-butyl-5-(1,1-dimethylpropyl)imidazole
2-(1,1-dimethylpropyl)-4-(1,1-dimethylpropyl)-5-tert-butyl-imidazole
2-(1,1-dimethylpropyl)-4-tert-butyl-5-(1,1-dimethylbutyl)imidazole
2-(1,1-dimethylpropyl)-4-(1,1-dimethylbutyl)-5-tert-butyl-imidazole
2-(1,1-dimethylpropyl)-4-tert-butyl-5-(1,1-dimethylpentyl)imidazole
2-(1,1-dimethylpropyl)-4-(1,1-dimethylpentyl)-5-tert-butyl-imidazole
2-(1,1-dimethylpropyl)-4-tert-butyl-5-(1,1-dimethylhexyl)imidazole
2-(1,1-dimethylpropyl)-4-(1,1-dimethylhexyl)-5-tert-butyl-imidazole
2,4-di-(1,1-dimethylpropyl)-5-(1,1-dimethylbutyl)imidazole
2,5-di-(1,1-dimethylpropyl)-4-(1,1-dimethylbutyl)imidazole
2,4-di-(1,1-dimethylpropyl)-5-(1,1-dimethylpentyl)imidazole
2,5-di-(1,1-dimethylpropyl)-4-(1,1-dimethylpentyl)imidazole
2,4-di-(1,1-dimethylpropyl)-5-(1,1-dimethylhexyl)imidazole
2,5-di-(1,1-dimethylpropyl)-4-(1,1-dimethylhexyl)imidazole
2-(1,1-dimethylpropyl)-4-(1,1-dimethylpentyl)-5-(1,1-dimethylbutyl)imidazole
2-(1,1-dimethylpropyl)-4-(1,1-dimethylbutyl)-5-(1,1-dimethylpentyl)imidazole
2-(1,1-dimethylpropyl)-4-(1,1-dimethylpentyl)-5-(1,1-dimethylhexyl)imidazole
2-(1,1-dimethylpropyl)-4-(1,1-dimethylhexyl)-5-(1,1-dimethylpentyl)imidazole
2-(1,1-dimethylbutyl)-4-tert-butyl-5-(1,1-dimethylbutyl)imidazole
2-(1,1-dimethylbutyl)-4-(1,1-dimethylbutyl)-5-tert-butyl-imidazole
2,4-di(1,1-dimethylbutyl)-5-tert-butyl-imidazole
2,5-di(1,1-dimethylbutyl)-4-tert-butyl-imidazole
2-(1,1-dimethylbutyl)-4-tert-butyl-5-(1,1-dimethylpentyl)imidazole
2-(1,1-dimethylbutyl)-4-(1,1-dimethylpentyl)-5-tert-butyl imidazole
2-(1,1-dimethylbutyl)-4-tert-butyl-5-(1,1-dimethylhexyl)imidazole
2-(1,1-dimethylbutyl)-4-(1,1-dimethylhexyl)-5-tert-butyl-imidazole
2,4-di(1,1-dimethylbutyl)-5-(1,1-dimethylpropylimidazole
2,5-di(1,1-dimethylbutyl)-4-(1,1-dimethylpropyl)imidazole
2-(1,1-dimethylbutyl)-4-(1,1-dimethylpropyl)-5-(1,1-dimethylpentyl)imidazole
2-(1,1-dimethylbutyl)-4-(1,1-dimethylpentyl)-5-(1,1-dimethylpropyl)imidazole
2-(1,1-dimethylbutyl)-4-(1,1-dimethylpropyl)-5-(1,1-dimethylhexyl)imidazole
2-(1,1-dimethylbutyl)-4-(1,1-dimethylhexyl)-5-(1,1-dimethylpropyl)imidazole
2,4-(1,1-dimethylbutyl)-5-(1,1-dimethylbutyl)imidazole
2,5-(1,1-dimethylbutyl)-4-(1,1-dimethylbutyl)imidazole
2-(1,1-dimethylbutyl)-4-(1,1-dimethylpentyl)-5-(1,1-dimethylhexyl)imidazole
2-(1,1-dimethylbutyl)-4-(1,1-dimethylhexyl)-5-(1,1-dimethylpentyl)imidazole
2-(1,1-dimethylpentyl)-4-tert-butyl-5-(1,1-dimethylpropyl)imidazole
2-(1,1-dimethylpentyl)-4-(1,1-dimethylpropyl)-5-tert-butyl-imidazole
2-(1,1-dimethylpentyl)-4-tert-butyl-5-(1,1-dimethylbutyl)imidazole
2-(1,1-dimethylpentyl)-4-(1,1-dimethylbutyl)-5-tert-butyl-imidazole
2-(1,1-dimethylpentyl)-4-tert-butyl-5-(1,1-dimethylpentyl)imidazole
2-(1,1-dimethylpentyl)-4-(1,1-dimethylpentyl)-5-tert-butyl-imidazole
2-(1,1-dimethylpentyl)-4-tert-butyl-5-(1,1-dimethylhexyl)imidazole
2-(1,1-dimethylpentyl)-4-(1,1-dimethylhexyl)-5-tert-butyl-imidazole
2-(1,1-dimethylpentyl)-4-(1,1-dimethylpropyl)-5-(1,1-dimethylbutyl)imidazole
2-(1,1-dimethylpentyl)-4-(1,1-dimethylbutyl)-5-(1,1-dimethylpropyl)imidazole
2,4-di-(1,1-dimethylpentyl)-5-(1,1-dimethylpropyl)imidazole
2,5-di-(1,1-dimethylpentyl)-4-(1,1-dimethylpropyl)imidazole
2-(1,1-dimethylpentyl)-4-(1,1-dimethylpropyl)-5-(1,1-dimethylhexyl)imidazole
2-(1,1-dimethylpentyl)-4-(1,1-dimethylhexyl)-5-(1,1-dimethylpropyl)imidazole
2,4-(1,1-dimethylpentyl)-5-(1,1-dimethylbutyl)imidazole
2,5-(1,1-dimethylpentyl)-4-(1,1-dimethylbutyl)imidazole
2,4-(1,1-dimethylpentyl)-5-(1,1-dimethylhexyl)imidazole
2,5-(1,1-dimethylpentyl)-4-(1,1-dimethylhexyl)imidazole
2-(1,1-dimethylhexyl)-4-tert-butyl-5-(1,1-dimethylpropyl)imidazole
2-(1,1-dimethylhexyl)-4-(1,1-dimethylpropyl)-5-tert-butyl-imidazole
2-(1,1-dimethylhexyl)-4-tert-butyl-5-(1,1-dimethyl butyl)imidazole
2-(1,1-dimethylhexyl)-4-(1,1-dimethyl butyl)-5-tert-butyl-imidazole
2-(1,1-dimethylhexyl)-4-tert-butyl-5-(1,1-dimethylpentyl)imidazole
2-(1,1-dimethylhexyl)-4-(1,1-dimethylpentyl)-5-tert-butyl-imidazole
2-(1,1-dimethylhexyl)-4-tert-butyl-5-(1,1-dimethyl hexyl)imidazole
2-(1,1-dimethylhexyl)-4-(1,1-dimethyl hexyl)-5-tert-butyl-imidazole
2-(1,1-dimethylhexyl)-4-(1,1-dimethylpropyl)-5-(1,1-dimethyl butyl)imidazole
2-(1,1-dimethylhexyl)-4-(1,1-dimethyl butyl)-5-(1,1-dimethylpropyl)imidazole
2-(1,1-dimethylhexyl)-4-(1,1-dimethylpropyl)-5-(1,1-dimethylpentyl)imidazole
2-(1,1-dimethylhexyl)-4-(1,1-dimethylpentyl)-5-(1,1-dimethylpropyl)imidazole
2,4-di(1,1-dimethylhexyl)-5-(1,1-dimethylpropyl)imidazole
2,5-di(1,1-dimethylhexyl)-4-(1,1-dimethylpropyl)imidazole
2-(1,1-dimethylhexyl)-4-(1,1-dimethylpentyl)-5-(1,1-dimethyl butyl)imidazole
2-(1,1-dimethylhexyl)-4-(1,1-dimethyl butyl)-5-(1,1-dimethylpentyl)imidazole
2,4-di(1,1-dimethylhexyl)-5-(1,1-dimethylpentyl)imidazole 2,5-di(1,1-dimethylhexyl)-4-(1,1-dimethylpentyl)imidazole
Preferably the imidazole is
2,4,5-tri-tert-butylimidazole
2-tert-butyl-4,5-di-(1,1-dimethylpropyl)imidazole
2-(1,1-dimethylbutyl)-4,5-di-tert-butylimidazole
2-(1,1-dimethylbutyl)-4,5-di-(1,1-dimethylpropyl)imidazole
2-tertbutyl-4,5-di(1-methyl-1-ethylpropyl)imidazole
2-(1,1-dimethylpropyl)-4,5-di(1-methyl-1-ethylpropyl)imidazole
2-(1,1-dimethylbutyl)-4,5-di(1-methyl-1-ethylpropyl)imidazole
2-(1,1-dimethylpentyl)-4,5-di(1-methyl-1-ethylpropyl)imidazole
2-(1,1-dimethylhexyl)-4,5-di(1-methyl-1-ethylpropyl)imidazole
2-(1,1-dimethylhexyl)-4,5-di(1-methyl-1-ethylpropyl)imidazole
2-(1-methylethyl)-4,5-di(1-methyl-1-ethylpropyl)imidazole
2,4,5-tri(1-methyl-1-ethylpropyl)imidazole
2,4-di-ter-butyl-5-(1-methyl-1-ethylpropyl)imidazole
2,5-di-ter-butyl-4-(1-methyl-1-ethylpropyl)imidazole
2-tert-butyl-4-(1,1-dimethylpropyl)-5-(1-methyl-1-ethylpropyl)imidazole
2-tert-butyl-5-(1,1-dimethylpropyl)-4-(1-methyl-1-ethylpropyl)imidazole
2-tert-butyl-4-(1,1-dimethylbutyl)-5-(1-methyl-1-ethylpropyl)imidazole
2-tert-butyl-5-(1,1-dimethylbutyl)-4-(1-methyl-1-ethylpropyl)imidazole
2-tert-butyl-4-(1,1-dimethylpentyl)-5-(1-methyl-1-ethylpropyl)imidazole
2-tert-butyl-5-(1,1-dimethylpentyl)-4-(1-methyl-1-ethylpropyl)imidazole
2-tert-butyl-4-(1,1-dimethylhexyl)-5-(1-methyl-1-ethylpropyl)imidazole
2-tert-butyl-5-(1,1-dimethylhexyl)-4-(1-methyl-1-ethylpropyl)imidazole
2-tert-butyl-4-(1-methylpropyl)-5-(1-methyl-1-ethylpropyl)imidazole
2-tert-butyl-5-(1-methylpropyl)-4-(1-methyl-1-ethylpropyl)imidazole
2-tert-butyl-4-(1,2-dimethylpropyl)-5-(1-methyl-1-ethylpropyl)imidazole
2-tert-butyl-5-(1,2-dimethylpropyl)-4-(1-methyl-1-ethylpropyl)imidazole
2-(1,1-dimethylpropyl)-4-tert-butyl-5-(1-methyl-1-ethylpropyl)imidazole
2-(1,1-dimethylpropyl)-5-tert-butyl-4-(1-methyl-1-ethylpropyl)imidazole
2,4-(1,1-dimethylpropyl)-5-(1-methyl-1-ethylpropyl)imidazole
2-(1,1-dimethylpropyl)-4-(1,1-dimethylbutyl)-5-(1-methyl-1-ethylpropyl)imidazole
2-(1,1-dimethylpropyl)-5-(1,1-dimethylbutyl)-4-(1-methyl-1-ethylpropyl)imidazole
2-(1,1-dimethylpropyl)-4-(1,1-dimethylpentyl)-5-(1-methyl-1-ethylpropyl)imidazole
2-(1,1-dimethylpropyl)-5-(1,1-dimethylpentyl)-4-(1-methyl-1-ethylpropyl)imidazole
2-(1,1-dimethylpropyl)-4-(1,1-dimethylhexyl)-5-(1-methyl-1-ethylpropyl)imidazole
2-(1,1-dimethylpropyl)-5-(1,1-dimethylhexyl)-4-(1-methyl-1-ethylpropyl)imidazole
2-(1,1-dimethylpropyl)-4-(1-methylethyl)-5-(1-methyl-1-ethylpropyl)imidazole
2-(1,1-dimethylpropyl)-5-(1-methylethyl)-4-(1-methyl-1-ethylpropyl)imidazole
2-(1,1-dimethylpropyl)-4-(1,2-dimethylpropyl)-5-(1-methyl-1-ethylpropyl)imidazole
2-(1,1-dimethylpropyl)-5-(1,1-dimethylpropyl)-4-(1-methyl-1-ethylpropyl)imidazole
2-(1,1-dimethylbutyl)-4-tert-butyl-5-(1-methyl-1-ethylpropyl)imidazole
2-(1,1-dimethylbutyl)-5-tert-butyl-4-(1-methyl-1-ethylpropyl)imidazole
2-(1,1-dimethylbutyl)-4-(1,1-dimethylpropyl)-5-(1-methyl-1-ethylpropyl)imidazole
2-(1,1-dimethylbutyl)-5-(1,1-dimethylpropyl)-4-(1-methyl-1-ethylpropyl)imidazole
2,4-di(1,1-dimethylbutyl)-5-(1-methyl-1-ethylpropyl)imidazole
2,5-di(1,1-dimethylbutyl)-4-(1-methyl-1-ethylpropyl)imidazole
2-(1,1-dimethylbutyl)-4-(1,1-dimethylpentyl)-5-(1-methyl-1-ethylpropyl)imidazole
2-(1,1-dimethylbutyl)-5-(1,1-dimethylpentyl)-4-(1-methyl-1-ethylpropyl)imidazole
2-(1,1-dimethylbutyl)-4-(1,1-dimethylhexyl)-5-(1-methyl-1-ethylpropyl)imidazole
2-(1,1-dimethylbutyl)-5-(1,1-dimethylhexyl)-4-(1-methyl-1-ethylpropyl)imidazole
2-(1,1-dimethylbutyl)-4-(1-methylethyl)-5-(1-methyl-1-ethylpropyl)imidazole
2-(1,1-dimethylbutyl)-5-(1-methylethyl)-4-(1-methyl-1-ethylpropyl)imidazole
2-(1,1-dimethylbutyl)-4-(1,2-dimethylpropyl)-5-(1-methyl-1-ethylpropyl)imidazole
2-(1,1-dimethylbutyl)-5-(1,2-dimethylpropyl)-4-(1-methyl-1-ethylpropyl)imidazole
2-(1,1-dimethylpentyl)-4-tert-butyl-5-(1-methyl-1-ethylpropyl)imidazole
2-(1,1-dimethylpentyl)-5-tert-butyl-4-(1-methyl-1-ethylpropyl)imidazole
2-(1,1-dimethylpentyl)-4-(1,1-dimethylpropyl)-5-(1-methyl-1-ethylpropyl)imidazole
2-(1,1-dimethylpentyl)-5-(1,1-dimethylpropyl)-4-(1-methyl-1-ethylpropyl)imidazole
2-(1,1-dimethylpentyl)-4-(1,1-dimethylbutyl)-5-(1-methyl-1-ethylpropyl)imidazole
2-(1,1-dimethylpentyl)-5-(1,1-dimethylbutyl)-4-(1-methyl-1-ethylpropyl)imidazole
2-4-di(1,1-dimethylpentyl)-5-(1-methyl-1-ethylpropyl)imidazole
2-5-di(1,1-dimethylpentyl)-4-(1-methyl-1-ethylpropyl)imidazole
2-(1,1-dimethylpentyl)-4-(1,1-dimethylhexyl)-5-(1-methyl-1-ethylpropyl)imidazole
2-(1,1-dimethylpentyl)-5-(1,1-dimethylhexyl)-4-(1-methyl-1-ethylpropyl)imidazole
2-(1,1-dimethylpentyl)-4-(1-methylethyl)-5-(1-methyl-1-ethylpropyl)imidazole
2-(1,1-dimethylpentyl)-5-(1-methylethyl)-4-(1-methyl-1-ethylpropyl)imidazole
2-(1,1-dimethylpentyl)-4-(1,2-dimethylpropyl)-5-(1-methyl-1-ethylpropyl)imidazole
2-(1,1-dimethylpentyl)-5-(1,2-dimethylpropyl)-4-(1-methyl-1-ethylpropyl)imidazole
2-(1,1-dimethylhexyl)-4-tert-butyl-5-(1-methyl-1-ethylpropyl)imidazole
2-(1,1-dimethylhexyl)-5-tert-butyl-4-(1-methyl-1-ethylpropyl)imidazole 2-(1,1-dimethylhexyl)-4-(1,1-dimethylpropyl)-5-(1-methyl-1-ethylpropyl)imidazole
2-(1,1-dimethylhexyl)-5-(1,1-dimethylpropyl)-4-(1-methyl-1-ethylpropyl)imidazole
2-(1,1-dimethylhexyl)-4-(1,1-dimethylbutyl)-5-(1-methyl-1-ethylpropyl)imidazole
2-(1,1-dimethylhexyl)-5-(1,1-dimethylbutyl)-4-(1-methyl-1-ethylpropyl)imidazole
2-(1,1-dimethylhexyl)-4-(1,1-dimethylpentyl)-5-(1-methyl-1-ethylpropyl)imidazole
2-(1,1-dimethylhexyl)-5-(1,1-dimethylpentyl)-4-(1-methyl-1-ethylpropyl)imidazole
2,4-(1,1-dimethylhexyl)-5-(1-methyl-1-ethylpropyl)imidazole
2,5-(1,1-dimethylhexyl)-4-(1-methyl-1-ethylpropyl)imidazole
2-(1,1-dimethylhexyl)-4-(1-methylethyl)-5-(1-methyl-1-ethylpropyl)imidazole
2-(1,1-dimethylhexyl)-5-(1-methylethyl)-4-(1-methyl-1-ethylpropyl)imidazole
2-(1,1-dimethylhexyl)-4-(1,2-dimethylpropyl)-5-(1-methyl-1-ethylpropyl)imidazole
2-(1,1-dimethylhexyl)-5-(1,2-dimethylpropyl)-4-(1-methyl-1-ethylpropyl)imidazole
2-(1-methylethyl)-4-tert-butyl-5-(1-methyl-1-ethylpropyl)imidazole
2-(1-methylethyl)-5-tert-butyl-4-(1-methyl-1-ethylpropyl)imidazole
2-(1-methylethyl)-4-(1,1-dimethylpropyl)-5-(1-methyl-1-ethylpropyl)imidazole
2-(1-methylethyl)-5-(1,1-dimethylpropyl)-4-(1-methyl-1-ethylpropyl)imidazole
2-(1-methylethyl)-4-(1,1-dimethylbutyl)-5-(1-methyl-1-ethylpropyl)imidazole
2-(1-methylethyl)-5-(1,1-dimethylbutyl)-4-(1-methyl-1-ethylpropyl)imidazole
2-(1-methylethyl)-4-(1,1-dimethylpentyl)-5-(1-methyl-1-ethylpropyl)imidazole
2-(1-methylethyl)-5-(1,1-dimethylpentyl)-4-(1-methyl-1-ethylpropyl)imidazole
2-(1-methylethyl)-4-(1,1-dimethylhexyl)-5-(1-methyl-1-ethylpropyl)imidazole
2-(1-methylethyl)-5-(1,1-dimethylhexyl)-4-(1-methyl-1-ethylpropyl)imidazole
2,4-di(1-methylethyl)-5-(1-methyl-1-ethylpropyl)imidazole
2,5-di(1-methylethyl)-4-(1-methyl-1-ethylpropyl)imidazole
2-(1-methylethyl)-4-(1,2-dimethylpropyl)-5-(1-methyl-1-ethylpropyl)imidazole
2-(1-methylethyl)-5-(1,2-dimethylpropyl)-4-(1-methyl-1-ethylpropyl)imidazole
2-(1,2-dimethylpropyl)-4-tert-butyl-5-(1-methyl-1-ethylpropyl)imidazole
2-(1,2-dimethylpropyl)-5-tert-butyl-4-(1-methyl-1-ethylpropyl)imidazole
2-(1,2-dimethylpropyl)-4-(1,1-dimethylpropyl)-5-(1-methyl-1-ethylpropyl)imidazole
2-(1,2-dimethylpropyl)-5-(1,1-dimethylpropyl)-4-(1-methyl-1-ethylpropyl)imidazole
2-(1,2-dimethylpropyl)-4-(1,1-dimethylbutyl)-5-(1-methyl-1-ethylpropyl)imidazole
2-(1,2-dimethylpropyl)-5-(1,1-dimethylbutyl)-4-(1-methyl-1-ethylpropyl)imidazole
2-(1,2-dimethylpropyl)-4-(1,1-dimethylpentyl)-5-(1-methyl-1-ethylpropyl)imidazole
2-(1,2-dimethylpropyl)-5-(1,1-dimethylpentyl)-4-(1-methyl-1-ethylpropyl)imidazole
2-(1,2-dimethylpropyl)-4-(1,1-dimethylhexyl)-5-(1-methyl-1-ethylpropyl)imidazole
2-(1,2-dimethylpropyl)-5-(1,1-dimethylhexyl)-4-(1-methyl-1-ethylpropyl)imidazole
2-(1,2-dimethylpropyl)-4-(1-methylethyl)-5-(1-methyl-1-ethylpropyl)imidazole
2-(1,2-dimethylpropyl)-5-(1-methylethyl)-4-(1-methyl-1-ethylpropyl)imidazole
2,4-(1,2-dimethylpropyl)-5-(1-methyl-1-ethylpropyl)imidazole
2,5-(1,2-dimethylpropyl)-4-(1-methyl-1-ethylpropyl)imidazole
2-(1-methyl-1-ethylpropyl)-4-tert-butyl-5-(1,1-dimethylpropyl)imidazole
2-(1-methyl-1-ethylpropyl)-5-tert-butyl-4-(1,1-dimethylpropyl)imidazole
2-(1-methyl-1-ethylpropyl)-4-tert-butyl-5-(1,1-dimethylbutyl)imidazole
2-(1-methyl-1-ethylpropyl)-5-tert-butyl-4-(1,1-dimethylbutyl)imidazole
2-(1-methyl-1-ethylpropyl)-4-tert-butyl-5-(1,1-dimethylpentyl)imidazole
2-(1-methyl-1-ethylpropyl)-5-tert-butyl-4-(1,1-dimethylpentyl)imidazole
2-(1-methyl-1-ethylpropyl)-4-tert-butyl-5-(1,1-dimethylhexyl)imidazole
2-(1-methyl-1-ethylpropyl)-5-tert-butyl-4-(1,1-dimethylhexyl)imidazole
2-(1-methyl-1-ethylpropyl)-4-(1,1-dimethylpropyl)-5-(dimethylbutyl)imidazole
2-(1-methyl-1-ethylpropyl)-4-(1,1-dimethylpropyl)-5-(dimethylbutyl)imidazole
2-(1-methyl-1-ethylpropyl)-4-(1,1-dimethylpropyl)-5-(dimethylpentyl)imidazole
2-(1-methyl-1-ethylpropyl)-4-(1,1-dimethylpropyl)-5-(dimethylpentyl)imidazole
2-(1-methyl-1-ethylpropyl)-4-(1,1-dimethylpropyl)-5-(dimethylhexyl)imidazole
2-(1-methyl-1-ethylpropyl)-4-(1,1-dimethylpropyl)-5-(dimethylhexyl)imidazole
2-(1-methyl-1-ethylpropyl)-4-(dimethylpentyl)-5-(1,1-dimethylbutyl)imidazole
2-(1-methyl-1-ethylpropyl)-5-(dimethylpentyl)-4-(1,1-dimethylbutyl)imidazole
2-(1-methyl-1-ethylpropyl)-4-(dimethylpentyl)-5-(1,1-dimethylhexyl)imidazole
2-(1-methyl-1-ethylpropyl)-5-(dimethylpentyl)-4-(1,1-dimethylhexyl)imidazole
2-(1-methyl-1-ethylpropyl)-4-tert-butyl-5-(1-methylethyl)imidazole
2-(1-methyl-1-ethylpropyl)-5-tert-butyl-4-(1-methylethyl)imidazole
2-(1-methyl-1-ethylpropyl)-4-(1,1-dimethylpropyl)-5-(1-methylethyl)imidazole
2-(1-methyl-1-ethylpropyl)-5-(1,1-dimethylpropyl)-4-(1-methylethyl)imidazole
2-(1-methyl-1-ethylpropyl)-4-(1,1-dimethylbutyl)-5-(1-methylethyl)imidazole
2-(1-methyl-1-ethylpropyl)-5-(1,1-dimethylbutyl)-4-(1-methylethyl)imidazole
2-(1-methyl-1-ethylpropyl)-4-(1,1-dimethylpentyl)-5-(1-methylethyl)imidazole
2-(1-methyl-1-ethylpropyl)-5-(1,1-dimethylpentyl)-4-(1-methylethyl)imidazole
2-(1-methyl-1-ethylpropyl)-4-(1,1-dimethylhexyl)-5-(1-methylethyl)imidazole 2-(1-methyl-1-ethylpropyl)-5-(1,1-dimethylhexyl)-4-(1-methylethyl)imidazole
2-(1-methyl-1-ethylpropyl)-4-tert-butyl-5-(1,2-dimethylpropyl)imidazole
2-(1-methyl-1-ethylpropyl)-5-tert-butyl-4-(1,2-dimethylpropyl)imidazole
2-(1-methyl-1-ethylpropyl)-4-tert-butyl-5-(1,2-dimethylpropyl)imidazole
2-(1-methyl-1-ethylpropyl)-4-(1,1-dimethylpropyl)-5-(1,2-dimethylpropyl)imidazole
2-(1-methyl-1-ethylpropyl)-5-(1,1-dimethylpropyl)-4-(1,2-dimethylpropyl)imidazole
2-(1-methyl-1-ethylpropyl)-4-(1,1-dimethylbutyl)-5-(1,2-dimethylpropyl)imidazole
2-(1-methyl-1-ethylpropyl)-5-(1,1-dimethylbutyl)-4-(1,2-dimethylpropyl)imidazole
2-(1-methyl-1-ethylpropyl)-4-(1,1-dimethylpentyl)-5-(1,2-dimethylpropyl)imidazole
2-(1-methyl-1-ethylpropyl)-5-(1,1-dimethylpentyl)-4-(1,2-dimethylpropyl)imidazole
2-(1-methyl-1-ethylpropyl)-4-(1,1-dimethylhexyl)-5-(1,2-dimethylpropyl)imidazole
2-(1-methyl-1-ethylpropyl)-5-(1,1-dimethylhexyl)-4-(1,2-dimethylpropyl)imidazole
2-(1-methyl-1-ethylpropyl)-4-(1-methylethyl)-5-(1,2-dimethylpropyl)imidazole
2-(1-methyl-1-ethylpropyl)-5-(1-methylethyl)-4-(1,2-dimethylpropyl)imidazole
2,4-di(1-methyl-1-ethylpropyl)-5-tert-butylimidazole
2,5-di(1-methyl-1-ethylpropyl)-4-tert-butylimidazole
2,4-di(1-methyl-1-ethylpropyl)-5-(1,1-dimethylpropyl)imidazole
2,5-di(1-methyl-1-ethylpropyl)-4-(1,1-dimethylpropyl)imidazole
2,4-di(1-methyl-1-ethylpropyl)-5-(1,1-dimethylbutyl)imidazole
2,5-di(1-methyl-1-ethylpropyl)-4-(1,1-dimethylbutyl)imidazole
2,4-di(1-methyl-1-ethylpropyl)-5-(1,1-dimethylpentyl)imidazole
2,5-di(1-methyl-1-ethylpropyl)-4-(1,1-dimethylpentyl)imidazole
2,4-di(1-methyl-1-ethylpropyl)-5-(1,1-dimethylhexyl)imidazole
2,5-di(1-methyl-1-ethylpropyl)-4-(1,1-dimethylhexyl)imidazole
2,4-di(1-methyl-1-ethylpropyl)-5-(1-methylethyl)imidazole
2,5-di(1-methyl-1-ethylpropyl)-4-(1-methylethyl)imidazole
2,4-di(1-methyl-1-ethylpropyl)-5-(1,2-dimethylpropyl)imidazole
2,5-di(1-methyl-1-ethylpropyl)-4-(1,2-dimethylpropyl)imidazole
2-tertbutyl-4,5-di(1-methylpropyl)imidazole
2-(1,1-dimethylpropyl)-4,5-di(1-methylpropyl)imidazole
2-(1,1-dimethylbutyl)-4,5-di(1-methylpropyl)imidazole
2-(1,1-dimethylpentyl)-4,5-di(1-methylpropyl)imidazole
2-(1,1-dimethylhexyl)-4,5-di(1-methylpropyl)imidazole
2-(1,1-dimethylhexyl)-4,5-di(1-methylpropyl)imidazole
2-(1-methylethyl)-4,5-di(1-methylpropyl)imidazole
2,4,5-tri(1-methylpropyl)imidazole
2,4-di-ter-butyl-5-(1-methylpropyl)imidazole
2,5-di-ter-butyl-4-(1-methylpropyl)imidazole
2-tert-butyl-4-(1,1-dimethylpropyl)-5-(1-methylpropyl)imidazole
2-tert-butyl-5-(1,1-dimethylpropyl)-4-(1-methylpropyl)imidazole
2-tert-butyl-4-(1,1-dimethylbutyl)-5-(1-methylpropyl)imidazole
2-tert-butyl-5-(1,1-dimethylbutyl)-4-(1-methylpropyl)imidazole
2-tert-butyl-4-(1,1-dimethylpentyl)-5-(1-methylpropyl)imidazole
2-tert-butyl-5-(1,1-dimethylpentyl)-4-(1-methylpropyl)imidazole
2-tert-butyl-4-(1,1-dimethylhexyl)-5-(1-methylpropyl)imidazole
2-tert-butyl-5-(1,1-dimethylhexyl)-4-(1-methylpropyl)imidazole
2-tert-butyl-4-(1-methylpropyl)-5-(1-methylpropyl)imidazole
2-tert-butyl-5-(1-methylpropyl)-4-(1-methylpropyl)imidazole
2-tert-butyl-4-(1,2-dimethylpropyl)-5-(1-methylpropyl)imidazole
2-tert-butyl-5-(1,2-dimethylpropyl)-4-(1-methylpropyl)imidazole
2-(1,1-dimethylpropyl)-4-tert-butyl-5-(1-methylpropyl)imidazole
2-(1,1-dimethylpropyl)-5-tert-butyl-4-(1-methylpropyl)imidazole
2,4-(1,1-dimethylpropyl)-5-(1-methylpropyl)imidazole
2-(1,1-dimethylpropyl)-4-(1,1-dimethylbutyl)-5-(1-methylpropyl)imidazole
2-(1,1-dimethylpropyl)-5-(1,1-dimethylbutyl)-4-(1-methylpropyl)imidazole
2-(1,1-dimethylpropyl)-4-(1,1-dimethylpentyl)-5-(1-methylpropyl)imidazole
2-(1,1-dimethylpropyl)-5-(1,1-dimethylpentyl)-4-(1-methylpropyl)imidazole
2-(1,1-dimethylpropyl)-4-(1,1-dimethylhexyl)-5-(1-methylpropyl)imidazole
2-(1,1-dimethylpropyl)-5-(1,1-dimethylhexyl)-4-(1-methylpropyl)imidazole
2-(1,1-dimethylpropyl)-4-(1-methylethyl)-5-(1-methylpropyl)imidazole
2-(1,1-dimethylpropyl)-5-(1-methylethyl)-4-(1-methylpropyl)imidazole
2-(1,1-dimethylpropyl)-4-(1,2-dimethylpropyl)-5-(1-methylpropyl)imidazole
2-(1,1-dimethylpropyl)-5-(1,1-dimethylpropyl)-4-(1-methylpropyl)imidazole
2-(1,1-dimethylbutyl)-4-tert-butyl-5-(1-methylpropyl)imidazole
2-(1,1-dimethylbutyl)-5-tert-butyl-4-(1-methylpropyl)imidazole
2-(1,1-dimethylbutyl)-4-(1,1-dimethylpropyl)-5-(1-methylpropyl)imidazole
2-(1,1-dimethylbutyl)-5-(1,1-dimethylpropyl)-4-(1-methylpropyl)imidazole
2,4-di(1,1-dimethylbutyl)-5-(1-methylpropyl)imidazole
2,5-di(1,1-dimethylbutyl)-4-(1-methylpropyl)imidazole
2-(1,1-dimethylbutyl)-4-(1,1-dimethylpentyl)-5-(1-methylpropyl)imidazole
2-(1,1-dimethylbutyl)-5-(1,1-dimethylpentyl)-4-(1-methylpropyl)imidazole
2-(1,1-dimethylbutyl)-4-(1,1-dimethylhexyl)-5-(1-methylpropyl)imidazole
2-(1,1-dimethylbutyl)-5-(1,1-dimethylhexyl)-4-(1-methylpropyl)imidazole
2-(1,1-dimethylbutyl)-4-(1-methylethyl)-5-(1-methylpropyl)imidazole
2-(1,1-dimethylbutyl)-5-(1-methylethyl)-4-(1-methylpropyl)imidazole 2-(1,1-dimethylbutyl)-4-(1,2-dimethylpropyl)-5-(1-methylpropyl)imidazole
2-(1,1-dimethylbutyl)-5-(1,2-dimethylpropyl)-4-(1-methylpropyl)imidazole
2-(1,1-dimethylpentyl)-4-tert-butyl-5-(1-methylpropyl)imidazole
2-(1,1-dimethylpentyl)-5-tert-butyl-4-(1-methylpropyl)imidazole
2-(1,1-dimethylpentyl)-4-(1,1-dimethylpropyl)-5-(1-methylpropyl)imidazole
2-(1,1-dimethylpentyl)-5-(1,1-dimethylpropyl)-4-(1-methylpropyl)imidazole
2-(1,1-dimethylpentyl)-4-(1,1-dimethylbutyl)-5-(1-methylpropyl)imidazole
2-(1,1-dimethylpentyl)-5-(1,1-dimethylbutyl)-4-(1-methylpropyl)imidazole
2-4-di(1,1-dimethylpentyl)-5-(1-methylpropyl)imidazole
2-5-di(1,1-dimethylpentyl)-4-(1-methylpropyl)imidazole
2-(1,1-dimethylpentyl)-4-(1,1-dimethylhexyl)-5-(1-methylpropyl)imidazole
2-(1,1-dimethylpentyl)-5-(1,1-dimethylhexyl)-4-(1-methylpropyl)imidazole
2-(1,1-dimethylpentyl)-4-(1-methylethyl)-5-(1-methylpropyl)imidazole
2-(1,1-dimethylpentyl)-5-(1-methylethyl)-4-(1-methylpropyl)imidazole
2-(1,1-dimethylpentyl)-4-(1,2-dimethylpropyl)-5-(1-methylpropyl)imidazole
2-(1,1-dimethylpentyl)-5-(1,2-dimethylpropyl)-4-(1-methylpropyl)imidazole
2-(1,1-dimethylhexyl)-4-tert-butyl-5-(1-methylpropyl)imidazole
2-(1,1-dimethylhexyl)-5-tert-butyl-4-(1-methylpropyl)imidazole
2-(1,1-dimethylhexyl)-4-(1,1-dimethylpropyl)-5-(1-methylpropyl)imidazole
2-(1,1-dimethylhexyl)-5-(1,1-dimethylpropyl)-4-(1-methylpropyl)imidazole
2-(1,1-dimethylhexyl)-4-(1,1-dimethylbutyl)-5-(1-methylpropyl)imidazole
2-(1,1-dimethylhexyl)-5-(1,1-dimethylbutyl)-4-(1-methylpropyl)imidazole
2-(1,1-dimethylhexyl)-4-(1,1-dimethylpentyl)-5-(1-methylpropyl)imidazole
2-(1,1-dimethylhexyl)-5-(1,1-dimethylpentyl)-4-(1-methylpropyl)imidazole
2,4-(1,1-dimethylhexyl)-5-(1-methylpropyl)imidazole
2,5-(1,1-dimethylhexyl)-4-(1-methylpropyl)imidazole
2-(1,1-dimethylhexyl)-4-(1-methylethyl)-5-(1-methylpropyl)imidazole
2-(1,1-dimethylhexyl)-5-(1-methylethyl)-4-(1-methylpropyl)imidazole
2-(1,1-dimethylhexyl)-4-(1,2-dimethylpropyl)-5-(1-methylpropyl)imidazole
2-(1,1-dimethylhexyl)-5-(1,2-dimethylpropyl)-4-(1-methylpropyl)imidazole
2-(1-methylethyl)-4-tert-butyl-5-(1-methylpropyl)imidazole
2-(1-methylethyl)-5-tert-butyl-4-(1-methylpropyl)imidazole
2-(1-methylethyl)-4-(1,1-dimethylpropyl)-5-(1-methylpropyl)imidazole
2-(1-methylethyl)-5-(1,1-dimethylpropyl)-4-(1-methylpropyl)imidazole
2-(1-methylethyl)-4-(1,1-dimethylbutyl)-5-(1-methylpropyl)imidazole
2-(1-methylethyl)-5-(1,1-dimethylbutyl)-4-(1-methylpropyl)imidazole
2-(1-methylethyl)-4-(1,1-dimethylpentyl)-5-(1-methylpropyl)imidazole
2-(1-methylethyl)-5-(1,1-dimethylpentyl)-4-(1-methylpropyl)imidazole
2-(1-methylethyl)-4-(1,1-dimethylhexyl)-5-(1-methylpropyl)imidazole
2-(1-methylethyl)-5-(1,1-dimethylhexyl)-4-(1-methylpropyl)imidazole
2,4-di(1-methylethyl)-5-(1-methylpropyl)imidazole
2,5-di(1-methylethyl)-4-(1-methylpropyl)imidazole
2-(1-methylethyl)-4-(1,2-dimethylpropyl)-5-(1-methylpropyl)imidazole
2-(1-methylethyl)-5-(1,2-dimethylpropyl)-4-(1-methylpropyl)imidazole
2-(1,2-dimethylpropyl)-4-tert-butyl-5-(1-methylpropyl)imidazole
2-(1,2-dimethylpropyl)-5-tert-butyl-4-(1-methylpropyl)imidazole
2-(1,2-dimethylpropyl)-4-(1,1-dimethylpropyl)-5-(1-methylpropyl)imidazole
2-(1,2-dimethylpropyl)-5-(1,1-dimethylpropyl)-4-(1-methylpropyl)imidazole
2-(1,2-dimethylpropyl)-4-(1,1-dimethylbutyl)-5-(1-methylpropyl)imidazole
2-(1,2-dimethylpropyl)-5-(1,1-dimethylbutyl)-4-(1-methylpropyl)imidazole
2-(1,2-dimethylpropyl)-4-(1,1-dimethylpentyl)-5-(1-methylpropyl)imidazole
2-(1,2-dimethylpropyl)-5-(1,1-dimethylpentyl)-4-(1-methylpropyl)imidazole
2-(1,2-dimethylpropyl)-4-(1,1-dimethylhexyl)-5-(1-methylpropyl)imidazole
2-(1,2-dimethylpropyl)-5-(1,1-dimethylhexyl)-4-(1-methylpropyl)imidazole
2-(1,2-dimethylpropyl)-4-(1-methylethyl)-5-(1-methylpropyl)imidazole
2-(1,2-dimethylpropyl)-5-(1-methylethyl)-4-(1-methylpropyl)imidazole
2,4-(1,2-dimethylpropyl)-5-(1-methylpropyl)imidazole
2,5-(1,2-dimethylpropyl)-4-(1-methylpropyl)imidazole
2-(1-methylpropyl)-4-tert-butyl-5-(1,1-dimethylpropyl)imidazole
2-(1-methylpropyl)-5-tert-butyl-4-(1,1-dimethylpropyl)imidazole
2-(1-methylpropyl)-4-tert-butyl-5-(1,1-dimethylbutyl)imidazole
2-(1-methylpropyl)-5-tert-butyl-4-(1,1-dimethylbutyl)imidazole
2-(1-methylpropyl)-4-tert-butyl-5-(1,1-dimethylpentyl)imidazole
2-(1-methylpropyl)-5-tert-butyl-4-(1,1-dimethylpentyl)imidazole
2-(1-methylpropyl)-4-tert-butyl-5-(1,1-dimethylhexyl)imidazole
2-(1-methylpropyl)-5-tert-butyl-4-(1,1-dimethylhexyl)imidazole
2-(1-methylpropyl)-4-(1,1-dimethylpropyl)-5-(dimethylbutyl)imidazole
2-(1-methylpropyl)-4-(1,1-dimethylpropyl)-5-(dimethylbutyl)imidazole
2-(1-methylpropyl)-4-(1,1-dimethylpropyl)-5-(dimethylpentyl)imidazole
2-(1-methylpropyl)-4-(1,1-dimethylpropyl)-5-(dimethylpentyl)imidazole
2-(1-methylpropyl)-4-(1,1-dimethylpropyl)-5-(dimethylhexyl)imidazole 2-(1-methylpropyl)-4-(1,1-dimethylpropyl)-5-(dimethylhexyl)imidazole
2-(1-methylpropyl)-4-(dimethylpentyl)-5-(1,1-dimethylbutyl)imidazole
2-(1-methylpropyl)-5-(dimethylpentyl)-4-(1,1-dimethylbutyl)imidazole
2-(1-methylpropyl)-4-(dimethylpentyl)-5-(1,1-dimethylhexyl)imidazole
2-(1-methylpropyl)-5-(dimethylpentyl)-4-(1,1-dimethylhexyl)imidazole
2-(1-methylpropyl)-4-tert-butyl-5-(1-methylethyl)imidazole
2-(1-methylpropyl)-5-tert-butyl-4-(1-methylethyl)imidazole
2-(1-methylpropyl)-4-(1,1-dimethylpropyl)-5-(1-methylethyl)imidazole
2-(1-methylpropyl)-5-(1,1-dimethylpropyl)-4-(1-methylethyl)imidazole
2-(1-methylpropyl)-4-(1,1-dimethylbutyl)-5-(1-methylethyl)imidazole
2-(1-methylpropyl)-5-(1,1-dimethylbutyl)-4-(1-methylethyl)imidazole
2-(1-methylpropyl)-4-(1,1-dimethylpentyl)-5-(1-methylethyl)imidazole
2-(1-methylpropyl)-5-(1,1-dimethylpentyl)-4-(1-methylethyl)imidazole
2-(1-methylpropyl)-4-(1,1-dimethylhexyl)-5-(1-methylethyl)imidazole
2-(1-methylpropyl)-5-(1,1-dimethylhexyl)-4-(1-methylethyl)imidazole
2-(1-methylpropyl)-4-tert-butyl-5-(1,2-dimethylpropyl)imidazole
2-(1-methylpropyl)-5-tert-butyl-4-(1,2-dimethylpropyl)imidazole
2-(1-methylpropyl)-4-tert-butyl-5-(1,2-dimethylpropyl)imidazole
2-(1-methylpropyl)-4-(1,1-dimethylpropyl)-5-(1,2-dimethylpropyl)imidazole
2-(1-methylpropyl)-5-(1,1-dimethylpropyl)-4-(1,2-dimethylpropyl)imidazole
2-(1-methylpropyl)-4-(1,1-dimethylbutyl)-5-(1,2-dimethylpropyl)imidazole
2-(1-methylpropyl)-5-(1,1-dimethylbutyl)-4-(1,2-dimethylpropyl)imidazole
2-(1-methylpropyl)-4-(1,1-dimethylpentyl)-5-(1,2-dimethylpropyl)imidazole
2-(1-methylpropyl)-5-(1,1-dimethylpentyl)-4-(1,2-dimethylpropyl)imidazole
2-(1-methylpropyl)-4-(1,1-dimethylhexyl)-5-(1,2-dimethylpropyl)imidazole
2-(1-methylpropyl)-5-(1,1-dimethylhexyl)-4-(1,2-dimethylpropyl)imidazole
2-(1-methylpropyl)-4-(1-methylethyl)-5-(1,2-dimethylpropyl)imidazole
2-(1-methylpropyl)-5-(1-methylethyl)-4-(1,2-dimethylpropyl)imidazole
2,4-di(1-methylpropyl)-5-tert-butylimidazole
2,5-di(1-methylpropyl)-4-tert-butylimidazole
2,4-di(1-methylpropyl)-5-(1,1-dimethylpropyl)imidazole
2,5-di(1-methylpropyl)-4-(1,1-dimethylpropyl)imidazole
2,4-di(1-methylpropyl)-5-(1,1-dimethylbutyl)imidazole
2,5-di(1-methylpropyl)-4-(1,1-dimethylbutyl)imidazole
2,4-di(1-methylpropyl)-5-(1,1-dimethylpentyl)imidazole
2,5-di(1-methylpropyl)-4-(1,1-dimethylpentyl)imidazole
2,4-di(1-methylpropyl)-5-(1,1-dimethylhexyl)imidazole
2,5-di(1-methylpropyl)-4-(1,1-dimethylhexyl)imidazole
2,4-di(1-methylpropyl)-5-(1-methylethyl)imidazole
2,5-di(1-methylpropyl)-4-(1-methylethyl)imidazole
2,4-di(1-methylpropyl)-5-(1,2-dimethylpropyl)imidazole
2,5-di(1-methylpropyl)-4-(1,2-dimethylpropyl)imidazole
2-tertbutyl-4,5-di(1-methylbutyl)imidazole
2-(1,1-dimethylpropyl)-4,5-di(1-methylbutyl)imidazole
2-(1,1-dimethylbutyl)-4,5-di(1-methylbutyl)imidazole
2-(1,1-dimethylpentyl)-4,5-di(1-methylbutyl)imidazole
2-(1,1-dimethylhexyl)-4,5-di(1-methylbutyl)imidazole
2-(1,1-dimethylhexyl)-4,5-di(1-methylbutyl)imidazole
2-(1-methylethyl)-4,5-di(1-methylbutyl)imidazole
2,4,5-tri(1-methylbutyl)imidazole
2,4-di-ter-butyl-5-(1-methylbutyl)imidazole
2,5-di-ter-butyl-4-(1-methylbutyl)imidazole
2-tert-butyl-4-(1,1-dimethylpropyl)-5-(1-methylbutyl)imidazole
2-tert-butyl-5-(1,1-dimethylpropyl)-4-(1-methylbutyl)imidazole
2-tert-butyl-4-(1,1-dimethylbutyl)-5-(1-methylbutyl)imidazole
2-tert-butyl-5-(1,1-dimethylbutyl)-4-(1-methylbutyl)imidazole
2-tert-butyl-4-(1,1-dimethylpentyl)-5-(1-methylbutyl)imidazole
2-tert-butyl-5-(1,1-dimethylpentyl)-4-(1-methylbutyl)imidazole
2-tert-butyl-4-(1,1-dimethylhexyl)-5-(1-methylbutyl)imidazole
2-tert-butyl-5-(1,1-dimethylhexyl)-4-(1-methylbutyl)imidazole
2-tert-butyl-4-(1-methylbutyl)-5-(1-methylbutyl)imidazole
2-tert-butyl-5-(1-methylbutyl)-4-(1-methylbutyl)imidazole
2-tert-butyl-4-(1,2-dimethylpropyl)-5-(1-methylbutyl)imidazole
2-tert-butyl-5-(1,2-dimethylpropyl)-4-(1-methylbutyl)imidazole
2-(1,1-dimethylpropyl)-4-tert-butyl-5-(1-methylbutyl)imidazole
2-(1,1-dimethylpropyl)-5-tert-butyl-4-(1-methylbutyl)imidazole
2,4-(1,1-dimethylpropyl)-5-(1-methylbutyl)imidazole
2-(1,1-dimethylpropyl)-4-(1,1-dimethylbutyl)-5-(1-methylbutyl)imidazole
2-(1,1-dimethylpropyl)-5-(1,1-dimethylbutyl)-4-(1-methylbutyl)imidazole
2-(1,1-dimethylpropyl)-4-(1,1-dimethylpentyl)-5-(1-methylbutyl)imidazole
2-(1,1-dimethylpropyl)-5-(1,1-dimethylpentyl)-4-(1-methylbutyl)imidazole
2-(1,1-dimethylpropyl)-4-(1,1-dimethylhexyl)-5-(1-methylbutyl)imidazole
2-(1,1-dimethylpropyl)-5-(1,1-dimethylhexyl)-4-(1-methylbutyl)imidazole
2-(1,1-dimethylpropyl)-4-(1-methylethyl)-5-(1-methylbutyl)imidazole
2-(1,1-dimethylpropyl)-5-(1-methylethyl)-4-(1-methylbutyl)imidazole
2-(1,1-dimethylpropyl)-4-(1,2-dimethylpropyl)-5-(1-methylbutyl)imidazole
2-(1,1-dimethylpropyl)-5-(1,1-dimethylpropyl)-4-(1-methylbutyl)imidazole
2-(1,1-dimethylbutyl)-4-tert-butyl-5-(1-methylbutyl)imidazole
2-(1,1-dimethylbutyl)-5-tert-butyl-4-(1-methylbutyl)imidazole
2-(1,1-dimethylbutyl)-4-(1,1-dimethylpropyl)-5-(1-methylbutyl)imidazole
2-(1,1-dimethylbutyl)-5-(1,1-dimethylpropyl)-4-(1-methylbutyl)imidazole
2,4-di(1,1-dimethylbutyl)-5-(1-methylbutyl)imidazole 2,5-di(1,1-dimethylbutyl)-4-(1-methylbutyl)imidazole
2-(1,1-dimethylbutyl)-4-(1,1-dimethylpentyl)-5-(1-methylbutyl)imidazole
2-(1,1-dimethylbutyl)-5-(1,1-dimethylpentyl)-4-(1-methylbutyl)imidazole
2-(1,1-dimethylbutyl)-4-(1,1-dimethylhexyl)-5-(1-methylbutyl)imidazole
2-(1,1-dimethylbutyl)-5-(1,1-dimethylhexyl)-4-(1-methylbutyl)imidazole
2-(1,1-dimethylbutyl)-4-(1-methylethyl)-5-(1-methylbutyl)imidazole
2-(1,1-dimethylbutyl)-5-(1-methylethyl)-4-(1-methylbutyl)imidazole
2-(1,1-dimethylbutyl)-4-(1,2-dimethylpropyl)-5-(1-methylbutyl)imidazole
2-(1,1-dimethylbutyl)-5-(1,2-dimethylpropyl)-4-(1-methylbutyl)imidazole
2-(1,1-dimethylpentyl)-4-tert-butyl-5-(1-methylbutyl)imidazole
2-(1,1-dimethylpentyl)-5-tert-butyl-4-(1-methylbutyl)imidazole
2-(1,1-dimethylpentyl)-4-(1,1-dimethylpropyl)-5-(1-methylbutyl)imidazole
2-(1,1-dimethylpentyl)-5-(1,1-dimethylpropyl)-4-(1-methylbutyl)imidazole
2-(1,1-dimethylpentyl)-4-(1,1-dimethylbutyl)-5-(1-methylbutyl)imidazole
2-(1,1-dimethylpentyl)-5-(1,1-dimethylbutyl)-4-(1-methylbutyl)imidazole
2-4-di(1,1-dimethylpentyl)-5-(1-methylbutyl)imidazole
2-5-di(1,1-dimethylpentyl)-4-(1-methylbutyl)imidazole
2-(1,1-dimethylpentyl)-4-(1,1-dimethylhexyl)-5-(1-methylbutyl)imidazole
2-(1,1-dimethylpentyl)-5-(1,1-dimethylhexyl)-4-(1-methylbutyl)imidazole
2-(1,1-dimethylpentyl)-4-(1-methylethyl)-5-(1-methylbutyl)imidazole
2-(1,1-dimethylpentyl)-5-(1-methylethyl)-4-(1-methylbutyl)imidazole
2-(1,1-dimethylpentyl)-4-(1,2-dimethylpropyl)-5-(1-methylbutyl)imidazole
2-(1,1-dimethylpentyl)-5-(1,2-dimethylpropyl)-4-(1-methylbutyl)imidazole
2-(1,1-dimethylhexyl)-4-tert-butyl-5-(1-methylbutyl)imidazole
2-(1,1-dimethylhexyl)-5-tert-butyl-4-(1-methylbutyl)imidazole
2-(1,1-dimethylhexyl)-4-(1,1-dimethylpropyl)-5-(1-methylbutyl)imidazole
2-(1,1-dimethylhexyl)-5-(1,1-dimethylpropyl)-4-(1-methylbutyl)imidazole
2-(1,1-dimethylhexyl)-4-(1,1-dimethylbutyl)-5-(1-methylbutyl)imidazole
2-(1,1-dimethylhexyl)-5-(1,1-dimethylbutyl)-4-(1-methylbutyl)imidazole
2-(1,1-dimethylhexyl)-4-(1,1-dimethylpentyl)-5-(1-methylbutyl)imidazole
2-(1,1-dimethylhexyl)-5-(1,1-dimethylpentyl)-4-(1-methylbutyl)imidazole
2,4-(1,1-dimethylhexyl)-5-(1-methylbutyl)imidazole
2,5-(1,1-dimethylhexyl)-4-(1-methylbutyl)imidazole
2-(1,1-dimethylhexyl)-4-(1-methylethyl)-5-(1-methylbutyl)imidazole
2-(1,1-dimethylhexyl)-5-(1-methylethyl)-4-(1-methylbutyl)imidazole
2-(1,1-dimethylhexyl)-4-(1,2-dimethylpropyl)-5-(1-methylbutyl)imidazole
2-(1,1-dimethylhexyl)-5-(1,2-dimethylpropyl)-4-(1-methylbutyl)imidazole
2-(1-methylethyl)-4-tert-butyl-5-(1-methylbutyl)imidazole
2-(1-methylethyl)-5-tert-butyl-4-(1-methylbutyl)imidazole
2-(1-methylethyl)-4-(1,1-dimethylpropyl)-5-(1-methylbutyl)imidazole
2-(1-methylethyl)-5-(1,1-dimethylpropyl)-4-(1-methylbutyl)imidazole
2-(1-methylethyl)-4-(1,1-dimethylbutyl)-5-(1-methylbutyl)imidazole
2-(1-methylethyl)-5-(1,1-dimethylbutyl)-4-(1-methylbutyl)imidazole
2-(1-methylethyl)-4-(1,1-dimethylpentyl)-5-(1-methylbutyl)imidazole
2-(1-methylethyl)-5-(1,1-dimethylpentyl)-4-(1-methylbutyl)imidazole
2-(1-methylethyl)-4-(1,1-dimethylhexyl)-5-(1-methylbutyl)imidazole
2-(1-methylethyl)-5-(1,1-dimethylhexyl)-4-(1-methylbutyl)imidazole
2,4-di(1-methylethyl)-5-(1-methylbutyl)imidazole
2,5-di(1-methylethyl)-4-(1-methylbutyl)imidazole
2-(1-methylethyl)-4-(1,2-dimethylpropyl)-5-(1-methylbutyl)imidazole
2-(1-methylethyl)-5-(1,2-dimethylpropyl)-4-(1-methylbutyl)imidazole
2-(1,2-dimethylpropyl)-4-tert-butyl-5-(1-methylbutyl)imidazole
2-(1,2-dimethylpropyl)-5-tert-butyl-4-(1-methylbutyl)imidazole
2-(1,2-dimethylpropyl)-4-(1,1-dimethylpropyl)-5-(1-methylbutyl)imidazole
2-(1,2-dimethylpropyl)-5-(1,1-dimethylpropyl)-4-(1-methylbutyl)imidazole
2-(1,2-dimethylpropyl)-4-(1,1-dimethylbutyl)-5-(1-methylbutyl)imidazole
2-(1,2-dimethylpropyl)-5-(1,1-dimethylbutyl)-4-(1-methylbutyl)imidazole
2-(1,2-dimethylpropyl)-4-(1,1-dimethylpentyl)-5-(1-methylbutyl)imidazole
2-(1,2-dimethylpropyl)-5-(1,1-dimethylpentyl)-4-(1-methylbutyl)imidazole
2-(1,2-dimethylpropyl)-4-(1,1-dimethylhexyl)-5-(1-methylbutyl)imidazole
2-(1,2-dimethylpropyl)-5-(1,1-dimethylhexyl)-4-(1-methylbutyl)imidazole
2-(1,2-dimethylpropyl)-4-(1-methylethyl)-5-(1-methylbutyl)imidazole
2-(1,2-dimethylpropyl)-5-(1-methylethyl)-4-(1-methylbutyl)imidazole
2,4-(1,2-dimethylpropyl)-5-(1-methylbutyl)imidazole
2,5-(1,2-dimethylpropyl)-4-(1-methylbutyl)imidazole
2-(1-methylbutyl)-4-tert-butyl-5-(1,1-dimethylpropyl)imidazole
2-(1-methylbutyl)-5-tert-butyl-4-(1,1-dimethylpropyl)imidazole
2-(1-methylbutyl)-4-tert-butyl-5-(1,1-dimethylbutyl)imidazole
2-(1-methylbutyl)-5-tert-butyl-4-(1,1-dimethylbutyl)imidazole
2-(1-methylbutyl)-4-tert-butyl-5-(1,1-dimethylpentyl)imidazole
2-(1-methylbutyl)-5-tert-butyl-4-(1,1-dimethylpentyl)imidazole
2-(1-methylbutyl)-4-tert-butyl-5-(1,1-dimethylhexyl)imidazole 2-(1-methylbutyl)-5-tert-butyl-4-(1,1-dimethylhexyl)imidazole
2-(1-methylbutyl)-4-(1,1-dimethylpropyl)-5-(dimethylbutyl)imidazole
2-(1-methylbutyl)-4-(1,1-dimethylpropyl)-5-(dimethylbutyl)imidazole
2-(1-methylbutyl)-4-(1,1-dimethylpropyl)-5-(dimethylpentyl)imidazole
2-(1-methylbutyl)-4-(1,1-dimethylpropyl)-5-(dimethylpentyl)imidazole
2-(1-methylbutyl)-4-(1,1-dimethylpropyl)-5-(dimethylhexyl)imidazole
2-(1-methylbutyl)-4-(1,1-dimethylpropyl)-5-(dimethylhexyl)imidazole
2-(1-methylbutyl)-4-(dimethylpentyl)-5-(1,1-dimethylbutyl)imidazole
2-(1-methylbutyl)-5-(dimethylpentyl)-4-(1,1-dimethylbutyl)imidazole
2-(1-methylbutyl)-4-(dimethylpentyl)-5-(1,1-dimethylhexyl)imidazole
2-(1-methylbutyl)-5-(dimethylpentyl)-4-(1,1-dimethylhexyl)imidazole
2-(1-methylbutyl)-4-tert-butyl-5-(1-methylethyl)imidazole
2-(1-methylbutyl)-5-tert-butyl-4-(1-methylethyl)imidazole
2-(1-methylbutyl)-4-(1,1-dimethylpropyl)-5-(1-methylethyl)imidazole
2-(1-methylbutyl)-5-(1,1-dimethylpropyl)-4-(1-methylethyl)imidazole
2-(1-methylbutyl)-4-(1,1-dimethylbutyl)-5-(1-methylethyl)imidazole
2-(1-methylbutyl)-5-(1,1-dimethylbutyl)-4-(1-methylethyl)imidazole
2-(1-methylbutyl)-4-(1,1-dimethylpentyl)-5-(1-methylethyl)imidazole
2-(1-methylbutyl)-5-(1,1-dimethylpentyl)-4-(1-methylethyl)imidazole
2-(1-methylbutyl)-4-(1,1-dimethylhexyl)-5-(1-methylethyl)imidazole
2-(1-methylbutyl)-5-(1,1-dimethylhexyl)-4-(1-methylethyl)imidazole
2-(1-methylbutyl)-4-tert-butyl-5-(1,2-dimethylpropyl)imidazole
2-(1-methylbutyl)-5-tert-butyl-4-(1,2-dimethylpropyl)imidazole
2-(1-methylbutyl)-4-tert-butyl-5-(1,2-dimethylpropyl)imidazole
2-(1-methylbutyl)-4-(1,1-dimethylpropyl)-5-(1,2-dimethylpropyl)imidazole
2-(1-methylbutyl)-5-(1,1-dimethylpropyl)-4-(1,2-dimethylpropyl)imidazole
2-(1-methylbutyl)-4-(1,1-dimethylbutyl)-5-(1,2-dimethylpropyl)imidazole
2-(1-methylbutyl)-5-(1,1-dimethylbutyl)-4-(1,2-dimethylpropyl)imidazole
2-(1-methylbutyl)-4-(1,1-dimethylpentyl)-5-(1,2-dimethylpropyl)imidazole
2-(1-methylbutyl)-5-(1,1-dimethylpentyl)-4-(1,2-dimethylpropyl)imidazole
2-(1-methylbutyl)-4-(1,1-dimethylhexyl)-5-(1,2-dimethylpropyl)imidazole
2-(1-methylbutyl)-5-(1,1-dimethylhexyl)-4-(1,2-dimethylpropyl)imidazole
2-(1-methylbutyl)-4-(1-methylethyl)-5-(1,2-dimethylpropyl)imidazole
2-(1-methylbutyl)-5-(1-methylethyl)-4-(1,2-dimethylpropyl)imidazole
2,4-di(1-methylbutyl)-5-tert-butylimidazole
2,5-di(1-methylbutyl)-4-tert-butylimidazole
2,4-di(1-methylbutyl)-5-(1,1-dimethylpropyl)imidazole
2,5-di(1-methylbutyl)-4-(1,1-dimethylpropyl)imidazole
2,4-di(1-methylbutyl)-5-(1,1-dimethylbutyl)imidazole
2,5-di(1-methylbutyl)-4-(1,1-dimethylbutyl)imidazole
2,4-di(1-methylbutyl)-5-(1,1-dimethylpentyl)imidazole
2,5-di(1-methylbutyl)-4-(1,1-dimethylpentyl)imidazole
2,4-di(1-methylbutyl)-5-(1,1-dimethylhexyl)imidazole
2,5-di(1-methylbutyl)-4-(1,1-dimethylhexyl)imidazole
2,4-di(1-methylbutyl)-5-(1-methylethyl)imidazole
2,5-di(1-methylbutyl)-4-(1-methylethyl)imidazole
2,4-di(1-methylbutyl)-5-(1,2-dimethylpropyl)imidazole
2,5-di(1-methylbutyl)-4-(1,2-dimethylpropyl)imidazole More preferably, the imidazole is one of:

2-tertbutyl-4,5-di(1-methyl-1-ethylpropyl)imidazole
2-(1,1-dimethylpropyl)-4,5-di(1-methyl-1-ethylpropyl)imidazole
2-(1,1-dimethylbutyl)-4,5-di(1-methyl-1-ethylpropyl)imidazole
2-(1,1-dimethylpentyl)-4,5-di(1-methyl-1-ethylpropyl)imidazole
2-(1,1-dimethylhexyl)-4,5-di(1-methyl-1-ethylpropyl)imidazole
2-(1-methylhexyl)-4,5-di(1-methyl-1-ethylpropyl)imidazole
2-(1-methylethyl)-4,5-di(1-methyl-1-ethylpropyl)imidazole
2,4,5-tri(1-methyl-1-ethylpropyl)imidazole
2,4-di-ter-butyl-5-(1-methyl-1-ethylpropyl)imidazole
2,5-di-ter-butyl-4-(1-methyl-1-ethylpropyl)imidazole
2-tert-butyl-4-(1,1-dimethylpropyl)-5-(1-methyl-1-ethylpropyl)imidazole
2-tert-butyl-5-(1,1-dimethylpropyl)-4-(1-methyl-1-ethylpropyl)imidazole
2-tert-butyl-4-(1,1-dimethylbutyl)-5-(1-methyl-1-ethylpropyl)imidazole
2-tert-butyl-5-(1,1-dimethylbutyl)-4-(1-methyl-1-ethylpropyl)imidazole
2-tert-butyl-4-(1,1-dimethylpentyl)-5-(1-methyl-1-ethylpropyl)imidazole
2-tert-butyl-5-(1,1-dimethylpentyl)-4-(1-methyl-1-ethylpropyl)imidazole
2-tert-butyl-4-(1,1-dimethylhexyl)-5-(1-methyl-1-ethylpropyl)imidazole
2-tert-butyl-5-(1,1-dimethylhexyl)-4-(1-methyl-1-ethylpropyl)imidazole
2-(1,1-dimethylpropyl)-4-tert-butyl-5-(1-methyl-1-ethylpropyl)imidazole
2-(1,1-dimethylpropyl)-5-tert-butyl-4-(1-methyl-1-ethylpropyl)imidazole
2,4-(1,1-dimethylpropyl)-5-(1-methyl-1-ethylpropyl)imidazole
2-(1,1-dimethylpropyl)-4-(1,1-dimethylbutyl)-5-(1-methyl-1-ethylpropyl)imidazole
2-(1,1-dimethylpropyl)-5-(1,1-dimethylbutyl)-4-(1-methyl-1-ethylpropyl)imidazole
2-(1,1-dimethylpropyl)-4-(1,1-dimethylpentyl)-5-(1-methyl-1-ethylpropyl)imidazole
2-(1,1-dimethylpropyl)-5-(1,1-dimethylpentyl)-4-(1-methyl-1-ethylpropyl)imidazole
2-(1,1-dimethylpropyl)-4-(1,1-dimethylhexyl)-5-(1-methyl-1-ethylpropyl)imidazole
2-(1,1-dimethylpropyl)-5-(1,1-dimethylhexyl)-4-(1-methyl-1-ethylpropyl)imidazole
2-(1,1-dimethylpropyl)-4-(1-methylethyl)-5-(1-methyl-1-ethylpropyl)imidazole
2-(1,1-dimethylpropyl)-5-(1-methylethyl)-4-(1-methyl-1-ethylpropyl)imidazole 2-(1,1-dimethylpropyl)-4-(1,2-dimethylpropyl)-5-(1-methyl-1-ethylpropyl)imidazole
2-(1,1-dimethylpropyl)-5-(1,1-dimethylpropyl)-4-(1-methyl-1-ethylpropyl)imidazole
2-(1,1-dimethylbutyl)-4-tert-butyl-5-(1-methyl-1-ethylpropyl)imidazole
2-(1,1-dimethylbutyl)-5-tert-butyl-4-(1-methyl-1-ethylpropyl)imidazole
2-(1,1-dimethylbutyl)-4-(1,1-dimethylpropyl)-5-(1-methyl-1-ethylpropyl)imidazole
2-(1,1-dimethylbutyl)-5-(1,1-dimethylpropyl)-4-(1-methyl-1-ethylpropyl)imidazole
2,4-di(1,1-dimethylbutyl)-5-(1-methyl-1-ethylpropyl)imidazole
2,5-di(1,1-dimethylbutyl)-4-(1-methyl-1-ethylpropyl)imidazole
2-(1,1-dimethylbutyl)-4-(1,1-dimethylpentyl)-5-(1-methyl-1-ethylpropyl)imidazole
2-(1,1-dimethylbutyl)-5-(1,1-dimethylpentyl)-4-(1-methyl-1-ethylpropyl)imidazole
2-(1,1-dimethylbutyl)-4-(1,1-dimethylhexyl)-5-(1-methyl-1-ethylpropyl)imidazole
2-(1,1-dimethylbutyl)-5-(1,1-dimethylhexyl)-4-(1-methyl-1-ethylpropyl)imidazole
2-(1,1-dimethylpentyl)-4-tert-butyl-5-(1-methyl-1-ethylpropyl)imidazole
2-(1,1-dimethylpentyl)-5-tert-butyl-4-(1-methyl-1-ethylpropyl)imidazole
2-(1,1-dimethylpentyl)-4-(1,1-dimethylpropyl)-5-(1-methyl-1-ethylpropyl)imidazole
2-(1,1-dimethylpentyl)-5-(1,1-dimethylpropyl)-4-(1-methyl-1-ethylpropyl)imidazole
2-(1,1-dimethylpentyl)-4-(1,1-dimethylbutyl)-5-(1-methyl-1-ethylpropyl)imidazole
2-(1,1-dimethylpentyl)-5-(1,1-dimethylbutyl)-4-(1-methyl-1-ethylpropyl)imidazole
2-4-di(1,1-dimethylpentyl)-5-(1-methyl-1-ethylpropyl)imidazole
2-5-di(1,1-dimethylpentyl)-4-(1-methyl-1-ethylpropyl)imidazole
2-(1,1-dimethylpentyl)-4-(1,1-dimethylhexyl)-5-(1-methyl-1-ethylpropyl)imidazole
2-(1,1-dimethylpentyl)-5-(1,1-dimethylhexyl)-4-(1-methyl-1-ethylpropyl)imidazole
2-(1,1-dimethylhexyl)-4-tert-butyl-5-(1-methyl-1-ethylpropyl)imidazole
2-(1,1-dimethylhexyl)-5-tert-butyl-4-(1-methyl-1-ethylpropyl)imidazole
2-(1,1-dimethylhexyl)-4-(1,1-dimethylpropyl)-5-(1-methyl-1-ethylpropyl)imidazole
2-(1,1-dimethylhexyl)-5-(1,1-dimethylpropyl)-4-(1-methyl-1-ethylpropyl)imidazole
2-(1,1-dimethylhexyl)-4-(1,1-dimethylbutyl)-5-(1-methyl-1-ethylpropyl)imidazole
2-(1,1-dimethylhexyl)-5-(1,1-dimethylbutyl)-4-(1-methyl-1-ethylpropyl)imidazole
2-(1,1-dimethylhexyl)-4-(1,1-dimethylpentyl)-5-(1-methyl-1-ethylpropyl)imidazole
2-(1,1-dimethylhexyl)-5-(1,1-dimethylpentyl)-4-(1-methyl-1-ethylpropyl)imidazole
2,4-(1,1-dimethylhexyl)-5-(1-methyl-1-ethylpropyl)imidazole
2,5-(1,1-dimethylhexyl)-4-(1-methyl-1-ethylpropyl)imidazole
2-(1-methyl-1-ethylpropyl)-4-tert-butyl-5-(1,1-dimethylpropyl)imidazole
2-(1-methyl-1-ethylpropyl)-5-tert-butyl-4-(1,1-dimethylpropyl)imidazole
2-(1-methyl-1-ethylpropyl)-4-tert-butyl-5-(1,1-dimethylbutyl)imidazole
2-(1-methyl-1-ethylpropyl)-5-tert-butyl-4-(1,1-dimethylbutyl)imidazole
2-(1-methyl-1-ethylpropyl)-4-tert-butyl-5-(1,1-dimethylpentyl)imidazole
2-(1-methyl-1-ethylpropyl)-5-tert-butyl-4-(1,1-dimethylpentyl)imidazole
2-(1-methyl-1-ethylpropyl)-4-tert-butyl-5-(1,1-dimethylhexyl)imidazole
2-(1-methyl-1-ethylpropyl)-5-tert-butyl-4-(1,1-dimethylhexyl)imidazole
2-(1-methyl-1-ethylpropyl)-4-(1,1-dimethylpropyl)-5-(dimethylbutyl)imidazole
2-(1-methyl-1-ethylpropyl)-4-(1,1-dimethylpropyl)-5-(dimethylbutyl)imidazole
2-(1-methyl-1-ethylpropyl)-4-(1,1-dimethylpropyl)-5-(dimethylpentyl)imidazole
2-(1-methyl-1-ethylpropyl)-4-(1,1-dimethylpropyl)-5-(dimethylpentyl)imidazole
2-(1-methyl-1-ethylpropyl)-4-(1,1-dimethylpropyl)-5-(dimethylhexyl)imidazole
2-(1-methyl-1-ethylpropyl)-4-(1,1-dimethylpropyl)-5-(dimethylhexyl)imidazole
2-(1-methyl-1-ethylpropyl)-4-(dimethylpentyl)-5-(1,1-dimethylbutyl)imidazole
2-(1-methyl-1-ethylpropyl)-5-(dimethylpentyl)-4-(1,1-dimethylbutyl)imidazole
2-(1-methyl-1-ethylpropyl)-4-(dimethylpentyl)-5-(1,1-dimethylhexyl)imidazole
2-(1-methyl-1-ethylpropyl)-5-(dimethylpentyl)-4-(1,1-dimethylhexyl)imidazole
2,4-di(1-methyl-1-ethylpropyl)-5-tert-butylimidazole
2,5-di(1-methyl-1-ethylpropyl)-4-tert-butylimidazole
2,4-di(1-methyl-1-ethylpropyl)-5-(1,1-dimethylpropyl)imidazole
2,5-di(1-methyl-1-ethylpropyl)-4-(1,1-dimethylpropyl)imidazole
2,4-di(1-methyl-1-ethylpropyl)-5-(1,1-dimethylbutyl)imidazole
2,5-di(1-methyl-1-ethylpropyl)-4-(1,1-dimethylbutyl)imidazole
2,4-di(1-methyl-1-ethylpropyl)-5-(1,1-dimethylpentyl)imidazole
2,5-di(1-methyl-1-ethylpropyl)-4-(1,1-dimethylpentyl)imidazole
2,4-di(1-methyl-1-ethylpropyl)-5-(1,1-dimethylhexyl)imidazole
2,5-di(1-methyl-1-ethylpropyl)-4-(1,1-dimethylhexyl)imidazole Preferably, the imidazole is 2-tert-butyl-4,5-di-tert-amylimidazole.

Preferably, the imidazole is 2-tert-amyl-4,5-di-tert-butylimidazole.

Preferably, the imidazole is 2-tert-butyl-4-tert-amyl-5-tert-butylimidazole.

Preferably, the imidazole is 2-tert-amyl-4-tert-butyl-5-tert-amylimidazole.

Preferably, the imidazole is 2,4,5-trimethylimidazole.

Preferably, the imidazole is 2-tert-butyl-4-methyl-5-ethylimidazole.

Preferably, the imidazole is 2-ethyl-4-methylimidazole.

Preferably, the imidazole is 2-isopropyl-4,5-di(1,1-dimethylpropyl)imidazole.

Preferably, the imidazole is 2-sec-butyl-4,5-di-tert-butyl-imidazole.

Preferably, the imidazole is 2-(1-ethyl-propyl)-4,5-di-isopropylimidazole.

Preferably, the imidazole is 2-tert-butyl-4,5-di-isopropylimidazole.

For the purpose of this invention methyl is —CH$_3$ and abbreviated as Me, ethyl is —CH$_2$CH$_3$ and abbreviated as Et, isopropyl is —CH(CH$_3$)$_2$ and abbreviated as $^i$Pr, tert-butyl is —C(CH$_3$)$_3$ and abbreviated as $^t$Bu, tert-amyl is 1,1-dimethylpropyl, —C(CH$_3$)$_2$CH$_2$CH$_3$ and abbreviated as $^t$Am.

Structures A, B, C, D, E, F and G below illustrate novel imidazolate compounds based upon these imidazoles.

In one embodiment, the present invention provides a metal compound represented by Structure A:

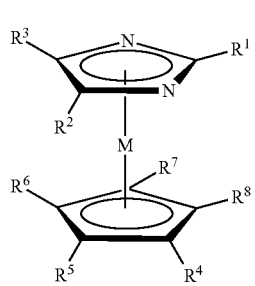

Structure A wherein M is a metal selected from Group 8 to 16, including: Fe, Co, Ni, Ru, Rh, Pd, Os, Ir, Pt, Cu, Zn, In, Ge, Sn, Sb, Te, Bi; R$^1$ can be same or different selected from group consisting of linear or branched C$_{1-10}$ alkyls, C$_{1-10}$ alkoxyalkyl, C$_{1-10}$ aminoalkyl; R$^{2-3}$ are same or different selected from group consisting of hydrogen, methyl, ethyl, n-propyl, iso-propyl, n-butyl, iso-butyl, sec-butyl, tert-butyl, isomers of pentyl; R$^{4-8}$ can be same or different selected from group consisting of hydrogen, linear or branched C$_{1-10}$ alkyls, C$_{1-10}$ alkoxyalkyl, C$_{1-10}$ aminoalkyl, Representative examples of Structure A include, but are not limited to:

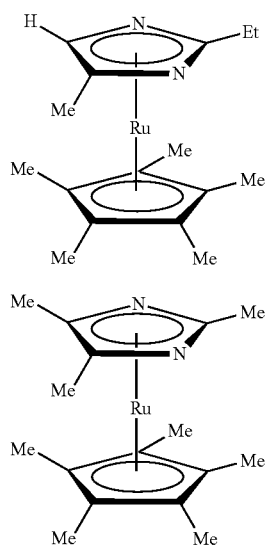

(i)

(ii)

-continued (iii)

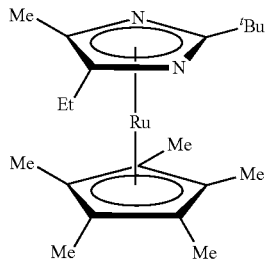

(iv)

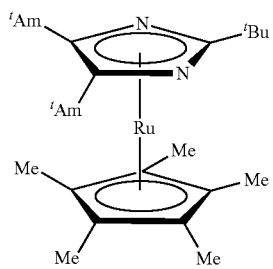

(v)

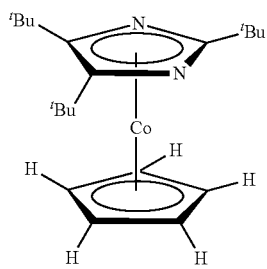

(vi)

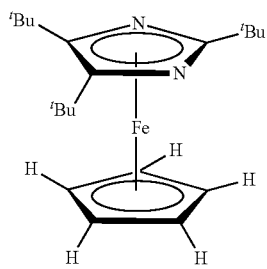

(vii)

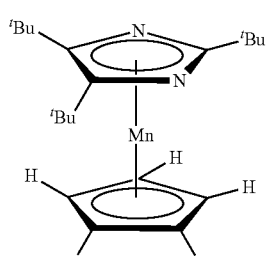

(viii)

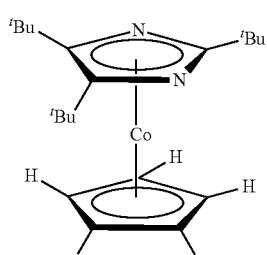

In another aspect, the present invention provides a metal compound represented by Structure B:

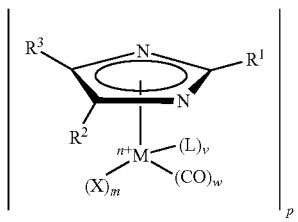

Structure B wherein M is a metal selected from Group 4 to 16, including: Mn, Fe, Co, Ni, Ru, Rh, Pd, Os, Ir, Pt, Cu, Zn, In, Ge, Sn, Sb, Te, Bi; (n)=1, 2; $R^1$ can be same or different selected from group consisting of linear or branched $C_{1-10}$ alkyls, $C_{1-10}$ alkoxyalkyl, $C_{1-10}$ aminoalkyl; $R^{2-3}$ can be same or different selected from group consisting of hydrogen, linear or branched $C_{1-10}$ alkyls, $C_{1-10}$ alkoxyalkyl, $C_{1-10}$ aminoalkyl; (L) is a neutral coordinating ligand selected from ether, polyether, furans, amine, polyamine or alkoxyamine, pyridine, N-methylimidazole, olefin, diolefin, triolefin or polyolefin, alkyne, silylolefin, silyalkyne carbon monoxide, nitrile, isonitrile, silylnitrile or isocyanide, alkyl phosphine, and aromatic phosphine; (v) is 1-4; (X) is a mono anion selected from the group consisting of $C_{1-10}$ alkyls, $C_{1-10}$ alkoxyalkyl, $C_{1-10}$ aminoalkyl, halides; alkoxy, hydride, amide, beta-diketonates, acetates, ketoiminates, diimines, alkoxides, amides, beta-ketoesters, amidinates, guanidinates, cyclopentadienyl, cyanide, isocyanide, pyrrolyl, formate, acetate, cyanate, oxalate, malonate, phenoxide, thiolate, trialkylsiloxide, bis(trialkylsilyl)amide, sulfide, nitrate, alkyl, silylalkyl, fluoroalkyl, aryl, hydride, pyrrolyl, and halide; m=0, 1; n=1, 2; (w)=2, 3; p=1, 2; such as:

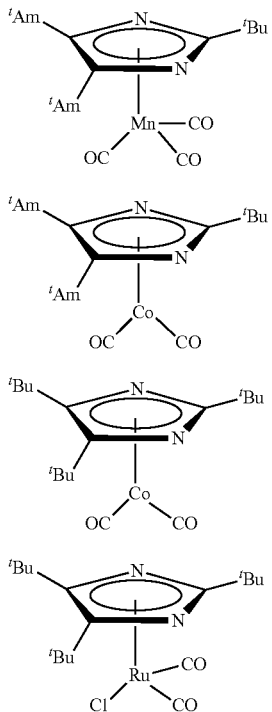

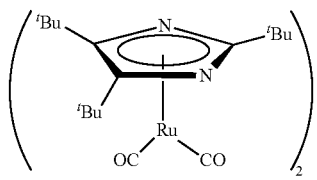

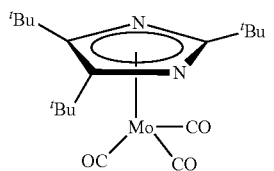

In another aspect, the present invention provides a metal compound represented by Structure C:

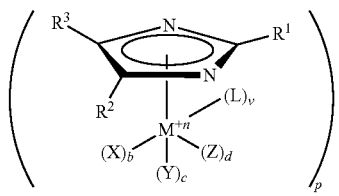

Structure C wherein M is a metal selected from Group 4 to 16, including; Ti, Zr, Hf, V, Nb, Ta, Cr, Mo, W, Al, In, Sn, Sb, Bi; (n) can be 1-6; $R^1$ can be selected from linear or branched $C_{1-10}$ alkyls, $C_{1-10}$ alkoxyalkyl, $C_{1-10}$ aminoalkyl; $R^{2-3}$ can be same or different selected from group consisting of hydrogen, linear or branched $C_{1-10}$ alkyls, $C_{1-10}$ alkoxyalkyl, $C_{1-10}$ aminoalkyl; (X), (Y) and (Z) are mono anions, which can be the same or individually different selected from alkoxy, beta-diketonates, acetates, ketoiminates, diimines, alkoxides, amides, hydrides, beta-ketoesters, amidinates, guanidinates, cyclopentadienyl, cyanide, isocyanide, pyrrolyl, formate, acetate, cyanate, oxalate, malonate, phenoxide, thiolate, trialkylsiloxide, bis(trialkylsilyl)amide, sulfide, nitrate, alkyl, silylalkyl, fluoroalkyl, aryl, hydride, pyrrolyl, and halide; exemplary alkoxy include, but not limited to; methoxy, ethoxy, n-propoxy, iso-propoxy, n-butoxy, sec-butoxy, iso-butoxy, tert-butoxy, and tert-pentoxy; exemplary amides include, but not limited to; dimethylamide, diethylamide, ethylmethylamide; (b), (c) and (d) can individually range from zero to 5, but (b)+(c)+(d)=(n)−1; (L) is a neutral coordinating ligand selected from ether, polyether, furans, amine, polyamine or alkoxyamine, pyridine, N-methylimidazole, olefin, diolefin, triolefin, polyolefin, alkyne, silylolefin, silyalkyne carbon monoxide, nitrile, isonitrile, silylnitrile, isocyanide, alkyl phosphine, aromatic phosphine; (v) is 1-4; (p)=1, 2; n=3, 4, 5, 6; p=1, 2; as illustrated by:

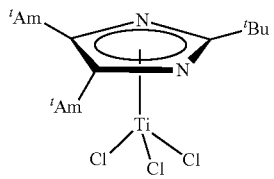

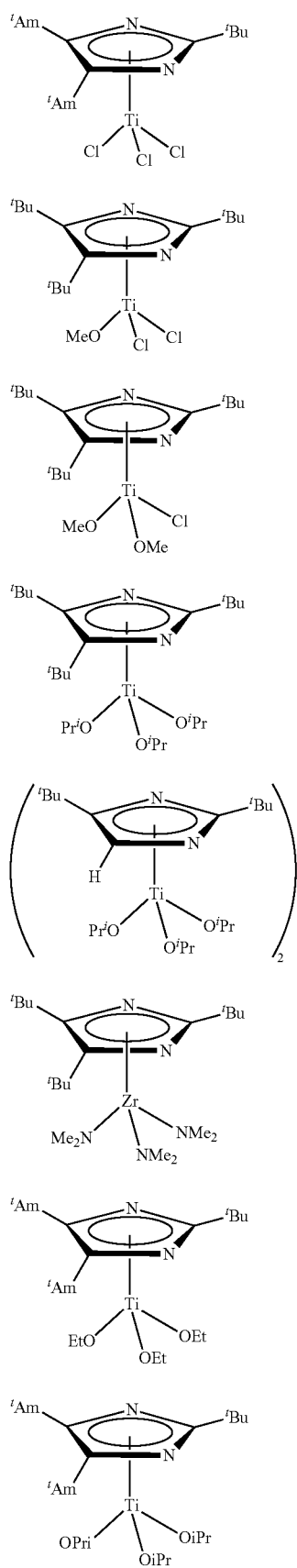

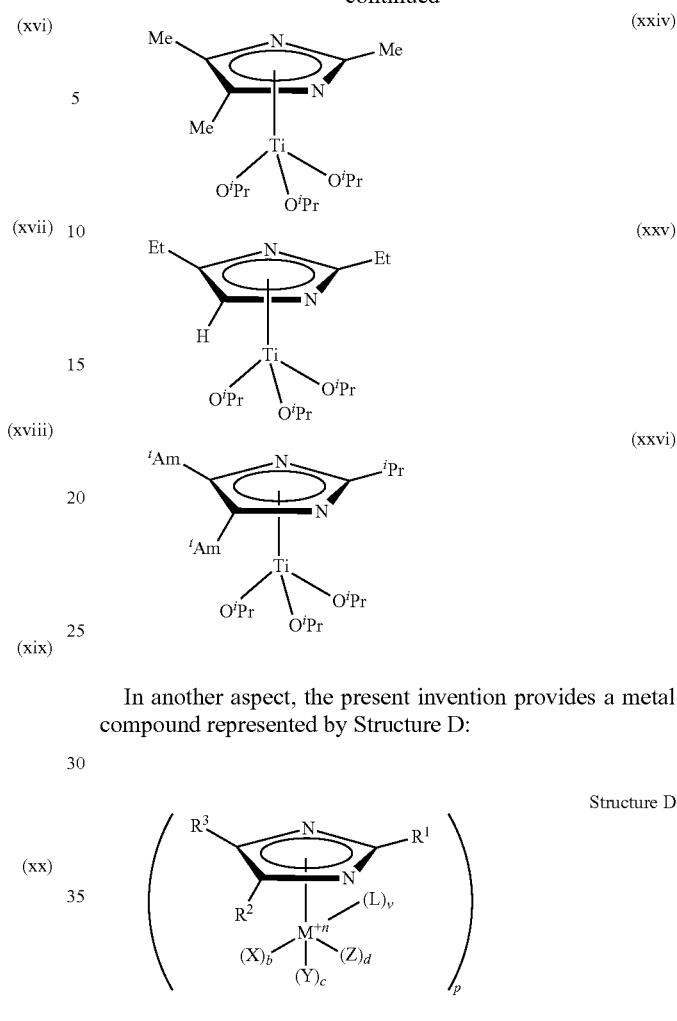

In another aspect, the present invention provides a metal compound represented by Structure D:

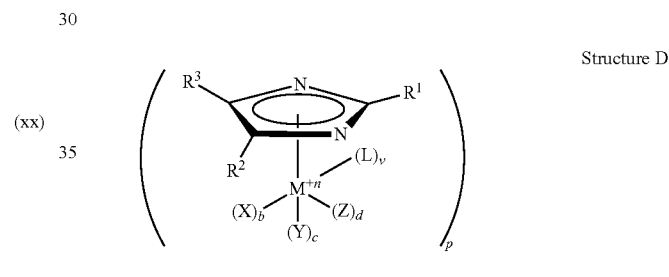

Structure D wherein M is a metal selected from the lanthanide series, including; La, Ce, Py, Nd, Pm, Sm, Eu, Gd, Tb, Dy, Ho, Er, Tm, Yb, and Lu; (n)=2, 3 or 4; $R^1$ can be selected from the group consisting of linear or branched $C_{1-10}$ alkyls, $C_{1-10}$ alkoxyalkyl, and $C_{1-10}$ aminoalkyl; $R^2$ and $R^3$ can be hydrogen, linear or branched $C_{1-10}$ alkyls, $C_{1-10}$ alkoxyalkyl, and $C_{1-10}$ aminoalkyl; (X) (Y) and (Z) are mono anions, which can be the same or individually different selected from alkoxy, beta-diketonates, acetates, ketoiminates, diimines, alkoxides, amides, hydrides, beta-ketoesters, amidinates, guanidinates, cyclopentadienyl, cyanide, isocyanide, pyrrolyl, formate, acetate, cyanate, oxalate, malonate, phenoxide, thiolate, trialkylsiloxide, bis(trialkylsilyl)amide, sulfide, nitrate, alkyl, silylalkyl, fluoroalkyl, aryl, hydride, pyrrolyl, and halide; exemplary alkoxy include, but not limited to; methoxy, ethoxy, n-propoxy, iso-propoxy, n-butoxy, sec-butoxy, iso-butoxy, tert-butoxy, and tert-pentoxy; exemplary amide include, but not limited to; dimethylamide, diethylamide, and ethylmethylamide; (b) and (c) can individually range from zero to 2, but (b)+(c)+(d)=(n)−1; (L) is a neutral coordinating ligand selected from ether, polyether, furans, amine, polyamine, alkoxyamine, pyridine, N-methylimidazole, olefin, diolefin, triolefin, polyolefin, alkyne, silylolefin, silyalkyne, carbon monoxide, nitrile, isonitrile, silylnitrile, isocyanide, alkyl phosphine, aromatic phosphine; (v) is 1-4; (p)=1, 2; as illustrated by:

(xxvii)

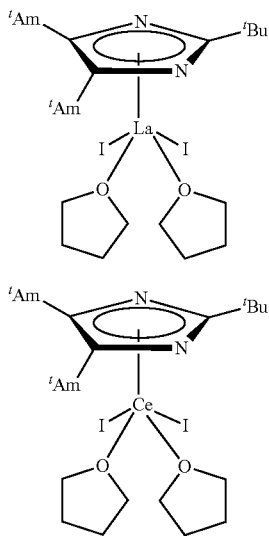

In yet another aspect, the present invention provides a metal compound represented by Structure E:

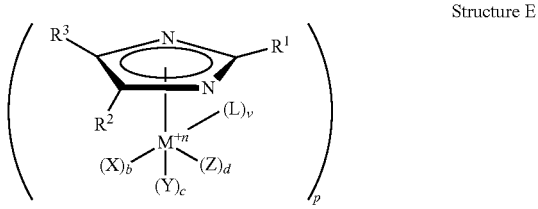

Structure E wherein M is a metal selected from the actinide series, including: Ac, Th, Pa, U, Np, Pu, Am, Cm, Bk, Cf, Es, Fm, Md, No, and Lr; (n)=2, 3, 4, 5 or 6; $R^1$ can be selected from the group consisting of linear or branched $C_{1-10}$ alkyls, $C_{1-10}$ alkoxyalkyl, and $C_{1-10}$ aminoalkyl; $R^2$ and $R^3$ can individually be hydrogen, linear or branched $C_{1-10}$ alkyls, $C_{1-10}$ alkoxyalkyl, and $C_{1-10}$ aminoalkyl; (X) (Y) and (Z) are mono anions, which can be the same or individually different, selected from; alkoxy, beta-diketonates, acetates, ketoiminates, diimines, alkoxides, amides, hydrides, beta-ketoesters, amidinates, guanidinates, cyclopentadienyl, cyanide, isocyanide, pyrrolyl, formate, acetate, cyanate, oxalate, malonate, phenoxide, thiolate, trialkylsiloxide, bis(trialkylsilyl)amide, sulfide, nitrate, alkyl, silylalkyl, fluoroalkyl, aryl, hydride, pyrrolyl, and halide; exemplary alkoxy include, but not limited to; methoxy, ethoxy, n-propoxy, iso-propoxy, n-butoxy, sec-butoxy, iso-butoxy, tert-butoxy, and tert-pentoxy; exemplary amide include, but are not limited to; dimethylamide, diethylamide, and ethylmethylamide; (b) and (c) can individually range from zero to 2, but (b)+(c)+(d)=(n)-1; (L) is a neutral coordinating ligand selected from ether, polyether, furans, amine, polyamine or alkoxyamine, pyridine, N-methylimidazole, olefin, diolefin, triolefin or polyolefin, alkyne, silylolefin, silyalkyne carbon monoxide, nitrile, isonitrile, silylnitrile or isocyanide, alkyl phosphine, and aromatic phosphine; (v) is 1-4; (p)=1, 2.

In another aspect, the present invention provides a metal compound represented by Structure F:

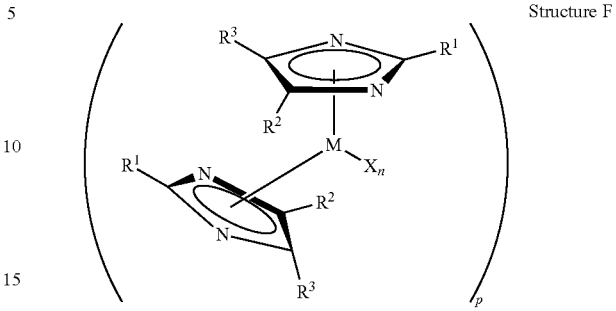

Structure F wherein M is a metal selected from Group 4 to 16, including; Fe, Co, Ni, Cr, Mn, Ru, Rh, Pd, Os, Ir, Pt, Cu, Zn, In, Ge, Sn, Sb, Te, Bi, Ti, Zr, Hf, V, Nb, Ta, Cr, Mo, W, Al, In, Sn, Sb, Bi; La, Ce, Pr, Nd, Pm, Sm, Eu, Gd, Tb, Dy, Ho, Er, Tm, and Yb; $R^1$ is selected from linear or branched $C_{1-10}$ alkyls, $C_{1-10}$ alkoxyalkyl, and $C_{1-10}$ aminoalkyl; $R^{2-3}$ can be same or different selected from group consisting of hydrogen, linear or branched $C_{1-10}$ alkyls, $C_{1-10}$ alkoxyalkyl, and $C_{1-10}$ aminoalkyl; at least one of $R^1$, $R^2$ or $R^3$ is an alkyl group; preferably $R^1$ is an alkyl group; X is selected from the group consisting of alkoxy, beta-diketonates, acetates, ketoiminates, diimines, alkoxides, amides, hydrides, beta-ketoesters, amidinates, guanidinates, cyclopentadienyl, cyanide, isocyanide, pyrrolyl, formate, acetate, cyanate, oxalate, malonate, phenoxide, thiolate, trialkylsiloxide, bis(trialkylsilyl)amide, sulfide, nitrate, alkyl, silylalkyl, fluoroalkyl, aryl, hydride, pyrrolyl, and halide; n=0, 1, 2, 3; p=1, 2; exemplary alkoxy include, but not limited to; methoxy, ethoxy, n-propoxy, iso-propoxy, n-butoxy, sec-butoxy, iso-butoxy, tert-butoxy, and tert-pentoxy; exemplary amide include, but not limited to; dimethylamide, diethylamide, and ethylmethylamide; exemplary alkyls include; methyl, ethyl, methyl, ethyl, n-propyl, iso-propyl, n-butyl, iso-butyl, sec-butyl, tert-butyl, isomers of pentyl, and polyalkyl.

In another aspect, the present invention provides a metal compound represented by Structure G:

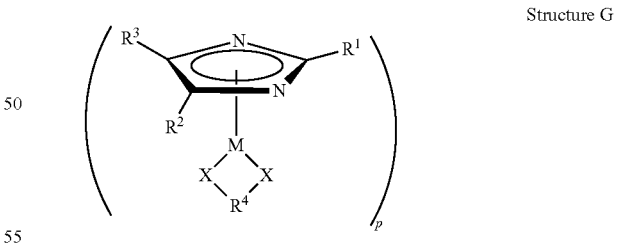

Structure G wherein M is a metal selected from Group 4 to 16, including: Al, Sb, Bi, La, Ce, Pr, Nd, Pm, Sm, Eu, Gd, Tb, Dy, Ho, Er, Tm, Yb; $R^1$ is selected from linear or branched $C_{1-10}$ alkyls, $C_{1-10}$ alkoxyalkyl, and $C_{1-10}$ aminoalkyl; $R^{2-3}$ can be same or different selected from group consisting of hydrogen, linear or branched $C_{1-10}$ alkyls, $C_{1-10}$ alkoxyalkyl, and $C_{1-10}$ aminoalkyl; at least one of $R^1$, $R^2$ or $R^3$ is an alkyl group; preferably $R^1$ is an alkyl group; $R^4$ is selected from linear or branched $C_{2-10}$ alkyl, $C_{6-10}$ aryl; X is selected from oxygen or $NR^5$ wherein $R^5$ is selected from linear or branched $C_{1-10}$ alkyls, $C_{1-10}$ alkoxyalkyl, and $C_{1-10}$ aminoalkyl; p=1.

In addition, there are also complexes, which contain two or more metals, but bimetallic is the most common case. Thus, these complexes are described as $N^{(p+)}P^{(q+)}(I)_a(X)_b(Y)_c(Z)_d(L)_x$ where N and P are two different metals of oxidation states of (p+) and (q+), respectively. In these complexes, (p)+(q)= (a)+(b)+(c)+(d), whereas (x), (Y), (Z) and (L) are as described above.

The present invention is a metal imidazolate complex which can be substituted in at least the 2-position, preferably in the 2 and 4 or 5 position, preferably in the 2, 4 and 5 positions with a sufficiently bulky group, R, of the formula:

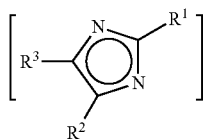

wherein the $R^1$, possibly $R^1$ and $R^2$ and possibly $R^1$, $R^2$ and $R^3$ groups have sufficient 3-dimensional form to impart a property to the imidazolate to bond with metal ions in a fashion that precludes the formation of a metal imidazolate polymer structures, but rather permits monomeric or dimeric metal compounds to form, which are volatile, have low melting points and are readily soluble in solvents. $R^1$ can be a bulky group, $R^2$ and $R^3$ can be bulky groups or groups which are not bulky.

Preferably, the imidazolate's $R^1$, $R^2$ and $R^3$ are individually selected from the group consisting of methyl, ethyl, propyl, tert-butyl, isopropyl, tert-amyl, neopentyl, adamantyl, hexyl, cyclohexyl, propyl, butyl, isobutyl, pentyl, isopentyl, neopenty, norbornyl, and bicyclo[2.2.1]heptyl.

In some cases, the imidazolate $R^2$ group is methyl, ethyl, propyl or isopropyl.

Preferably, the imidazolate's $R^2$ and $R^3$ are bulky groups.

The novel imidazolate compounds of the present invention are unique in that they are formed from imidazolate anions, which are formed by the deprotonation of imidazoles that are substituted in at least the 2 position, preferably in the 2 and 4 or 5 position, more preferably in the 2, 4 and 5 positions with alkyl groups that are sufficiently bulky as to preclude the imidazolate anions from bridging multiple metal centers to form polymeric involatile structures. Being thereby prevented from forming highly associated structures, they form monomeric or dimeric metal complexes, which are volatile.

Preferably, the imidazolate's $R_1$ is individually selected from the group consisting of methyl, ethyl, propyl, isopropyl, tert-butyl, isopropyl, tert-amyl, neopentyl, adamantyl, hexyl, cyclohexyl, propyl, butyl, isobutyl, pentyl, cyclopentyl, isopentyl, neopenty, norbornyl, bicyclo[2.2.1]heptyl, dimethylbutyl, dimethylpentyl, dimethylhexyl, sec butyl, ethylmethylpropyl, isohexyl, and isopentyl; $R^1$ and $R^2$ can be selected from the group consisting of methyl, ethyl, propyl, isopropyl, tert-butyl, isopropyl, tert-amyl, neopentyl, adamantly, hexyl, cyclohexyl, propyl, butyl, isobutyl, pentyl, cyclopentyl, isopentyl, neopenty, norbornyl, bicyclo[2.2.1]heptyl, dimethylbutyl, dimethylpentyl, dimethylhexyl, sec butyl, ethylmethylpropyl, isohexyl, and isopentyl.

Preferably, the imidazolate's $R_2$ is a hydrogen or a bulky group selected from the group consisting of; hydrogen, methyl, ethyl; isopropyl, tert-butyl, isopropyl, tert-amyl, neopentyl, adamantyl, hexyl, cyclohexyl, propyl, butyl, isobutyl, pentyl, cyclopentyl, isopentyl, neopentyl, norbornyl, bicyclo[2.2.1]heptyl, dimethylbutyl, dimethylpentyl, dimethylhexyl, sec butyl, ethylmethylpropyl, isohexyl, and isopentyl.

Most preferably, the imidazolate is:
2,4,5-tri-tert-butylimidazolate;
2-tert-butyl-4,5-di-(1,1-dimethylpropyl)imidazolate;
2-(1,1-dimethylbutyl)-4,5-di-tert-butylimidazolate;
2-(1,1-dimethylbutyl)-4,5-di-(1,1-dimethylpropyl)imidazolate;
2,4,5-trimethylimidazolate;
2-tert-butyl-4-methyl-5-ethylimidazolate;
2-ethyl-4-methylimidazolate;
2-isopropyl-4,5-di-tert-butylimidazolate;
2-tert-butyl-4,5-di-isopropylimidazolate;
2-isopropyl-4,5-di-tert-amylimidazolate;
2-sec-butyl-4,5-di-tert-amylimidazolate; and,
2-(1-ethyl-propyl)-4,5-di-tert-butylimidazolate,
and their metal complexes. Thus, by using sufficiently bulky groups, such as tert-butyl, when the imidazole is deprotonated to give an anion, it coordinates to a metal in an 'eta-5' mode, where the plane of the five membered ring is positioned sideways to the metal ion. This then permits the metal to bond to all five atoms of the imidazolate ring, as shown in Formula B, where R represents bulky alkyl type groups. Additionally, the imidazolate anions of this disclosure can also bind in a novel 'end on' manner, as shown below in Formula C, where the bulky substituents permit the metal to bind only to to one of the imidazolate nitrogens. While not wishing to be bound by theory, it is also anticipated that other novel binding modes exist between the two extremes of eta-5 and eta-1, where only two, three or four of the imidazolate ring atoms participate in bonding to the metal. Also, another mode of imidazolate coordination is shown in Formula D, which permits the formation of metal imidazolate dimer complexes.

Bulky groups for the purpose of the present invention are groups, which have sufficient 3-dimensional spacial form to create the steric hindrance, so that metals bonding with the imidazolates of the present invention are enabled to be preferably bonded in the 'eta-5' bonding or end on eta-1 bonding of Formulae B and C, respectively. Additionally, the bonding modes between these two extremes are also possible, such as; eta-2, eta-3 and eta-4.

Bulky groups can comprise $C_{3-12}$ groups, preferably branched alkyl, cyclic or aromatic, and optionally further derivatized with other functional groups, such as; amine, hydroxyl, carboxylic, substituted amine and similar derivatives. Alkanes, alkenes, alkynes, cyclic forms of the same, aromatics, and their derivatives are all contemplated as bulky groups, as long as they meet the requirement of having sufficient bulk in the form of 3-dimensional spacial form to induce 'eta-5' bonding of the imidazole with metals, or eta-4, or eta-3 or eta-2 or eta-1 bonding to the metal. Other suitable bulky alkyl groups include, but not limited to; methyl, ethyl, propyl, isopropyl, tert-amyl, neopentyl, adamantyl, hexyl, cyclohexyl, propyl, butyl, isobutyl, tertbutyl, pentyl, isopentyl, neopentyl, norbornyl, bicyclo[2.2.1]heptyl, nitro, $C_9$-$C_{20}$ alkylphenyl, $C_1$-$C_{10}$ alkoxy; alkylamine; and $C_1$-$C_{10}$ alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ alkyl functionalized with an ester group and mixtures thereof.

Thus, this disclosure teaches the synthesis of volatile metal imidazolate complexes, which use imidazole ligands, which are substituted in at least the 2 position.

Thus, in the present invention, when the bulky groups are characterized by stating they impart a property to the imidazolate to bond with metals in a 'eta-5 bond', or eta-1 bond, this does not preclude additional bonding in linear fashion in addition to 'eta-5', but merely describes a favored or preferred bonding form. Without the bulky groups, these imidazolates would not exhibit the propensity to favor 'eta-5' bonding (Formula B), or eta-1 bonding (Formula C) or the non-coplanar bridging bonding (Formula D).

Unsubstituted phenyl, for instance, does not display sufficient bulkiness to be included in the definition of bulky groups, due to its largely planar 3-dimensional shape, whereas, cyclohexane has sufficient bond angles to help constitute a bulky group.

In addition, these alkyl substituents can also be functionalized with coordinating groups, such as; ether, amine, amide, cyano, isonitrile, imine, amidinine, ester, pyridine, imidazole, pyrrole, pyrazole, oxazole, isooxazole, furan, pyrimidine, furfuryl, oxirane, aziridine, oxolane, 1,3-dioxolane, 1,4-dioxane, 1,3,5-trioxane, pyrrolidine, piperidine, quinuclidine. They can also be functionalized with groups capable of being deprotonated, so that with the imidazole also being deprotonated, they form dianions, which then can be coordinated to metal centers. Such groups include, but are not limited to; cyclopentadiene, pyrrole, beta-diketone, beta-ketoimine, beta-diimine, alcohol, amine, amide, pyrrole, phenol, carboxylate, and amidinate.

The novel compounds of the present invention comprise anionic alkyl functionalized imidazolate ligands, which are coordinated to transition metals, lanthanide metals, actinide metals, Group 1 and main group metals, including the chacogenides, to yield either monomeric or dimeric compounds, in addition to neutral ligand adducts of those compounds, which have exceptional thermal stability and clean evaporation characteristics.

Figure 2:
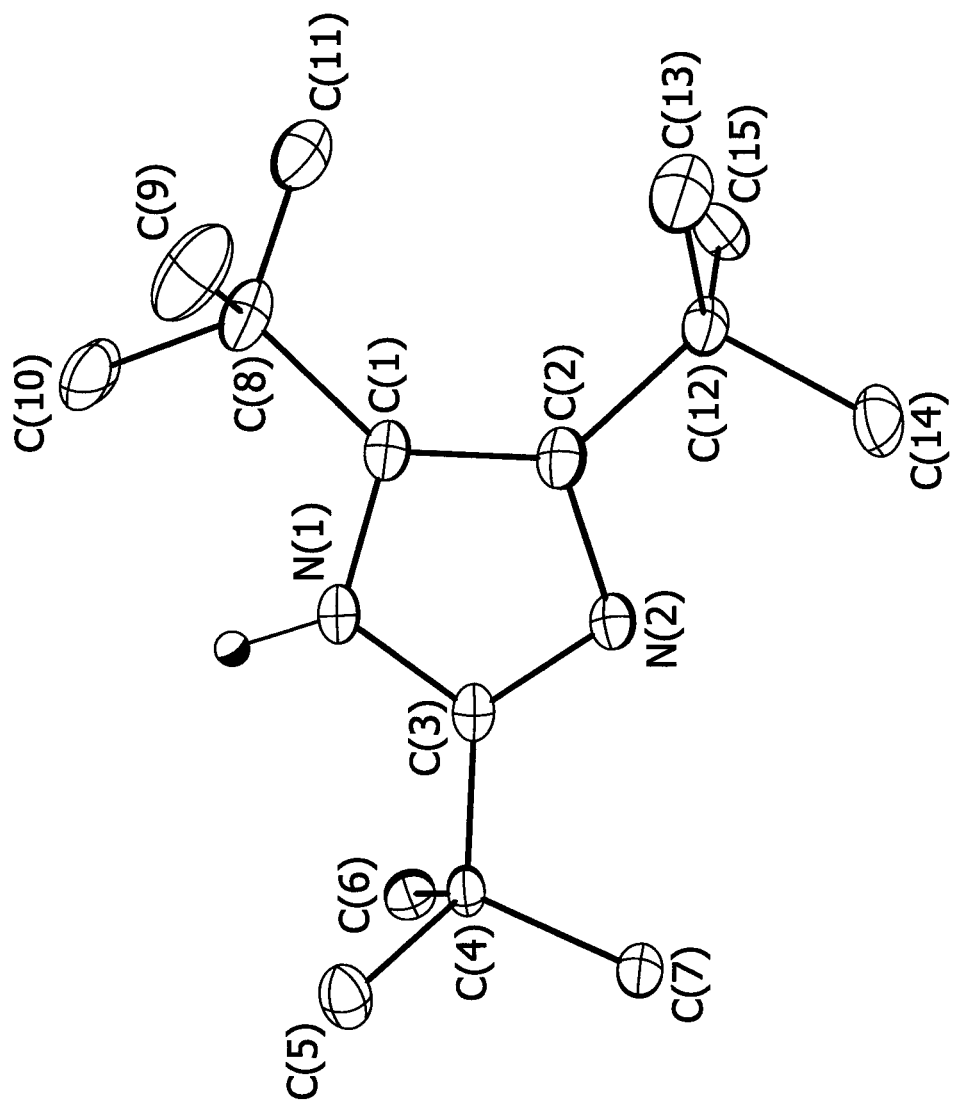
FIG. 2 is shows the structure of 2,4,5-tri-tert-butylimidazole, as determined by X-ray crystallography.

The imidazolate anions used can also be asymmetrically alkylated to yield lower melting point compounds of high solubility, well suited to direct liquid injection (DLI). The structure of the ligand 2,5-di-tertbutylimidazole, a new novel imidazole ligand created according to this disclosure (see Example 1), is shown in FIG. 1. Also shown is the structure of 2,4,5-tri-tert-butylimidazole in FIG. 2.

Clean evaporation characteristics of these new metal complexes is especially useful, since a low level of involatile residue is highly desirable, as this translates to a controlled evaporation of the metal complex being possible, if it is used as a source precursor compound for ALD or CVD processes. In addition, for CVD or ALD processes, many metal precursors are dissolved in a solvent, and this solution is vaporized in a direct liquid injection (DLI) system. Basically, this comprises delivering a precisely controlled flow of solution into a vaporizer, where the solution and its dissolved solute are rapidly heated and vaporized under reduced pressure. The resulting vapor is then transported into the CVD or ALD reactor. Typically, there are minaturized nozzles and narrow bore tubes used inside the vaporizer at the point, where the solution is nebulized or simply introduced into the vaporization temperature. If the solute does not fully evaporate and an involatile residue is formed, these fine bore tubes can become obstructed, thereby preventing any further flow of solution. For these reasons, it is highly desirable for the involatile residue observed in the TGA experiment to be as low as possible to avoid the accumulation of obstructing residues, for the best possible DLI performance. This is especially important in a commercial manufacturing environment, where such an equipment failure is prohibitively expensive.

The present invention is directed towards the use of substituted imidazole ligands from which volatile monomeric or dimeric transition metal complexes can be synthesized. This is demonstrated by Examples 12, 13, 14, 15, 16, 17, 18, 19, 20, 21, 23, 25 and 26 for titanium imidazolate compounds; Example 27 for zirconium; Examples 28 and 29 for cobalt; Example 30 for iron; Examples 31, 32, 33 and 34 for ruthenium; Example 36 for manganese; Example 39 for lanthanum; Example 40 for cerium, and Example 41 for europium.

In all of the above examples, an imidazole ligand is either directly reacted with a metal halide (as in the case of titanium tetrachloride) or, is first deprotonated with a suitable base, such as n-butyl lithium, then reacted with a metal halide to ultimately give a metal imidazolate compound. In some cases, the metal halide species contains only one halide to be displaced by imidazole or imidazolate anion to yield the final product. Examples 12, 13, 14, 15, 16, 17, 18, 19, and 20 demonstrate this, where imidazolate anion displaces chloride ion from $(Cl)Ti(OR)_3$, where R=OEt or OiPr (Et=ethyl; iPr=isopropyl). Similarly, Example 36 shows that 2-tert-butyl-4,5-di-(1,1-dimethylpropyl)imidazolate can displace bromide ion from manganese pentacarbonyl bromide to give manganese (2-tert-butyl-4,5-di-(1,1-dimethylpropyl)imidazolate)tricarbonyl. In other cases, halide is displaced from a metal halide to yield a metal imidazolate compound still bearing halide which can then subsequently be displaced to form a new metal imidazolate compound.

Demonstrations of this approach are found in Examples 22 and 24, where initial displacement of chloride ion from $TiCl_4$ by 2,4,5-tri-tert-butylimidazole or 2-tert-butyl-4,5-di(1,1-dimethylpropyl)imidazole yields titanium($tBu_3$imidazolate)trichloride and titanium($tBu$-tamyl$_2$imidazolate)trichloride, respectively. The titanium($tBu_3$imidazolate)trichloride compound is then reacted with methoxide ion to displace one (Example 25), then two (Example 26) chloride ions to yield titanium($tBu_3$imidazolate)methoxide dichloride and titanium ($tBu_3$imidazolate)dimethoxide chloride complexes, respectively.

Similarly, in Examples 28 and 29, cobalt dichloride is first reacted with 2,4,5-tri-tert-butylimidazolate and 2-tert-butyl-4,5-di-(1,1-dimethylpropyl)imidazolate anions, respectively, to first displace one chloride ion to give the intermediates: cobalt(2,4,5-tri-tert-butylimidazolate) chloride and cobalt(2-tert-butyl-4,5-di-(1,1-dimethylpropyl)imidazolate) chloride, respectively. In both cases, the remaining chlorides are then displaced by the addition of cyclopentadieide anion to give the final products.

A similar strategy is found in Example 30, where 2,4,5-tri-tert-butylimidazolate anion displaces the first chloride ion from iron dichloride and the second chloride is then displaced with cyclopentadienide anion. Thus, it is clear that displacement of halide ion from a transition metal halide is readily accomplished by reaction with an imidazole ligand, or its imidazolate anion, to form a transition metal imidazolate complex. It is also clear that if there are remaining halides in the metal imidazolate complex, they can be displaced by other ions to yield new and different imidazolate metal complexes. In this way, imidazolate complexes of all the transition metals can be prepared, since metal halides for all of the transition metals exist.

Similarly, Examples 39, 40 and 41 illustrate that lanthanum triiodide, cerium triiodide and europium diiodide can be reacted with potassium (2-tert-butyl-4,5-di-(1,1-dimethylpropyl)imidazolate) to yield lanthanum(2-tert-butyl-4,5-di-(1,1-dimethylpropyl)imidazolate)diiodide bis(tetrahydrofuran), cerium(2-tert-butyl-4,5-di-(1,1-dimethylpropyl) imidazolate)diiodide bis(tetrahydrofuran) and europium (2-tert-butyl-4,5-di-(1,1-dimethylpropyl)imidazolate) iodide bis(tetrahydrofuran) respectively. Example 42 shows that europium diiodide can be reacted with potassium 2,4,5-tri-tert-butylimidazolate to yield di-europium tetra(2,4,5-tri-tert-butylimidazolate). Thus, since halide of all of the lanthanide elements exist, lanthanide imidazolate complexes can be synthesized. Similarly, actinide metal imidazolate complexes can be prepared from actinide metal halides.

Example 27 shows that zirconium tetra(dimethylamide) can be reacted with 2,4,5-tri-tert-butylimidazole to yield zirconium (2,4,5-tri-tert-butylimidazolate)tri(dimethylamide). Therefore, metal imdazolates are readily prepared by the reaction of metal amide compounds with the imidazole ligands of this disclosure.

The present invention is directed to the synthesis and use of new and novel and volatile Group 3-16 transition metal, lanthanide metal, actinide metal and main group metal complexes, including the chalogenides of alkylated imidazolate-based compounds and their solutions for vapor delivery upon direct liquid injection, wherein the alkyl groups of the imidazolate ligand anion can be bulky hydrocarbons, such as: tert-butyl, tert-amyl, etc.; and can be nitrogen or oxygen containing alkyl, such as: methyl, ethyl, propyl, isopropyl, tertiary amine or ether groups. Additionally, these new compounds can also coordinate with other neutral ligands, such as: ethers or amines or alkoxyamines The present invention also includes a novel method of synthesizing the metal compounds by direct metallization of the imidazolate ligands using a metal reagent, such as a metal hexamethyldisilazane, metal alkoxide, metal hydroxide or metal hydride, thereby providing an efficient alternative to using the standard metathesis type of reaction, where the imidazole is first treated with a metal hydride, such as sodium hydride, to form a sodium imidazolate, which is then in turn reacted with a metal halide, such as iodide.

Other novel techniques for synthesizing these new compounds include, but are not limited to, direct reaction of the imidazole ligands with metal, etc., in the presence or absence of added reagents, such as ammonia, or by reacting the imidazole ligands with metal vapor. The novel compounds may also be prepared by electrochemical syntheses.

Additionally, a wide variety of metals and metalizing agents can be used to effectively deprotonate the imidazole ligands prior to reacting with a source of the metal of the final complex. Such deprotonating reagents include, but are not limited to: n-butyl lithium, n-hexyl lithium, sec-butyl lithium, tert-butyl lithium, lithium diisopropylamide, potassium hydride, sodium hydride, sodium metal, sodium amide, potassium metal, potassium amide, barium metal, sodium t-butoxide, potassium t-butoxide, alkyl and aryl Grignard reagents. Metal sources include, but are not limited to: metal iodide, metal bromide, metal chloride, metal trifluoromethylsulfonate, metal trifluoroacetate, metal hexafluoroacetylacetone, metal trifluoroacetylacetonate, metal acetyacetonate, metal diimine, metal ketoimine, metal amidinate, metal guanidinate, metal amide, metal alkoxide, metal amide, metal carbonate, metal acetate, metal carbonate, metal formate, metal propionate, metal phenoxide and metal hydroxide.

Mixed complexes can also be created, where the alkyl based imidazole substituents are varied differently among imidazolate anions, and then this mixture is complexed to a metal (M). Thus, if two different imidazolate anions $I^1$ and $I^2$ are mixed together, and then complexed to a metal to satisfy two of its valencies (it could be of a valency higher than two, but the remaining valencies are satisfied by other coordinating anions), three unique metal complexes can be made; i.e. $M(I^1)_2$, $M(I^1I^2)$, and $M(I^2)_2$. If three different imidazolate anions $I^1$, $I^2$ and $I^3$ are mixed, and then complexed to M, six metal complexes are formed; i.e., $M(I^1)_2$, $M(I^1I^2)$, $M(I^1I^3)$, $M(I^2)_2$, $M(I^2I^3)$ and $M(I^3)_2$. These mixtures will be either liquids or highly soluble formulations for DLI. This same logic can also be applied to making metal complexes from a mixture of four, five or six imidazole ligands. Also, the groups $R^{1-3}$ of one imidazolate anion can be joined to the $R^{1-3}$ groups of another imidazolate anion to connect the two anions together. The neutral ligand (L) is selected from aliphatic $C_1$-$C_{20}$ ether or polyether, crownethers, such as 18-crown-6, amine or polyamine, alkoxyamine or polyalkoxyamine, amide or polyamide, ester or polyester, aromatic ether, aromatic ester, aromatic amide, aromatic amine, pyridine, imidazole, pyridine, pyrazine, furan, alkylcarbonate, pyrrole, trialkylphosphine or triarylphosphine. Additionally, groups $R^1$, $R^2$, $R^3$ and can be linked together to form ring structures, These ring structures can also be aromatic.

Several advantages can be achieved through these metal-containing polyalkylated imidazole based compounds as precursors for chemical vapor deposition or atomic layer deposition, and these include:

an ability to form reactive complexes in good yield;

an ability to form monomeric or dimeric thermally stable complexes, coordinated with one kind or mixed kinds of ligand, thus achieving higher a capability to form highly conformal metal oxide thin films, suited for use in microelectronic devices;

an ability to enhance the surface reaction between the metal-containing alkylated imidazolate anion and the surface of a substrate due to the high chemical reactivity of the complexes; and, an ability to tune the physical properties of these metal-containing polyalkyl imidazole anions via a change in the alkyl substituent groups.

Additionally, metal complexes can also be made by coordinating two different polyalkylated imidazolate anions to a metal center, such that the two ligands experience an optimal 'fit' or 'interlock' with each other and around the metal in such a way as to provide an adequate coordination sphere to create a stable monomeric or dimeric complex.

While not wishing to be bound by theory, the molecules of this disclosure are excellent precursors for use in CVD or ALD processes for depositing metal oxide containing films, by reacting them together, either sequentially or simultaneously, with an oxidizer, such as: water, hydrogen peroxide, alcohol, oxygen, ozone, nitrous oxide, nitrogen dioxide or combinations thereof. Additionally, the metal precursor molecules of this disclosure can be used in a CVD, pulsed CVD or ALD mode to deposit metal containing films, including metal nitrides by reacting with nitrogen sources, such as amines or ammonia. Alternatively, metallic films may be formed by reacting with a suitable reducing agent, such as hydrogen.

In one embodiment, the present invention is a metal compound of the formula: $(M^{(n+)})_z(I)_a(X)_b(Y)_c(Z)_d(L)_x$ where (I) represents an alkylated imidazolate anion having the formula:

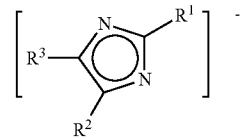

and (M) is selected from the group consisting of: Sc, Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, La, Ce, Pr, Nd, Pm, Sm, Eu, Gd, Tb, Dy nHo, Er, Tm, Yb, Lu, Ac, Th, Pa, U, Np, Pu, Am, Cm, Bk, Cf, Es, Fm, Md, No, Lr, Li, Na, K, Rb, Cs, Fr, Al, Ga, In, Tl, Si, Ge, Sn, Pb, P, As, Sb, Bi, S, Se, Te, Po and mixtures thereof; where (n) is 1-6; (z) is one or two; a, b, c, d, n and z are selected to make the metal complex electroneutral, and when X, Y and Z are monoanions then (a)+(b)+(c)+(d)=(z)×(n); when (a) is greater than 1, each imidazolate anion can be different; (L) is a neutral ligand selected from the group consisting of aliphatic $C_1$-$C_{20}$ ether or aminoether, polyether; crownether; crown aminoether; amine; poly amine; amide; poly amide; ester; polyester; aromatic ether; aromatic ester; aromatic amide; aromatic amine; pyridine; imidazole; pyridine; pyrazine; furan; pyrrole, olefin, diolefin, triolefin, polyolefin, alkyne, silylolefin, silyalkyne, carbon monoxide, nitrile, silylnitrile or isocyanide, alkyl phosphine, and aromatic phosphine; (x) is 1-5; (X), (Y) and (Z) are individually selected from the group consisting of: beta-diketonates, ketoiminates, diimines, alkoxides, amides, amidines, hydrides, beta-ketoesters, amidinates, guanidinates, cyclopentadienyl, cyanide, isocyanide, formate, acetate, oxalate, malonate, phenoxide, thiolate, trialkylsiloxide, bis(trialkylsilyl)amide, sulfide, nitrate, alkyl, silylalkyl, trialkylsiloxide, fluoroalkyl, aryl, hydride, pyrrolyl, polyalkylated pyrrolyl anion, halide and mixtures thereof; and $R^{1-3}$ are individually selected from the group consisting of H, $C_{1-12}$, wherein at least one of $R^{1-3}$ is $C_{1-12}$, and $C_{1-12}$ can be substituted. The $C_{1-12}$ is selected from the group consisting of normal and branched alkyl, normal and branched alkenyl, normal and branched alkynyl, aromatic and heteroatom derivatized compounds of the preceding groups, that is, substituted. Substitution can be with nitrogen atoms, oxygen atoms and other heteroatoms, forming such groups as amine, ether, alcohol, carboxy, ketone, and similar heteroatom substitutions.

Preferably, $R^1$ is $C_{1-12}$, and $C_{1-12}$ can be substituted. More preferably, $R^1$ and $R^2$ are $C_{1-12}$, and $C_{1-12}$ can be substituted. Still more preferably, $R^1$, $R^2$ and $R^3$ are $C_{1-12}$, and $C_{1-12}$ can be substituted. Preferably, at least one of $R^{1-3}$ is tertiary alkyl, independently selected from tert-butyl and tert-amyl.

In one embodiment, the metal compound of the present invention is selected from the group consisting of Mn(I) (CO)$_3$, Ti(I)(O$^i$Pr)$_3$, Ti(I)(OEt)$_3$, Ti(I)(NMe$_2$)$_3$, Ti(I) (NMeEt)$_3$, Ti(I)Cl$_3$, Zr(I)Cl$_3$, Zr(I)$_2$Cl$_2$, Zr(I)(OEt)$_3$, Zr(I) (NMe$_2$)$_3$, Zr(I)$_2$(OEt)$_2$, Zr(I)$_2$(O$^i$Pr)$_2$, Zr(I)$_2$(NMe$_2$)$_2$, Fe(I) (C$_5$R$_5$), Ru(I)(C$_5$R$_5$), Co(I)(C$_5$R$_5$), Ln(I)(X)$_2$ (L)$_2$, Ln(I)(X) (L)$_2$, wherein R is independently selected from hydrogen, methyl, ethyl, n-propyl, and iso-propyl, (X) can be halide, (L) is a neutral ligand.

A preferred list of the compounds of the present invention includes metal compounds wherein imidazolate anion is independently selected from 2,4,5-tri-tert-butylimidazolate; 2-tert-butyl-4,5-di-(1,1-dimethylpropyl)imidazolate; 2-(1,1-dimethylbutyl)-4,5-di-tert-butylimidazolate; 2-(1,1-dimethylbutyl)-4,5-di-(1,1-dimethylpropyl)imidazolate; 2,4,5-trimethylimidazolate; 2-tert-butyl-4-methyl-5-ethylimidazolate; 2-ethyl-4-methylimidazolate; 2-isopropyl-4,5-di-tert-butylimidazolate; 2-tert-butyl-4,5-di-isopropylimidazolate; 2-isopropyl-4,5-di-tert-amylimidazolate; 2-sec-butyl-4,5-di-tert-amylimidazolate; and, 2-(1-ethyl-propyl)-4,5-di-tert-butylimidazolate.

Preferably, the metal compound of the present invention is selected from the group consisting of titanium (2-tert-butyl-4,5-di-(1,1-dimethylpropyl)imidazolate)triethoxide; titanium (2-tert-butyl-4,5-di-(1,1-dimethylpropyl)imidazolate) triiso-propoxide; titanium(2,4,5-trimethylimidazolato) triisopropoxide; titanium(2-ethyl-4-methyl-imidazolate) triisopropoxide; di-titanium bis(2,5-di-tert-butyl-imidazolate)hexaethoxide; titanium (2-isopropyl-4,5-di-(1, 1-dimethylpropyl)imidazolate)triisopropoxide; di-titanium bis(2,4-di-tert-butylimidazolate)hexaisopropoxide; titanium bis(2,5-di-tert-butylimidazolate)diisopropoxide; titanium(2, 4,5-tri-tert-butylimidazolate)triisopropoxide; titanium (2-tert-butyl-4,5-di(1,1-dimethylpropyl)limidazolate)-triiso-propoxide; titanium(2,4,5-tri-tert-butyl-imidazolate)trichloride; titanium (2-tert-butyl-4,5-di-(1,1-dimethylpropyl)imidazolate)trichloride; titanium (2,4,5-tri-tert-butyl-imidazolate)dichloride methoxide; titanium(2,4,5-tri-tert-butyl-imidazolate) chloride dimethoxide; zirconium(2,4,5-tri-tert-butyl imidazolate)tri(dimethylamide); cobalt(2,4,5-tri-tert-butylimidazolate)(cyclopentadienide); cobalt (2-tert-butyl-4,5-di(1,1-dimethylpropyhimidazolate) (cyclopentadienidel); iron (2,4,5-tri-tert-butylimidazoate) (cyclopentadienide); ruthenium (2,4,5-trimethylimidazolate) (pentamethylcyclopentadienide); ruthenium (2-ethyl-4-methylimidazolate)(pentamethylcyclopentadienide); ruthenium (2-tert-butyl-4-methyl-5-ethylimidazoate)I(pentamethylcyclopentadienide); ruthenium (2-tert-butyl-di(1,1-dimethylpropyl)imidazolate) (pentamethylcyclopentadienide); ruthenium(pentamethylcyclopentadienide) (imidazolate); manganese(2-tert-butyl-4,5-di-(1,1-dimethylpropyl)-imidazolate)tricarbonyl; lanthanum (2-tert-butyl-4,5-di-(1,1-dimethylpropyl)imidazolate)diiodide bis (tetrahydrofuran); and cerium(2-tert-butyl-4,5-di(1,1-dimethylpropyl)imidazolate diiodide bis(tetrahydrofuran).

In one embodiment, the present invention is a metal compound of the formula $M^{(n+)}(I)_a(X)_b(Y)_c(Z)_d(L)_x$ where (I) is an imidazolate based dianion having the formula:

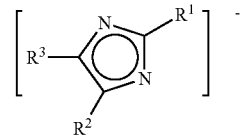

functionalized with an acidic group which acidic group is deprotonated, the acidic group selected from the group consisting of; an alcohol, an amine, an amide, a carboxylate, a beta-diketone, a beta-diimimine, a cyclopentadiene, and a pyrrole anion, wherein when (a)=1 then (a)+1+(b)+(c)+(d)= (n) and wherein when (a)=2 then (a)+2+(b)+(c)+(d)=(n); and (X), (Y) and (Z) are individually selected from the group consisting of: beta-diketonates, ketoiminates, diimines, alkoxides, amides, amidines, hydrides, beta-ketoesters, amidinates, guanidinates, cyclopentadienyl, cyanide, isocyanide, formate, acetate, oxalate, malonate, phenoxide, thiolate, trialkylsiloxide, bis(trialkylsilyl)amide, sulfide, nitrate, alkyl, silylalkyl, trialkylsiloxide, fluoroalkyl, aryl, hydride, pyrrolyl, polyalkylated pyrrolyl anion, halide and mixtures thereof; and $R^{1-3}$ are individually selected from the group consisting of H, $C_{1-12}$, wherein at least one of $R^{1-3}$ is $C_{1-12}$, and $C_{1-12}$ can be substituted.

In yet another embodiment, the present invention is a metal compound, which contains two metals, of the formula $N^{(p+)}$ $P^{(q+)}(I)_a(X)_b(Y)_c(Z)_d(L)_x$ where N and P are two different metals of oxidation states (p+) and (q+), respectively; wherein (p)+(q)=(a)+(b)+(c)+(d); and (X), (Y) and (Z) are individually selected from the group consisting of: beta-diketonates, ketoiminates, diimines, alkoxides, amides, amidines, hydrides, beta-ketoesters, amidinates, guanidinates, cyclopentadienyl, cyanide, isocyanide, formate, acetate, oxalate, malonate, phenoxide, thiolate, trialkylsiloxide, bis(trialkylsilyl)amide, sulfide, nitrate, alkyl, silylalkyl, trialkylsiloxide, fluoroalkyl, aryl, hydride, pyrrolyl, polyalkylated pyrrolyl anion, halide and mixtures thereof; and where (I) represents an alkylated imidazolate anion having the formula:

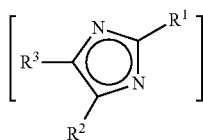

and $R^{1-3}$ are individually selected from the group consisting of H, $C_{1-12}$, wherein at least one of $R^{1-3}$ is $C_{1-12}$, and $C_{1-12}$ can be substituted.

The present invention is also a process where a metal compound of the above compounds is used as a volatile precursor for the deposition of metal containing thin films by a process selected from the group consisting of ALD, CVD, PECVD, pulsed CVD and molecular layer deposition; over a temperature range of 0° C. to 1000° C. and a pressure of 0.1 Torr to 1 atmosphere.

Another embodiment is a process using the metal compounds described above to grow thin metal containing films by spinning a solution of them onto a substrate and then reacting the resulting layer of precursor to give the desired metal containing film.

Additionally, the present invention is a process where a metal compound, described above is used as volatile precursors for the growth of phase change alloys by the processes selected from the group consisting of ALD, CVD, PECVD, pulsed CVD, and Molecular layer Deposition.

More preferably, he process is wherein thin films are grown by deposition from a solution of these precursors in a super critical fluid. Preferably, the super critical fluid is carbon dioxide.

In another embodiment, the present invention is a process using a metal compound of the above descriptions wherein the process is selected from the group consisting of ALD, CVD, pulsed CVD, PECVD, and molecular layer deposition; using a reactor pressure between 0.001-1000 Torr; a temperature from 0-1000° C.; reacting the metal compound with an oxidant selected from the group consisting of water, alcohol, oxygen, ozone, nitrous oxide, nitrogen dioxide, hydrogen peroxide and combinations thereof, to grow a metal oxide containing film.

In an alternate of the above process, the present invention is a process using a metal compound described above, wherein the process is selected from the group consisting of ALD, CVD, pulsed CVD, PECVD, and molecular layer deposition; using a reactor pressure between 0.001-1000 Torr; a temperature from 0-1000° C.; by reacting the metal compound with a reagent of nitrogen source molecules selected from the group consisting of ammonia, amines and mixtures thereof.

The present invention is also a method of synthesizing the metal compounds described above by direct metallization of the imidazole ligands using a metal reagent selected from the group consisting of n-butyl lithium, n-hexyl lithium, sec-butyl lithium, tert-butyl lithium, lithium diisopropylamide, potassium hydride, sodium hydride, sodium metal, potassium metal, sodium t-butoxide, and potassium t-butoxide; and then reacting the resulting product with a compound selected from the group consisting of metal iodide, metal acetate, metal carboxylate, metal carbonate, metal formate, metal bromide, metal trifluoroacetate, metal hexafluoroacetylacetone, metal trifluoroacetylacetonate, metal acetyacetonate, metal diimine, metal ketoimine, metal amidinate, metal guanidinate and mixtures thereof.

Alternately, the present invention is a method of directly synthesizing compounds of the descriptions above by reacting a an alkylated imidazole using a a compound selected from the group consisting of metal amide, metal phenoxide, metal hydroxide, metal alkyl, metal aryl and mixtures thereof.

In yet another embodiment the present invention is a method of synthesizing the metal compounds described above by reaction of the imidazole ligand with metal in the presence of ammonia.

A further embodiment is a process of dissolving a metal compound described above in a suitable solvent, and injecting a resulting solution into a direct liquid injection system for flash vaporization of the precursor and solvent and delivering a resulting vapor stream into a reactor for the growth of metal containing films by a process selected from the group consisting of; ALD, CVD, pulsed CVD, PECVD and Molecular Layer Deposition.

EXAMPLES

Example 1

Synthesis of 2,5-di-tert-butylimidazole 5.44 g (0.04 moles) of 2,2-dimethylpropanimideamide hydrochloride were mixed with 7.2 g (0.04 moles) of 1-bromopinacolone and 11.2 g of triethylamine in 16.0 g of diethylformamide (DEF) and stirred at room temperature for 7 days. The reaction mixture was then poured into water and extracted three times with 50 ml units of hexane. The hexane fractions were combined and washed three times with 50 ml aliquots of water. The hexane layer was then stirred with 5 g of anhydrous magnesium sulfate over night. The hexane was then removed by vacuum down to a volume of 5 ml to yield a fine suspension. This was filtered and the resulting solid washed with fresh hexane to yield 4.22 g (59% theoretical) of colorless fine crystalline product, 99% pure by Gas Chromatography Mass Spectrometry gave a parent ion at 180 amu. Structure confirmed by X-ray crystallography (see FIG. 1)

$^1$H NMR: (500 MHz, $D_8$ THF): δ=1.23 (s, 9H), b=1.3 (s, 9H), b=6.48 (s, 1H), b=10 (bs, 1H).

$^1$H NMR: (500 MHz, $D_8$ THF): δ=30.3 (s, 3C), δ=30.8 (s, 3C), δ=32.1 (s, 1C), δ=33.6 (s, 1C), δ=111 (bs, 1C), δ=148 (bs, 1C), δ=155 (s, 1C).

Example 2

Synthesis of 2,2,5,5-tetramethyl-3,4-hexanedione 26.44 mL (0.240 moles) 2-chloro-2-methyl propane was slowly added to 5.76 g, (0.240 moles) of magnesium turnings in 240 mL of tetrahydrofuran to make the Grignard reagent, t-BuMgCl. The freshly prepared Grignard reagent was slowly added to a mixture of 34 g (0.240 moles) copper bromide and 41 g (0.480 moles) of lithium bromide in 270 mL of tetrahydrofuran (THF), cooled to −65° C. 8.72 mL (0.10 moles) of oxalyl chloride in 30 mL of THF was then added slowly, maintaining mixture temperature at −65° C. The resulting mixture was stirred for an hour at −65° C., then warmed up to room temperature overnight. 90% of the THF is removed by vacuum, followed by the addition of 500 ml of hexane and 300 ml of a saturated aqueous solution of ammonium chloride. The hexane layer was separated and the aqueous layer extracted with three 200 ml lots of hexane. The hexane layers were then combined and washed with water prior to drying with 10 g of anhydrous magnesium sulfate. The mixture was then filtered and the hexane distilled off under atmospheric pressure to yield the product as a yellow oil. Yield=10.5 g (53% of theoretical)

Mass spectrum: 170 mu (parent ion).

Example 3

Synthesis of 2,4,5-tri-tert-butylimidazole 1.6 g (0.0094 moles) of 2,2,5,5-tetramethyl-3,4-hexanedione were mixed with 2.9 g (0.037 moles) of ammonium acetate, 3.4 g (0.057 moles) of acetic acid and 1.6 g (0.019 moles) of pivaldehyde and heated to 13° C. for 72 hrs in a sealed container. This mixture was then cooled and slowly added to an excess of aqueous saturated sodium bicarbonate solution. The resulting mixture was extracted with 3×50 ml of hexane. The hexane fractions were combined, washed three time with 20 ml aliquots of pure water, then dried over anhydrous sodium sulfate. Evaporation of hexane yielded crude 2,4,5-tri-tert-butylimidazole as its hydrate (two molecules of imidazole per water molecule). To dry this product, it was then refluxed in excess hexamethyldisilazane for 48 hrs. The hexamethyldisilazane and hexamethyldisiloxane (formed from the drying process) was then evaporated, and the resulting solid sublimed at 60° C. to give colorless crystals, yield 1.3 g (58% of theoretical).

$^1$H NMR: (500 MHz, $C_6D_6$): δ=1.24 (s, 9H), δ=1.26 (s, 9H), δ=1.65 (s, 9H), δ=8.07 (bs, 1H).
$^{13}$C NMR: (500 MHz, $C_6D_6$): δ=30.0 (s, 3C), δ=31.70 (s, 1C), δ=32.26 (s, 3C), δ=32.87 (s, 1C), δ=33.18 (s, 3C), δ=34.07 (s, 1C), δ=130.16 (s, 1C), δ=143.84 (s, 1C), δ=149.21 (s, 1C).

Mass spectrum: 236 mu (parent ion). Structure confirmed by single crystal X-ray analysis, see FIG. 2.

Example 4

Synthesis of 3,3,6,6-tetramethyl-4,5-octanedione 2-chloro-2-methyl butane (96 mL, 0.78 mol) was slowly added to magnesium pellets under a blanket of nitrogen, 18.72 g, (0.78 moles) of magnesium turnings in 780 ml of tetrahydrofuran were activated by the addition of 0.5 ml of 1,2-dibromoethane. 2-chloro-2-methyl butane (96 mL, 0.78 mol) were then slowly added resulting in the gradual formation of Grignard reagent, accompanied by a reaction exotherm. This Grignard reagent was then slowly added to a mixture of 112 g (0.78 mol) of copper bromide and 67 g (0.78 mol) of lithium bromide dissolved in 340 mL of terahydrofuran, cooled to −65° C. After all the Grignard was added and the temperature stabilized at −65° C., 26 mL (0.30 mol) of oxalyl chloride in 100 mL of THF was added slowly, maintaining mixture temperature at −65° C. The resulting mixture was stirred for an hour at −65° C., then warmed up to room temperature overnight. 90% of the THF was then removed by vacuum. 500 ml of hexane and 300 mL of saturated aqueous ammonium chloride were then added to the resultant slurry and the hexane layer separated. The aqueous layer was then further extracted with three 200 ml lots of hexane. The combined hexane layers were then washed with 200 mL of water, then dried over 10 g of anhydrous magnesium sulfate for one hour. The magnesium sulfate was then filtered off, and the hexane distilled off at atmospheric pressure to yield the crude product diketone as an orange red liquid. Yield=32.2 g (54% of theoretical).

Mass spectrum: 198 mu (parent ion).

Example 5

Synthesis of 2-tert-butyl-4,5-di-(1,1-dimethylpropyl)limidazole

A mixture of 32.3 g (0.163 mol) of 3,3,6,6-tetramethyl-4,5-octanedione, 50 g (0.652 mol) of ammonium acetate, 36 mL (0.326 mol) of pivaldehyde (36 mL, 0.326 mol) and 56 mL (0.978 mol) of acetic acid was heated to 200° C. in a sealed stainless steel vessel for 3 days. The resulting product mixture was neutralized with sodium bicarbonate solution, then extracted with four 200 ml lots of hexane. The combined hexane layers were washed 3× with 100 mL of water then 100 ml of saturated sodium chloride solution. 10 g of anhydrous magnesium sulfate was added and stirred overnight. Filtration followed by removal of hexane by vacuum yielded the crude product as a yellow oil. Yield 31.5 g (73% of theoretical).

Mass spectrum: 264 mu (parent ion).

Example 6

Synthesis of 2-iso-propyl-4,5-di-(1,1-dimethylpropyl)limidazole

A mixture of 60.0 g (0.303 mol) of 3,3,6,6-tetramethyl-4,5-octanedione, 140.2 g (1.818 mol) of ammonium acetate, 32.78 g (0.455 mol) of isobutyraldehyde and 163.77 g (2.727 mol) of acetic acid was heated at 180° C. in a sealed stainless steel vessel for 2 days. The resulting product mixture was neutralized with sodium bicarbonate solution, then extracted with two 200 ml lots of hexane. The combined hexane layers were washed 2× with 200 mL of water then 100 ml of saturated sodium chloride solution. 10 g of anhydrous magnesium sulfate was added and stirred overnight.

Filtration followed by removal of hexane by vacuum yielded the crude product as a light yellow liquid. The liquid was purified by vacuum distillation at 85° C. (0.3 torr) to yield 42.7 g of 2-iso-propyl-4,5-di-tert-amylimidazole, mp ~28° C. (56% yield).

Mass spectrum: 250 mu (parent ion).

Example 7

Synthesis of 2-tert-butyl-4-methyl-5-ethyl-imidazole

A mixture of 23.65 g (0.275 mol) of pivaldehyde, 77.1 g (1.000 mol) of ammonium acetate, and 90.10 g (1.500 mol) of acetic acid was charged into 500 ml flask equipped with addition funnel. The mixture was heated to 90-95° C. and 25.0 g (0.25 mol) of 2,3-pentanedione was added from the addition funnel within ~20 minutes. The mixture was heated for 2 hours at 110° C. and cooled to room temperature (RT). The resulting product mixture was extracted with 300 ml of hexane to remove oxazole derivatives. The remaining fraction was neutralized with sodium bicarbonate solution. The product was extracted with 2×150 ml of diethyl ether. The combined ether layers were washed with 2×100 mL of water then 100 ml of saturated sodium chloride solution. 10 g of anhydrous magnesium sulfate was added and stirred overnight. Filtration followed by removal of ether by vacuum yielded the crude product as a yellow solid. The material was purified by vacuum sublimation to yield 4.0 g of 2-tert-butyl-4-methyl-5-ethyl-imidazole (56 yield).

Mass spectrum: 166 mu (parent ion).

Example 8

Synthesis of 2-sec-butyl-4,5-di-tert-butylimidazole

A mixture of 10.0 g (0.059 mol) of 2,2,5,5-tetramethyl-3,4-hexanedione, 27.2 g (0.353 mol) of ammonium acetate, 7.6 g (0.088 mol) of 2-methylbutyraldehyde and 42.4 g (0.706 mol) of acetic acid was refluxed under nitrogen atmosphere for 16 hours. The resulting product mixture was neutralized with sodium bicarbonate solution, then extracted with two 200 ml lots of hexane. The combined hexane layers were washed with 2×100 mL of water then 2×100 ml of saturated sodium chloride solution. 10 g of anhydrous magnesium sulfate was added and stirred overnight. Filtration followed by removal of hexane by vacuum yielded 8.5 g of crude product as a light yellow solid. The solid was purified by vacuum sublimation to yield 6.3 g of white solid (46% isolated yield).

Mass spectrum: mu 236 (parent ion).

Example 9

Synthesis of 2-(1-ethyl-propyl)-4,5-di-tert-butylimidazole

A mixture of 15.0 g (0.088 mol) of 2,2,5,5-tetramethyl-3,4-hexanedione, 51.0 g (0.661 mol) of ammonium acetate, 17.8 g (0.178 mol) of 2-ethylbutyraldehyde and 60.38 g (1.001 mol) of acetic acid was refluxed under nitrogen atmosphere for 44 hours. The resulting product mixture was neutralized with sodium bicarbonate solution, then extracted with two 200 ml lots of hexane. The combined hexane layers were washed with 2×150 mL of water then 3×200 ml of saturated sodium chloride solution. 10 g of anhydrous magnesium sulfate was added and stirred overnight. Filtration followed by removal of hexane by vacuum yielded 17.7 g of crude product as a light yellow solid. The solid was purified by vacuum transfer to yield 15.1 g of white solid (68.5% isolated yield).

Mass spectrum: mu 250 (parent ion).

Example 10

Synthesis of 2,5-dimethyl-3,4-hexanedione 275 ml of 2 M solution of isopropylmagnesium chloride in tetrahydrofuran was then slowly added to a mixture of 78.90 g (0.55 mol) of copper bromide and 47.77 g 0.550 mol) of lithium bromide dissolved in 600 mL of THF, cooled to −65° C. After all the Grignard was added and the temperature stabilized at −65° C., 21.8 ml (0.250 mol) of oxalyl chloride in 100 mL of THF was added slowly, maintaining mixture temperature at −65° C. The resulting mixture was stirred for an hour at −65° C., then warmed up to room temperature overnight. 90% of the THF was then removed by vacuum. 300 ml of hexane and 100 mL of saturated aqueous ammonium chloride were then added to the resultant slurry and the hexane layer separated. The aqueous layer was then further extracted with two 100 ml lots of hexane. The combined hexane layers were then washed with 2×200 ml of 2 M HCl, 20 ml of 10% NaHCO$_3$ and 2×200 ml of 25% NaCl solution, then dried over 10 g of anhydrous magnesium sulfate for one hour. The magnesium sulfate was then filtered off and the hexane distilled off at atmospheric pressure to yield the crude product diketone as an orange red liquid. The product was purified by vacuum distillation to obtain 3.2 g of orange liquid (9% yield).

Mass spectrum: 141 mu (parent ion).

Example 11

Synthesis of 2-tert-butyl-4,5-iso-propyl-imidazole

A mixture of 2.5 g (mol) of 2,5-dimethyl-3,4-hexanedione, 6.5 g (mol) of ammonium acetate, 2.1 g (0.178 mol) of pivaldehyde and 7.6 g (mol) of acetic acid was refluxed under nitrogen atmosphere for 4 hours. The resulting product mixture was neutralized with sodium bicarbonate solution, then extracted with 50 ml of diethyl ether. Organic fraction was analyzed by GC-MS to confirm the formation of 2-tert-butyl-4,5-iso-propyl-imidazole.

Mass spectrum: mu 208 (parent ion).

Example 12

Synthesis of titanium (2-tert-butyl-4,5-di-(1,1-dimethylpropyl)imidazolate)triethoxide To a solution of 5.11 g (18.90 mmol) 2-tert-butyl-4,5-di-tert-amyl-imidazolate lithium salt in 50 mL of hexanes at −40° C. was added a solution of 4.13 g (18.90 mmol) TiCl (OEt)$_3$ in 25 mL of hexanes at −40° C. drop-wise. Upon addition, the reaction mixture became dark brown in color. The reaction was refluxed for 16 hours after which it was stopped, cooled, and an orange solid was filtered off weighing 0.48 g. The filtrate was pumped under vacuum to a viscous dark brown oil weighing 8.88 g. The crude product can be further purified by vacuum distillation.

$^1$H-NMR (500 MHz, C$_6$D$_6$) δ (ppm): 4.18 (q, 6H, OCH$_2$CH$_3$), 1.92 (q, 4H, imid), 1.67 (s, 12H, imid), 1.67 (s, 9H, imid), 1.08 (t, 9H, OCH$_2$CH$_3$), 0.85 (t, 6H, imid).

Example 13

Synthesis of titanium(2-tert-butyl-4,5-di-(1,1-dimethylpropyl)imidazolate)tri-iso-propoxide Method A: To a solution of 5.00 g (19.19 mmol) TiCl (OPr$^i$)$_3$ in 30 mL of THF at −78° C. was added 5.19 g (19.19 mmol) of 2-tert-butyl-4,5-di-tert-amyl-imidazolate lithium salt synthesized in situ. The reaction was refluxed for 16 hours after which all volatiles were removed under vacuum. The resulting waxy amber-colored solid was partially dissolved in hexanes and a white solid was filtered off weighing 2.32 g. The filtrate was pumped under vacuum to a viscous dark amber-colored oil weighing 8.51 g. The crude product can be further purified by vacuum distillation. The crude yield was 91%.

$^1$H-NMR (500 MHz, C$_6$D$_6$) δ (ppm): 4.50 (sept, 3H, OCH (CH$_3$)$_2$), 1.96 (q, 4H, imid), 1.69 (s, 12H, imid), 1.69 (s, 9H, imid), 1.13 (d, 18H, OCH(CH$_3$)$_2$), 0.84 (t, 6H, imid).

Method B: Under a blanket of dry nitrogen, 5.28 g (20 mmoles) of 2-tert-butyl-4,5-di-tert-amylimidazole) dissolved in 50 ml of dry THF were added, with stirring, to 0.8 g of potassium hydride (20 mmoles) in 50 ml of THF. After 20 minutes the evolution of hydrogen ceased leaving a clear solution. This was then added to 5.21 g (20 mmoles) of chlorotriisopropoxytitanium dissolved in 20 ml of THF at room temperature. The resulting mixture was then stirred for four hours at room temperature, after which the solvent was removed by the application of vacuum, 200 ml of hexane were added to dissolve the crude product and the resulting suspension filtered through Celite to yield a darge orange product. This was then vacuum distilled at 120-145° C./100 mTorr to give 7.15 g (73% yield) of a dark orange product.

$^1$H NMR: (500 MHz, C$_6$D$_6$): δ=0.84 (t, 6H), δ=1.1 (d, 18H), δ=1.69 (s, 9H), δ=1.7 (s, 12H), δ=1.96 (q, 4H). δ=4.5 (m, 3H).

Example 14

Synthesis of titanium(2,4,5-trimethyl-imidazolato) triisopropoxide,

To a solution of 2.00 g (7.68 mmol) TiCl(OPr$^i$)$_3$ in 50 mL of THF at −40° C. was added 1.26 g (7.68 mmol) of 2,4,5- trimethyl-imidazolate lithium salt dissolved in 25 mL THF drop-wise. The reaction was refluxed for 16 hours after which all volatiles were removed under vacuum. The resulting orange-red foamy solid was partially dissolved in 100 mL of toluene and a pale orange solid was filtered off weighing 0.75 g. The filtrate was pumped under vacuum to a viscous dark brown oil weighing 1.46 g. The crude product can be further purified by vacuum distillation. The crude yield was 57%.

Example 15

Synthesis of titanium(2-ethyl-4-methyl-imidazolate) triisopropoxide

To a solution of 1.80 g (6.91 mmol) TiCl(OPr$^i$)$_3$ in 50 mL of THF at −40° C. was added 1.00 g (6.91 mmol) of 2-ethyl-4-methyl-imidazolate lithium salt dissolved in 25 mL THF drop-wise. The reaction was stirred at room temperature for three days after which all volatiles were removed under vacuum. The resulting yellow-orange solid was partially dissolved in warm toluene and filtered. The filtrate was pumped under vacuum to a viscous brown oil. The crude product can be further purified by vacuum distillation.

Example 16

Synthesis of di-titanium bis(2,4-di-tert-butyl-imidazolate)hexaethoxide

To a solution of 1.00 g (4.58 mmol) of TiCl(OEt)$_3$ in 30 mL of THF at −40° C. was added a suspension of 0.85 g (4.58 mmol) 2,5-di-tert-butyl-imidazolate lithium salt in 20 mL of THF drop-wise. The reaction was stirred for 16 hours at room temperature after which all volatiles were removed under vacuum. The resulting foamy brown solid was partially dissolved in hexanes and 0.18 g of an off-white solid was filtered off. The filtrate was pumped down to 1.64 g of a foamy brown-yellow solid. Purification was accomplished by sublimation. The crude yield was 99%.

Figure 3:
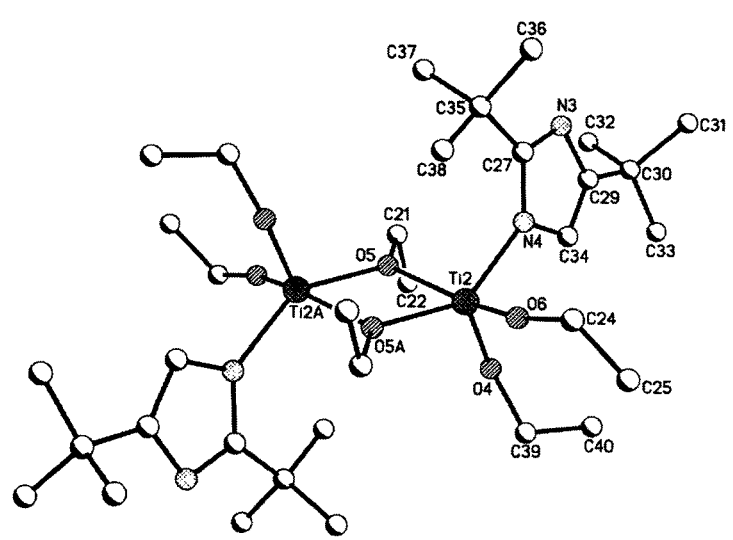
FIG. 3 shows the structure of di-titanium bis(2,4-di-tert-butylimidazolate)hexa(ethoxide), as determined by X-ray crystallography.
Figure 4:
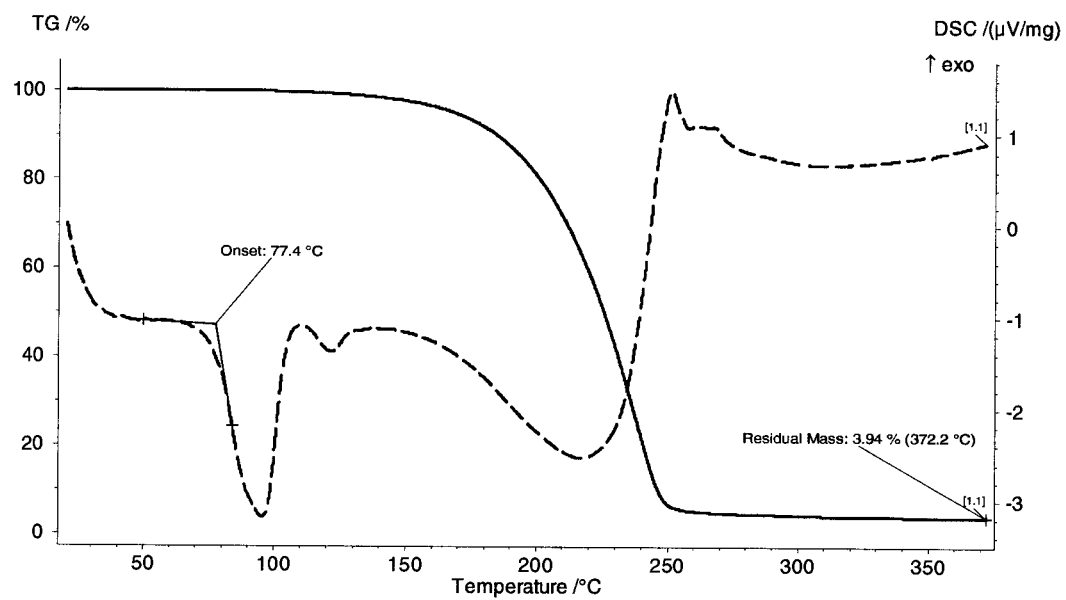
FIG. 4 shows the thermogravimetric analysis/differential scanning calorimetry (TGA/DSC) for di-titanium bis(2,4-di-tert-butylimidazolate)hexa-ethoxide.

A sample of crystalline solid was characterized by X-ray single crystal analysis. The structure shows a dimer wherein each titanium is coordinated to a 2,5-di-tert-butylimidazolate anion ring in an eta-1 fashion. Both titanium centers are also coordinated to a total of six ethoxide anions, two of which bridge both metal centers, see FIG. 3. TGA/DSC showed a melting point of 77.6° C., involatile residue of <4 wt %, see FIG. 4.

$^1$H-NMR (500 MHz, C$_6$D$_6$) δ (ppm): 4.24 (b, 12H, OCH$_2$CH$_3$), 1.67 (s, 18H, imid), 1.65 (s, 18H, imid), 1.04 (b, 18H, OCH$_2$CH$_3$).

Example 17

Synthesis of titanium (2-isopropyl-4,5-di-(1,1-dimethylpropyl)imidazolate)triisopropoxide To a solution of 2.64 g (10.54 mmol) of TiCl(OPr$^i$)$_3$ in 30 mL of THF was added 2.74 g (10.54 mmol) of 2-isopropyl-4,5-di-tert-amyl-imidazolate salt synthesized in situ. Upon addition, the reaction mixture became a vibrant burgundy red. The reaction was stirred at room temperature for 16 hours, after which volatiles were removed under vacuum. The residual was partially dissolved in hexanes and 0.46 g of a white solid was filtered off. The filtrate was pumped down to a red-brown sticky oil and purified via vacuum distillation to obtained 3.26 g of a dark red-brown oil.

$^1$H-NMR (500 MHz, C$_6$D$_6$) δ (ppm): 4.46 (sept, 3H, OCH (CH$_3$)$_2$), 3.47 (sept, 1H, imid), 2.07 (q, 4H, imid), 1.69 (s, 12H, imid), 1.62 (d, 6H, imid), 1.11 (d, 18H, OCH(CH$_3$)$_2$), 1.01 (t, 6H, imid).

Example 18

Synthesis of di-titanium bis(2,4-di-tert-butylimidazolate)hexaisopropoxide

Figure 5:
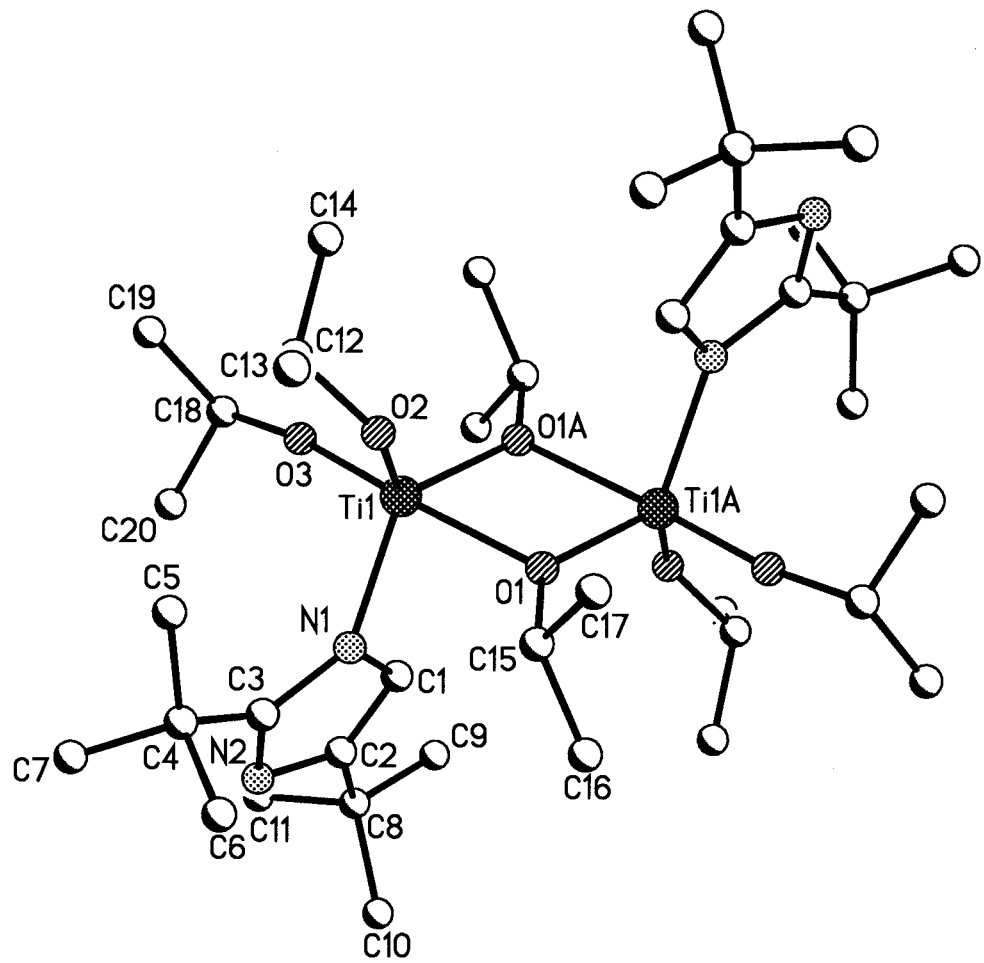
FIG. 5 shows di-titanium bis(2,4-di-tert-butylimidazolate) hexa-isopropoxide, as determined by X-ray crystallography.
Figure 6:
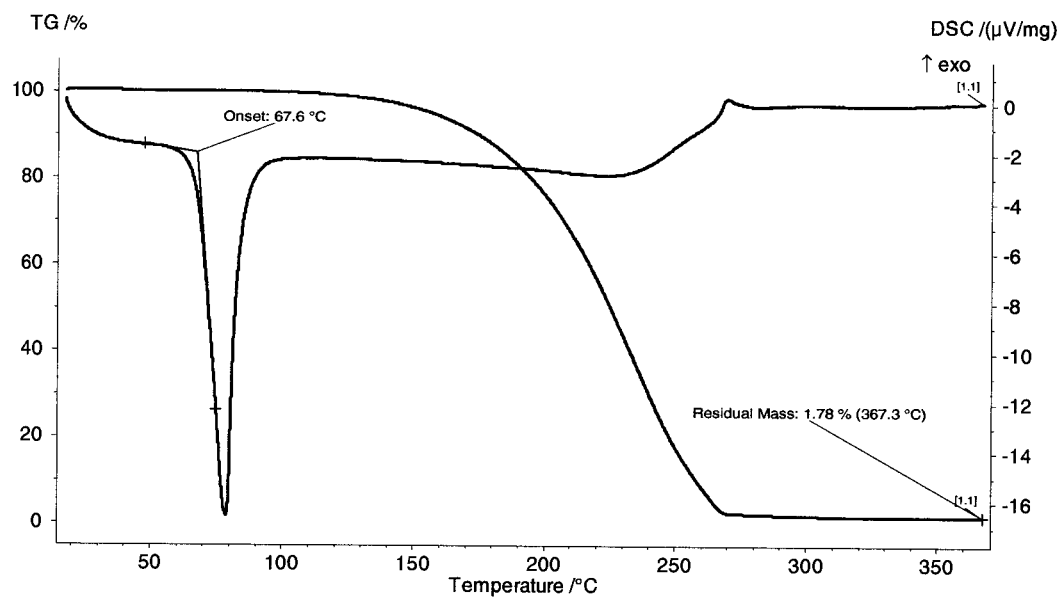
FIG. 6 shows the TGA/DSC for di-titanium bis(2,4-di-tert-butylimidazolate) hexa-isopropoxide.

Under a blanket of dry nitrogen, 0.45 g (2.5 mmoles) of 2,4-di-tertbutylimidazole) dissolved in 10 ml of dry tetrahydrofuran were added, with stirring, to 0.1 g of potassium hydride (2.5 mmoles) in 10 ml of THF. After 20 minutes the evolution of hydrogen ceased leaving a clear yellow solution. This was then added over 5 minutes to 0.65 g (2.5 mmoles) of chlorotriisopropoxytitanium dissolved and stirring in 10 ml of tetrahydrofuran at room temperature. The resulting mixture was then stirred for 1 hour at room temperature after which the solvent was removed by the application of vacuum to yield yellow brown solid. This was sublimed at 140° C. to yield 0.8 g (80%) of bis(2,4-di-tert-butylimidazoly-tri-isopropoxy titanium) as a yellow crystalline solid X-crystallography confirmed it as a dimeric structure where each titanium is coordinated to a 2,5-di-tert-butylimidazolate anion ring in an eta-1 fashion. Both titanium centers are also coordinated to a total of six ethoxide anions, two of which bridge both metal centers, see FIG. 5. Thermogravimetric analysis/differential scanning calorimetry (TGA/DSC) showed a melting point of 67.6° C. and an involatile residue of <2 wt %, see FIG. 6.

$^1$H NMR: (500 MHz, C$_6$D$_6$): δ=1.26 (d, 36H), δ=1.75 (s, 18H), δ=1.84 (s, 18H), δ=4.54 (m, 6H), δ=7.44 (s, 2H).

Example 19

Synthesis of titanium bis(2,5-di-tert-butylimidazolate)diisopropoxide

Figure 7:
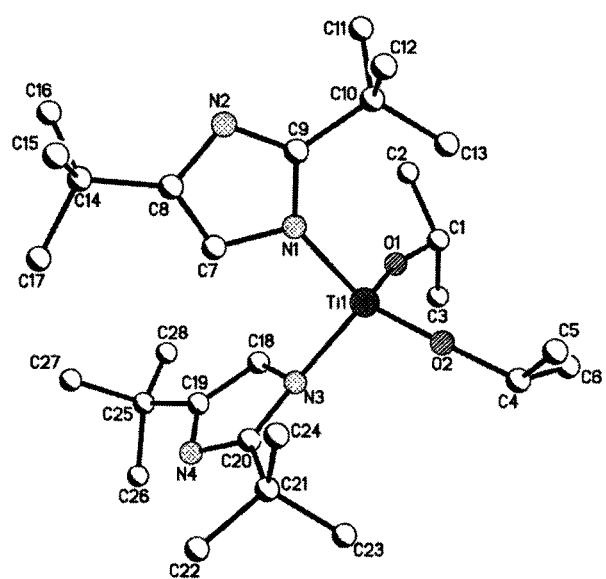
FIG. 7 shows titanium bis(2,4-di-tert-butylimidazolate)bis (isopropoxide), as determined by X-ray crystallography.

To a solution of 12.89 g (49.45 mmol) of TiCl(iPrO)$_3$ in 200 mL of THF was added 9.21 g (49.45 mmol) of 2,5-di-tert-butyl imidazolate lithium salt. The reaction was stirred at room temperature for 16 hours after which all volatiles were removed under vacuum to a yellow solid. The residual was partially dissolved in 200 mL of hexanes and 2.04 g of solid was filtered off. The filtrate was stripped of solvent by vacuum, and the crude bis((2,4-di-tert-butylimidazoly)-tri-isopropoxy titanium) thus formed was then disproportioned to bis(2,5-di-tert-butylimidazolate)bis(isopropoxy)titanium and titanium tetra-isopropoxide by prolonged vacuum distillation at 100 mTorr and >100° C. The titanium tetra-isopropoxide was distilled out as the more volatile fraction leaving the desired product behind. Structure confirmed by X-ray, which shows a monomeric structure where two imidazolate anions coordinate eta-1 to titanium which is also coordinated to two isopropoxide anions, see FIG. 7.

$^1$H-NMR (500 MHz, C$_6$D$_6$) δ (ppm): 7.12 (s, 2H, imid), 4.47 (sept, 2H, OCH(CH$_3$)$_2$), 1.56 (s, 18H, imid), 1.52 (s, 18H, imid), 1.04 (d, 12H, OCH(CH$_3$)$_2$).

Example 20

Synthesis of titanium(2,4,5-tri-tert-butylimidazolate) triisopropoxide

Figure 8:
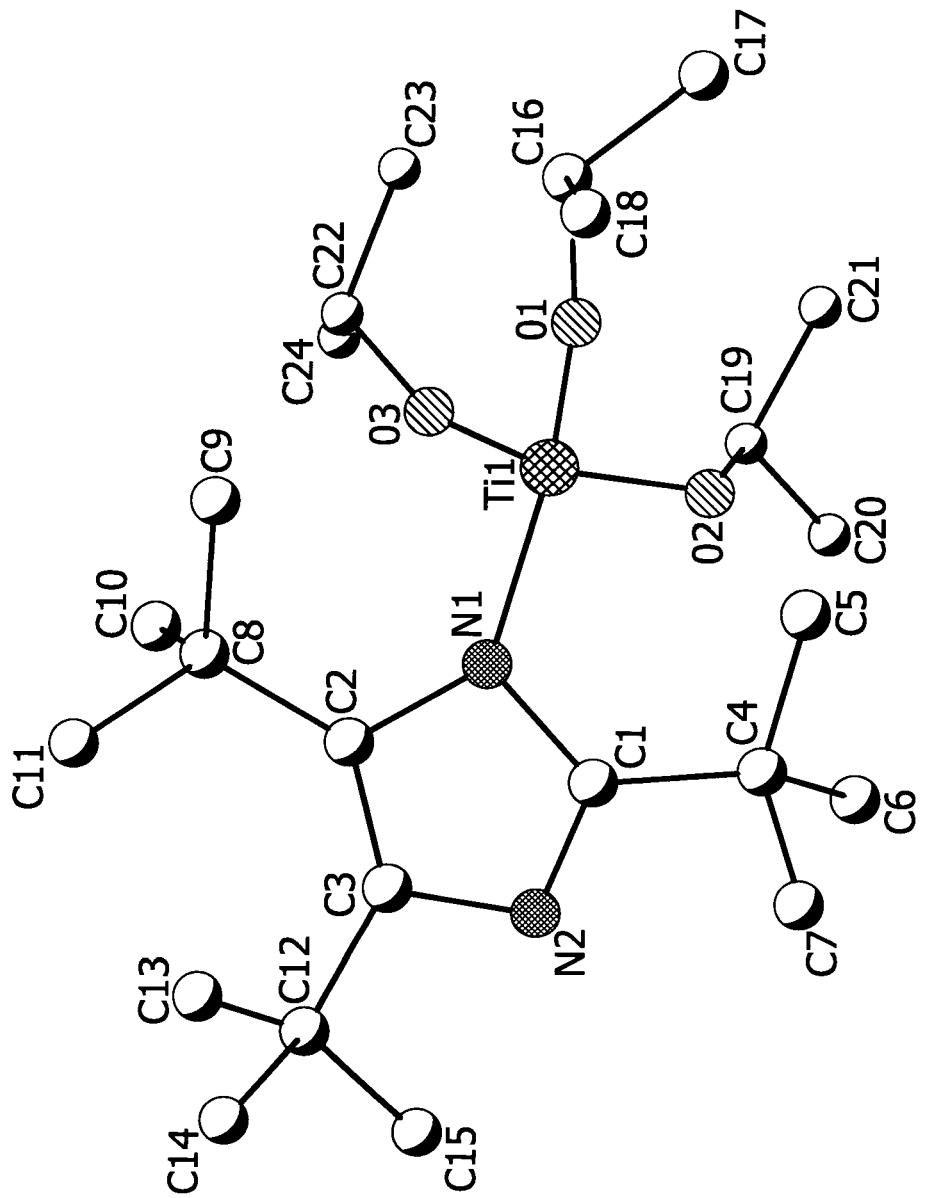
FIG. 8 shows titanium (2,4,5-tri-tert-butylimidazolate)tri-isopropoxide, as determined by X-ray crystallography.
Figure 9:
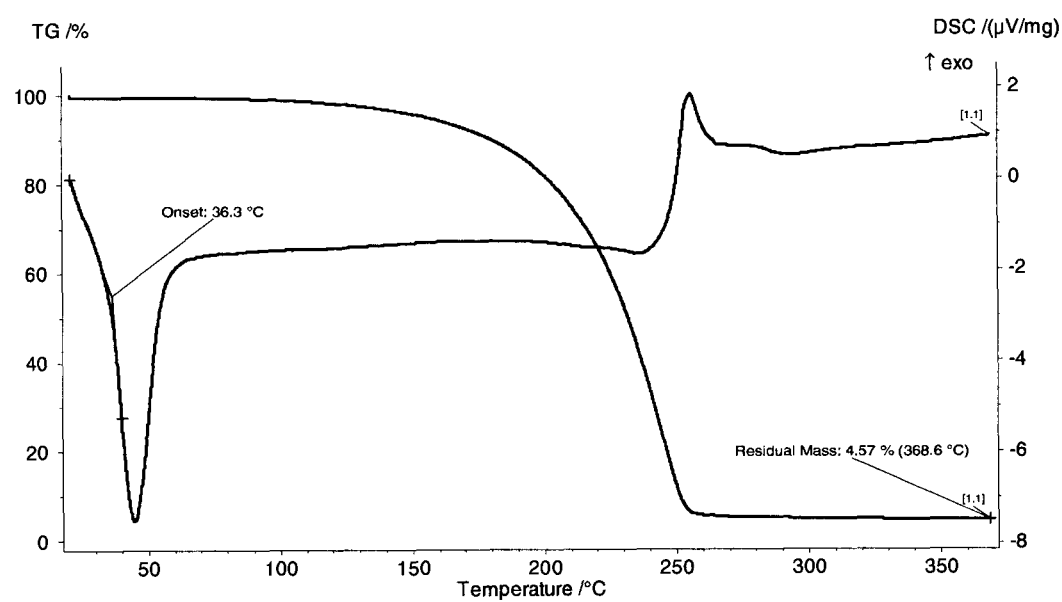
FIG. 9 shows the TGA/DSC for titanium (2,4,5-tri-tert-butylimidazolate)tri-isopropoxide.

Under a blanket of dry nitrogen, 4.72 (20 mmoles) of 2,4,5-tri-tert-butylimidazole) dissolved in 50 ml of dry THF were added, with stirring, to 0.8 g of potassium hydride (20 mmoles) in 50 ml of THF. After 20 minutes, the evolution of hydrogen ceased, leaving a clear solution. This was then added to 5.21 g (20 mmoles) of chlorotriisopropoxytitanium dissolved in 20 ml of THF at room temperature. The resulting mixture was then stirred for overnight at room temperature, after which the solvent was removed by the application of vacuum to yield a yellow orange solid. This was mixed with 100 m of hexane, filtered to yield a golden oil, which solidified upon standing at 4° C. overnight. This crude product was then vacuum distilled at 100 mToo, collecting 6.5 g (71% yield) of pure product at 120-125° C. X-ray crystallography of crystals grown at 4° C. confirmed the structure as a monomer, where the imidazolate anion is coordinated eta-1 to titanium, which is also coordinated to three isopropoxide anions, See FIG. 8. TGS/DSC showed a melting point of 36.3° C. and an involatile residue of <5 wt %, see FIG. 9.

$^1$H NMR: (500 MHz, $C_6D_6$): δ=1.1 (d, 18H), δ=1.7 (s, 18H), δ=1.72 (s, 9H), δ=4.5 (m, 3H).

Example 21

Synthesis of titanium (2,4,5-tri-tert-butyl-imidazolate)trichloride

Solution of 3.50 g (14.83 mmol) of 2,4,6-tri-tert-butyl-imidazole in 10 ml of toluene was added to 22.3 ml of 1M $TiCl_4$ in toluene (22.3 mmol) at RT during ~5 minutes. The solution turned dark and formation of yellow precipitate was observed. The slurry was agitated for 24 hours and large amount of solid was formed. The solid was filtered and washed with 20 ml of toluene. 3.6 g of yellow solid, which was likely a salt of 2,4,6-tri-tert-butyl-imidazolium tri-mu-chlorido-bis[trichloridotitanium(IV)] ($Ti_2Cl_9^-$). Toluene was distilled out from the filtrate under vacuum and residue was dried under vacuum at 80° C. to remove traces of unreacted $TiCl_4$ and 2,4,6-tri-tert-butyl-imidazole (very light yellow solid). The residual material was transferred into 25 ml flask and sublimed under 0.2 torr at 80-100° C. to obtain 1.54 g of deep red solid (27% yield based on 2,4,6-tri-tert-butyl-imidazole).

Thermal gravimetric and differential thermal analyses indicate the material is a volatile solid with mp ~77° C., vapor pressure >1 torr at 150° C. and thermal decomposition temperature above 200° C.

$^1$H-NMR (500 MHz, $d_8$-toluene) δ (ppm): 1.35 (s, 18H), 1.41 (s, 9H); $^{13}$C-NMR (500 MHz, $d_8$-toluene) δ (ppm): 29.5 (3C), 31.3 (6C), 36.8 (2C), 37.0 (1C), 168.0 (2C), 181 (1C).

Example 22

Crystal structure of titanium(2,4,5-tri-tert-butyl-imidazolate)trichloride

Figure 10:
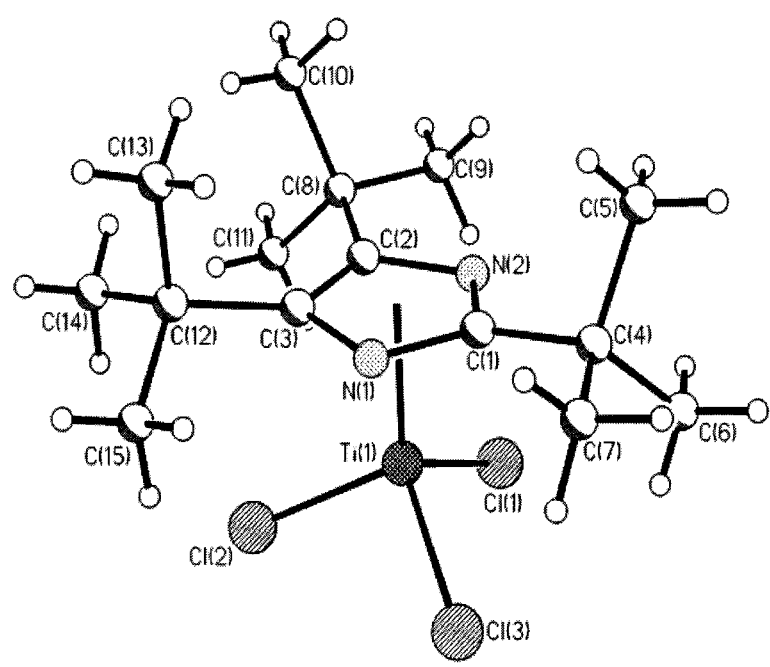
FIG. 10 shows titanium (2,4,5-tri-tert-butylimidazolate) trichloride, as determined by X-ray crystallography.
Figure 13:
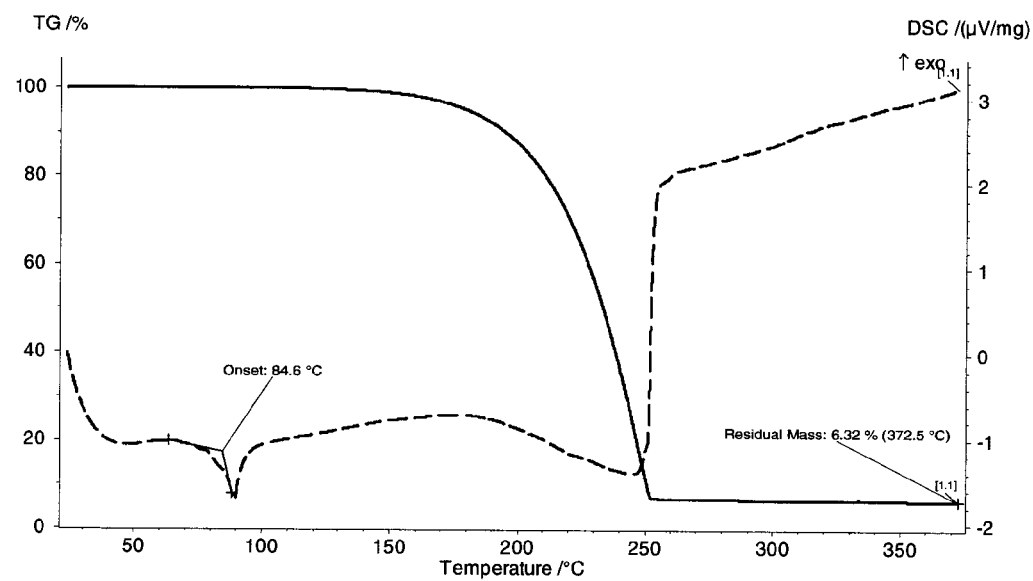
FIG. 13 shows the TGA/DSC for cobalt (2-tert-butyl-4,5-di(1,1-dimethylpropyl)imidazolate)(cyclopentadienide).

Crystals of titanium 2,4,5-tri-tert-butyl-imidazolate trichloride were grown from its solution in octane and characterized by X-ray single crystal analysis. Unexpectedly, the structure (FIG. 13) shows titanium (IV) coordinated to the 2,4,6-tri-tert-butylimidazolate anion in an eta-5 fashion in addition to three chloride anions.
Ti(1)-C(1)-2.2962(18), Ti(1)-N(2)-2.3114(15), Ti(1)-N(1)-2.3192(15), Ti(1)-C(2)-2.3774(17), Ti(1)-C(3)-2.3882(17). See FIG. 10.

Example 23

Synthesis of titanium (2-tert-butyl-4,5-di-(1,1-dimethylpropyl)imidazolate)trichloride Solution of 4.00 g (15.15 mmol) of 2-tert-butyl-4,5-di-tert-pentyl-imidazole in 10 ml of toluene was added to 22.7 ml of 1M $TiCl_4$ in toluene (22.7 mmol) at RT during ~5 minutes. The solution turned dark and formation of yellow precipitate was observed. The slurry was agitated for 24 hours and large amount of solid was formed. The solid was filtered and washed with 20 ml of toluene. 4.45 g of yellow solid, which was likely a salt of 2-tert-butyl-4,5-di-tert-pentyl-imidazolium tri-mu-chlorido-bis[trichloridotitanium(IV)]($Ti_2Cl_9^-$). Toluene was distilled out from the filtrate under vacuum and residue was dried under vacuum at 95° C. to remove traces of unreacted $TiCl_4$ and 2-tert-butyl-4,5-di-tert-pentyl-imidazole (light yellow liquid). The residual material was transferred into 25 ml flask and sublimed under 0.2 torr at 80-100° C. to obtain 1.1 g of deep red solid (17% yield based on 2-tert-butyl-4,5-di-tert-pentyl-imidazole).

Thermal gravimetric and differential thermal analyses indicate the material is a volatile solid with mp ~59° C. and vapor pressure >1 torr at 150° C. and thermal decomposition temperature above 200° C.

$^1$H-NMR (500 MHz, $d_8$-toluene) δ (ppm): 0.54 (t, 6H), 1.44 (s, 9H), 1.45 (s, 6H), 1.49 (s, 6H), 1.60 (q, 2H), 1.64 (q, 2H).

Example 24

Figure 11:
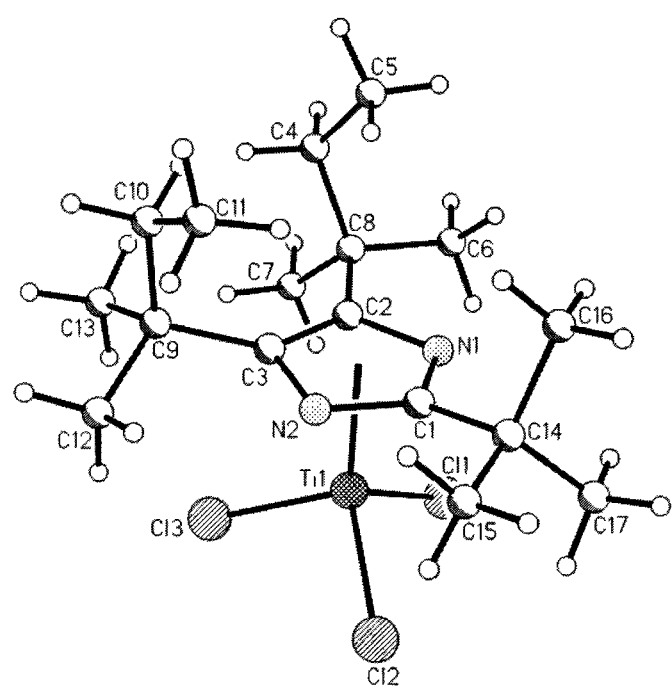
FIG. 11 shows titanium (2-tert-butyl-4,5-(1,1-dimethylpropyl)imidazolate)trichloride, as determined by X-ray crystallography.
Figure 14:
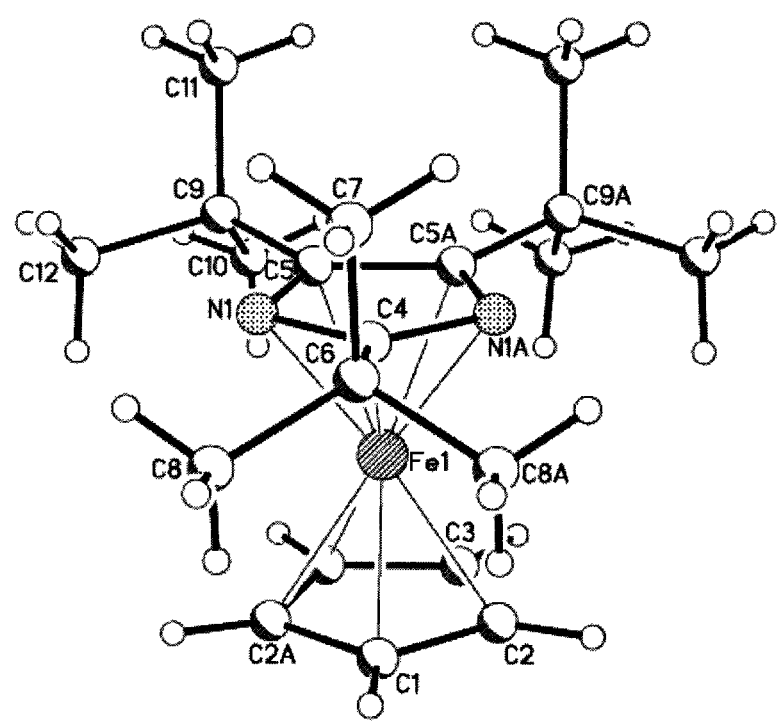
FIG. 14 shows iron (2,4,5-tri-tert-butyl-imidazolate)(cyclopentadienide), as determined by X-ray crystallography.

Crystal structure of titanium-2-tert-butyl-4,5-di-(11,-dimethylpropyl-imidazolate trichloride Crystals of titanium 2,4,5-tri-tert-butyl-imidazolate trichloride were grown from its solution in octane and characterized by X-ray single crystal analysis (See FIG. 14). Unexpectedly, the structure shows titanium (IV) coordinated to 2-tert-butyl-4,5-di-tert-pentyl-imidazolate anion in an eta-5 fashion in addition to three chloride anions: Ti(1)-C(1)-2.2939(15), Ti(1)-N(2)-2.3104(13), Ti(1)-N(1)-2.3136(13), Ti(1)-C(2)-2.3880(16), Ti(1)-C(3)-2.4038(15), see FIG. 11.

Example 25

Synthesis of titanium (2,4,5-tri-tert-butyl-imidazolate)dichloride methoxide

Solution of 0.200 g (0.51 mmol) of titanium 2,4,5-tri-tert-butyl-imidazolate trichloride in 2 ml of $d_8$-toluene was added to 0.08 g (2.11 mmol) of lithium methoxide at RT in a small vail inside nitrogen purged glove box. The slurry was agitated at RT for 16 hours and filtered. Solution analysis by $^1$H and $^{13}$C NMR indicated ~78% conversion into titanium 2,4,5-tri-tert-butyl-imidazolatedichloride methoxide:

$^1$H-NMR (500 MHz, $d_8$-toluene) δ (ppm): 1.41 (s, 9H), 1.42 (s, 18H); 3.98 (s, 3H($OCH_3$ group); $^{13}$C-NMR (500 MHz, $d_8$-toluene) δ (ppm): 29.5 (3C), 31.3 (6C), 36.8 (2C), 37.0 (1C), 74.5 (1C, ($OCH_3$), 163.2 (2C), 175 (1C).

Example 26

Synthesis of titanium(2,4,5-tri-tert-butyl-imidazolate) chloride dimethoxide

To a Solution of 0.500 g (1.28 mmol) of 2,4,5-tri-tert-butyl-imidazolyltitanium trichloride in 7 ml of toluene was added to 0.235 g (6.2 mmol) of lithium methoxide at RT. The slurry was agitated at RT for 2 days followed by 16 hours at 50° C. During the treatment the color of the slurry changed from deep red to yellow. Mixture of lithium methoxide and lithium chloride was filtered off and solvent was distilled under vacuum at 50° C. Residue analysis by $^1$H and $^{13}$C NMR indicated presence of a mixture of 2,4,5-tri-tert-butyl-imidazolyltitanium dichloride methoxide (~13 mol %) and 2,4,5-tri-tert-butylimidazolyltitanium chloride dimethoxide (~87 mol %):

$^1$H-NMR (500 MHz, d$_8$-toluene) δ (ppm): 1.40 (s, 9H), 1.48 (s, 18H); 4.05 (s, 6H(OCH$_3$ group); $^{13}$C-NMR (500 MHz, d$_8$-toluene) δ (ppm): 29.7 (3C), 31.8 (6C), 36.4 (2C), 36.2 (1C), 69.5 (2C, (OCH$_3$), 157.0 (2C), 170 (1C).

Example 27

Synthesis of zirconium(2,4,5-tri-tert-butyl imidazolate)tri(dimethylamide)

In a N$_2$-purged glove box a 100 mL, 3-neck RB flask equipped with a magnetic stir bar, gas inlet tube, thermocouple, and reflux condenser was charged with tetrakis(dimethylamino)zirconium (2.0 g, 7.5 mmol) and 20 mL anhydrous toluene. 2,4,5-tri-tert-butyl-imidazole (1.94 g, 8.2 mmol) was dissolved in 20 mL of anhydrous toluene and mixed directly with the zirconium precursor solution at room temperature. The reactotion flask was moved to a nitrogen-purged Schlenk line. The mixture was refluxed for 16 hours with a purge of 1 mL/min of dry nitrogen through the gas inlet tube. The toluene was removed under vacuum and the reaction was further heated between 110° C. and 120° C. for an additional 9 hours with a 1 mL/min nitrogen purge through the gas inlet tube. Volatile products were removed at 100 mTorr and 60° C. The product was transferred to a sublimation unit where unreacted TDMAZ and 2,4,5-tri-tert-butyl-imidazole were removed at bath temperatures ranging from 50° C. to 100° C. at 40 mTorr pressure. The cold finger was replaced and the product was isolated by further sublimation onto an air-cooled finger at bath temperatures ranging from 120° C. to 140° C. at 30 mTorr pressure 1.7 g (50% isolated yield) of a white, crystalline-solid product.

NMR (d$_8$-toluene): $^1$H –1.47 (s, 18H), 1.48 (s, 9H), 2.99 (s, 18H); $^{13}$C{$^1$H} –30.35 (3C), 302.65 (6C), 35.50 (2C), 36.46 (2C), 45.53 (6C, —N(CH$_3$)$_2$), 151.16 (2C), 168.53 (1C).

Thermal gravimetric and differential thermal analyses indicate that the material is a volatile solid with mp ~230° C. and vapor pressure >1 torr at 200° C.

Example 28

Synthesis of cobalt(2,4,5-tri-tert-butylimidazolate) (cyclopentadienide)

Figure 12:
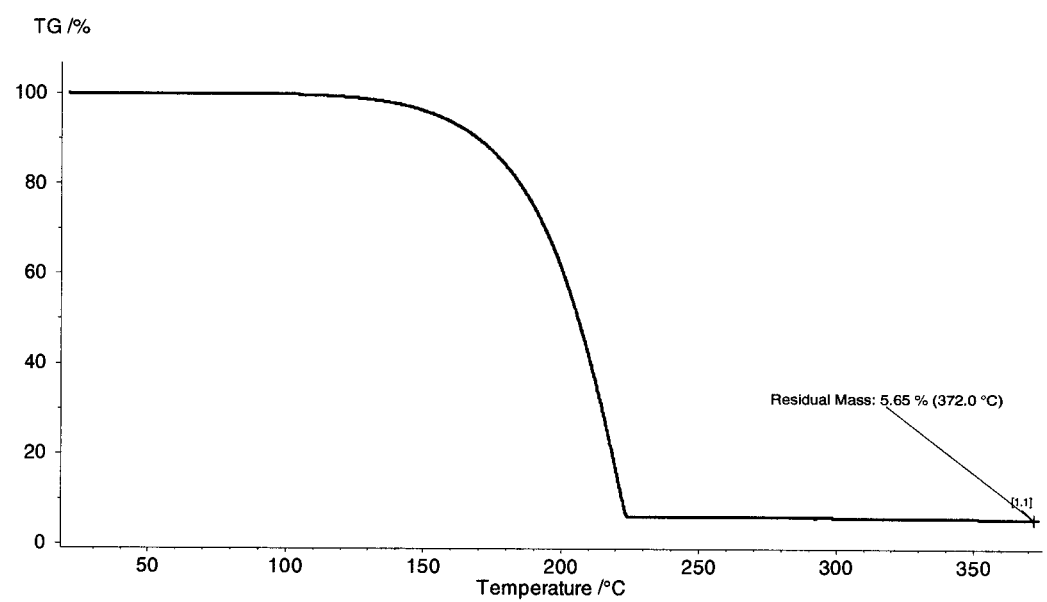
FIG. 12 shows the TGA/DSC for cobalt (2,4,5-tri-tert-butylimidazolate)(cyclopentadienide).

Under a blanket of nitrogen, 2.36 g (10 mmoles) of 2,4,5-tri-tert-butylimidazole dissolved in 20 ml of THF were added to 0.4 g (10 mmoles) of potassium hydride stirring in 80 ml of THF. When the bubbling of released hydrogen ceased, 1.3 g (10 mmoles) of anhydrous cobalt dichloride were added and the resulting mixture stirred overnight at room temperature. 5.0 ml of 2.0M sodium cyclopentadienyl in THF (10 mmoles) were then added and the mixture again stirred overnight at room temperature. The THF was then removed by vacuum, 100 ml of hexane added with mixing and the resulting suspension filtered and the hexane then removed by vacuum to yield the crude product as a dark reddish brown paste. This was then vacuum distilled at 100 mTorr and 2.19 g of product was collected at 120-140° C. (61% yield), structure confirmed by GCMS showing the parent ion at 359 mu. Elemental analysis carbon=65.87 wt % (vs 66.85 theoretical), hydrogen=9.19 wt % (vs 8.91 theoretical), nitrogen=7.77 wt % (vs 7.80 theoretical). TGA showed an involatile residue of <6 wt %, see FIG. 12

Example 29

Synthesis of cobalt (2-tert-butyl-4,5-di(1,1-dimethyl-propyl)imidazolate)(cyclopentadienide)

Under a blanket of nitrogen, 2.5 g (8.3 mmoles) of potassium 2-tert-butyl-4,5-di-tert-amylimidazoyl were dissolved in 50 ml of THF and 1.07 g (8.3 mmoles) of anhydrous cobalt chloride were added and stirred overnight at room temperature. To this mixture, 4.0 ml (8.3 mmoles) of 2.0M sodium cyclopentadienyl in THF was added and the resulting mixture stirred overnight at room temperature. The THF was then removed by vacuum, 100 ml of hexane added with mixing and the resulting suspension filtered and the hexane then removed by vacuum to yield the crude product as a dark reddish brown paste. This was then vacuum distilled at 100 mTorr and 2.05 g of product was collected at 120-140° C. (64% yield), structure confirmed by GCMS showing the parent ion at 387 mu. TGS/DSC showed a melting point of 84.6 C and an involatile residue of <7 wt %, see FIG. 13.

Example 30

Synthesis of iron (2,4,5-tri-tert-butylimidazoate)(cyclopentadienide)

Figure 15:
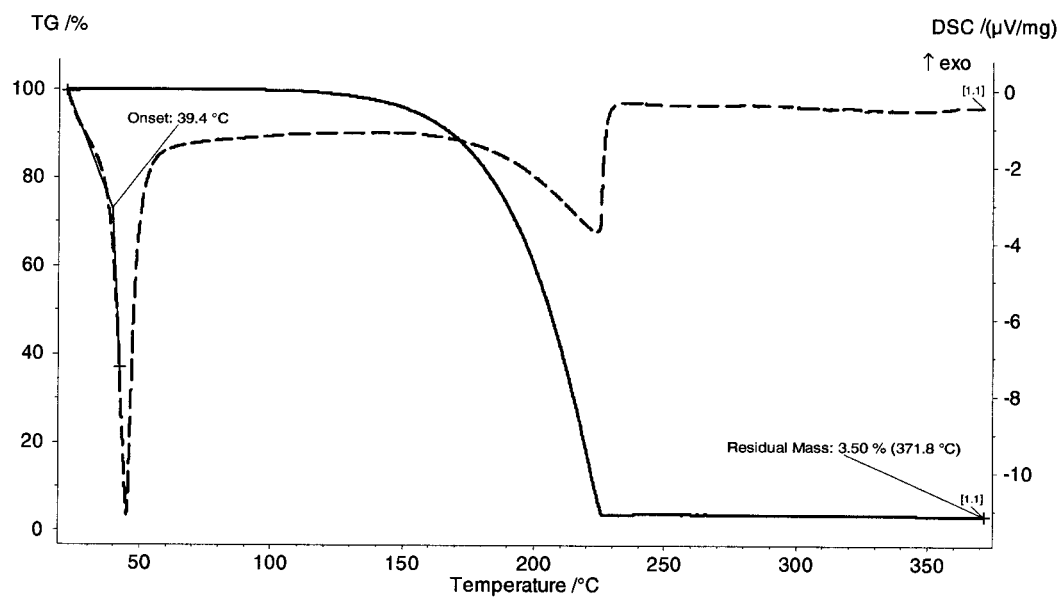
FIG. 15 shows the TGA/DSC for iron (2,4,5-tri-tert-butyl-imidazolate)(cyclopentadienide).

Under a blanket of nitrogen, 1.18 g (5 mmoles) of 2,4,5-tri-tert-butylimidazole in 10 ml of THF were added to 0.2 g (5 mmoles) of potassium hydride stirring in 10 ml of THF. After the hydrogen evolution ceased, 0.64 g (5 moles) of anhydrous iron dichloride were added and the resulting mixture stirred overnight. 2.5 ml of 2.0M of sodium cyclopentadienyl in THF (5 mmoles) were then added and the mixture stirred for 30 minutes. The solvent was then removed under vacuum and the crude product distilled out of the crude product as 0.91 g (51% yield) of an orange semisolid paste. This product was then redistilled under vacuum to yield an orange red oil that crystallized, structure confirmed by X-ray crystallography, which showed the complex to be a monomer with both the 2,4,5-tri-tert-butylimidazolate and pentamethylcyclopentadienide anions to be coordinated eta-5 to the iron center, see FIG. 14. TGA/DSC showed a melting point of 39.4° C. with an involatile residue <4.0 wt %, see FIG. 15.

Example 31

Synthesis of ruthenium (2,4,5-trimethylimidazolate) (pentamethylcyclopentadienide)

To a solution of 0.20 g (0.74 mmol) chloro(pentamethyl-cyclopentadienyl)ruthenium(II) tetramer in 3 mL THF at room temperature was added 0.09 g (0.74 mmol) 2,4,5-trimethylimidazolate lithium salt dissolved in 2 mL of THF dropwise. Reaction mixture was stirred for several weeks after which volatiles were removed under vacuum. Isolated a brown solid that was loaded into a sublimer and heated to 125° C. under 150 mTorr vacuum. A total of 0.18 g of a yellow crystalline solid was collected from the sublimer cold finger and walls. The yield was 69%.

Figure 16:
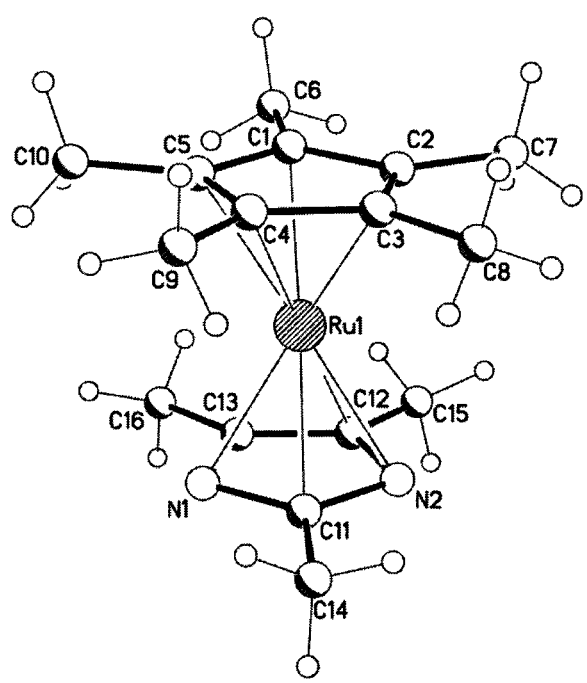
FIG. 16 shows ruthenium (2,4,5-tri-methylimidazolate) (pentamethylcyclopentadienide), as determined by X-ray crystallography.
Figure 17:
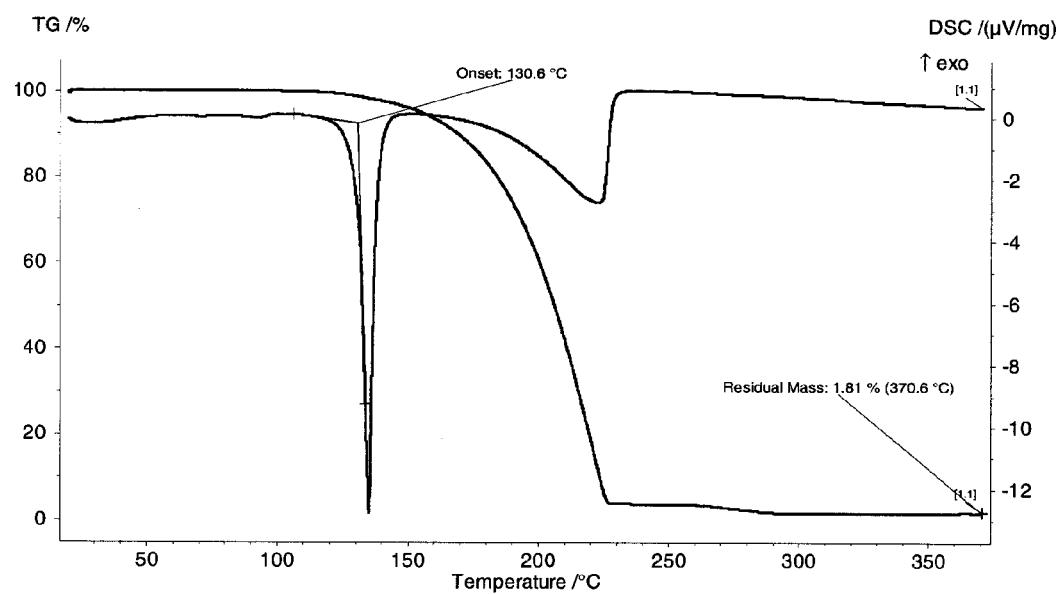
FIG. 17 shows the TGA/DSC for ruthenium (2,4,5-tri-methylimidazolate)(pentamethylcyclopentadienide).

A sample of crystalline solid was characterized by X-ray single crystal analysis. The structure shows a monomeric ruthenium complex, where the metal center is coordinated to both the 2,4,5-trimethylimidazolyl ring and the pentamethylcyclopentadienyl ring in i fashion, see FIG. 16. TGA/DSC showed a melting point of 130.6° C. and an involatile residue of <2 wt %, see FIG. 17.

$^1$H-NMR (500 MHz, $C_6D_6$) δ (ppm): 2.36 (s, 3H), 1.93 (s, 6H), 1.66 (s, 15H).

Example 32

Synthesis of ruthenium (2-ethyl-4-methylimidazolate)(pentamethylcyclopentadienide)

To a solution of 0.25 g (0.92 mmol) chloro(pentamethylcyclopentadienyl)ruthenium(II) tetramer in 7 mL THF at room temperature was added 0.11 g (0.92 mmol) 2-ethyl-4-methylimidazolate lithium salt directly. Reaction mixture was stirred for 16 hours, after which volatiles were removed under vacuum. Isolated a burgundy foam that was extracted with hexanes and filtered. Filtrate was pumped under vacuum to 0.22 g of an oil that quickly solidified. Loaded solid into a sublimer and heated to 125° C. under 150 mTorr vacuum. A yellow crystalline solid was collected from the sublimer cold finger. The yield was 69%, based off of crude.

$^1$H-NMR (500 MHz, $C_6D_6$) δ (ppm): 5.42 (s, 1H), 2.75 (q, 2H), 1.92 (s, 3H), 1.70 (s, 15H), 1.39 (t, 3H).

Figure 18:
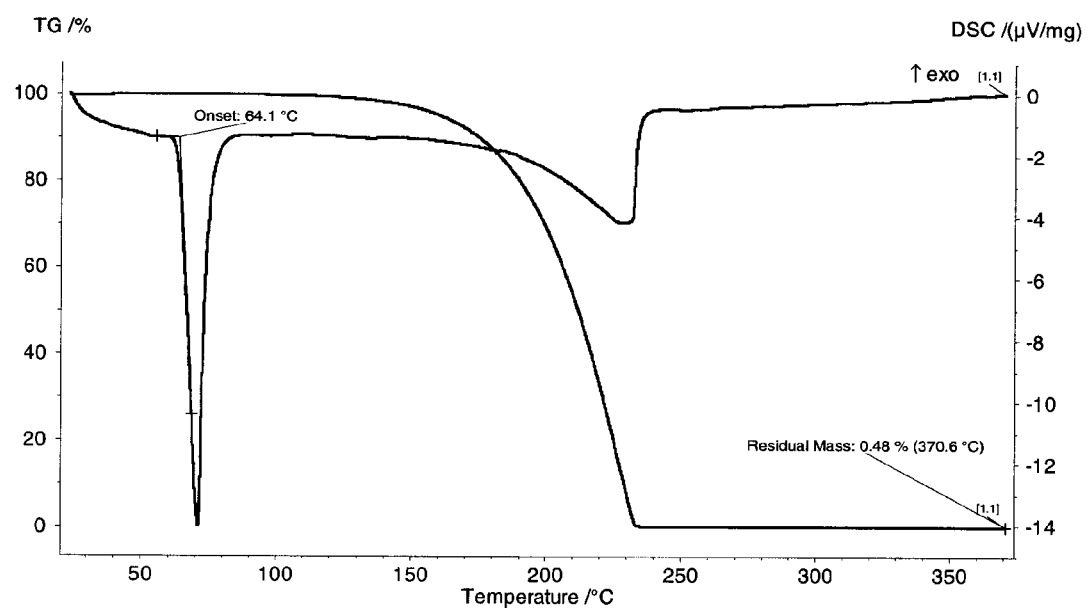
FIG. 18 shows the TGA/DSC for ruthenium (2-ethyl-4-methylimidazolate)(pentamethylcyclopentadienide).

TGA/DSC showed a melting point of 64.1° C. and an involatile residue of <1.0 wt %, see FIG. 18.

Example 33

Synthesis of ruthenium (2-tert-butyl-4-methyl-5-ethylimidazoate)I(pentamethylcyclopentadienide)

To a solution of 0.25 g (0.92 mmol) chloro(pentamethylcyclopentadienyl)ruthenium(II) tetramer in 7 mL THF at room temperature was added 0.16 g (0.92 mmol) 2-tert-butyl-4-methyl-5-ethylimidazolate lithium salt directly. Reaction mixture was stirred for 16 hours, after which volatiles were removed under vacuum. Isolated a dark brown waxy solid that was extracted with hexanes and filtered. Filtrate was pumped under vacuum to 0.27 g of a brown solid. Loaded solid into a sublimer and heated to 85° C. under 150 mTorr vacuum. A yellow crystalline solid was collected from the sublimer cold finger. The yield was 73% based off of crude.

Figure 19:
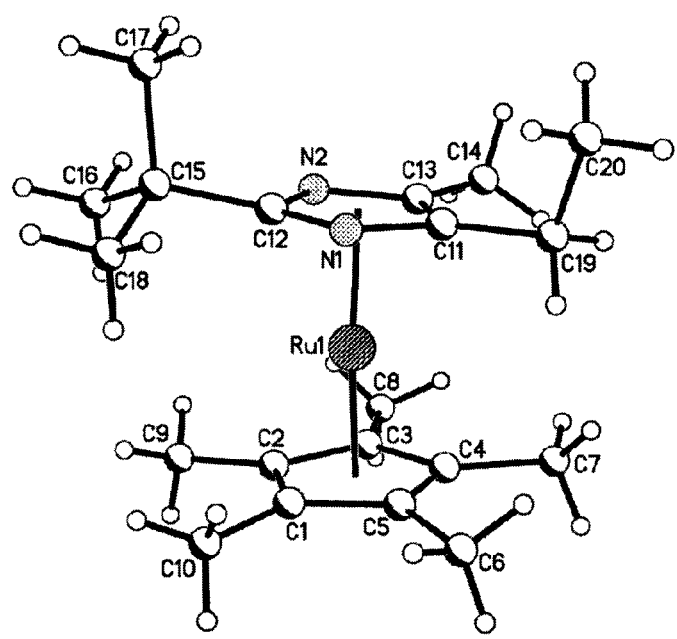
FIG. 19 shows ruthenium (2-tert-butyl-4-methyl-5-ethylimidazolate)(pentamethylcyclopentadienide), as determined by X-ray crystallography.
Figure 20:
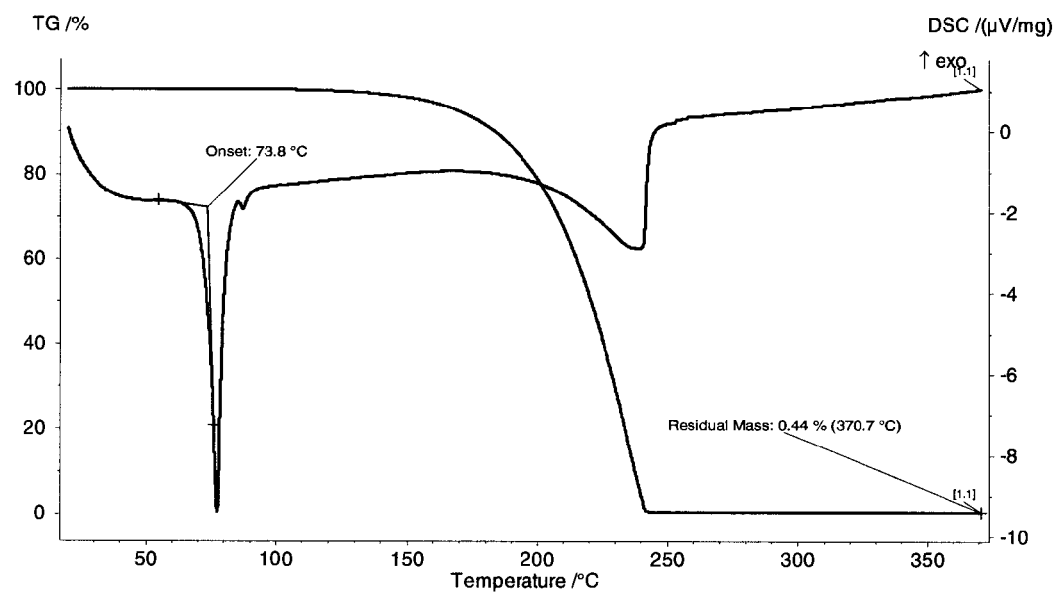
FIG. 20 shows the TGA/DSC for ruthenium (2-tert-butyl-4-methyl-5-ethylimidazolate)(pentamethylcyclopentadienide).

A sample of crystalline solid was characterized by X-ray single crystal analysis. The structure shows a monomeric ruthenium complex with the metal center coordinated to both the 2-tert-butyl-4-methyl-5-methylimidazolate and pentamethylcyclopentadienide anions ring and the pentamethylcyclopentadienyl ring in an eta-5 fashion, see FIG. 19. TGA/DSC showed a melting point of 73.8° C. and an involatile residue of <1.0 wt %, see FIG. 20.

$^1$H-NMR (500 MHz, $C_6D_6$) δ (ppm): 2.23 (q, 2H), 1.88 (s, 3H), 1.65 (s, 15H), 1.50 (s, 9H), 1.12 (t, 3H).

Example 34

Synthesis of ruthenium (2-tert-butyl-di(1,1-dimethylpropyl)imidazolate) (pentamethylcyclopentadienide)

Figure 21:
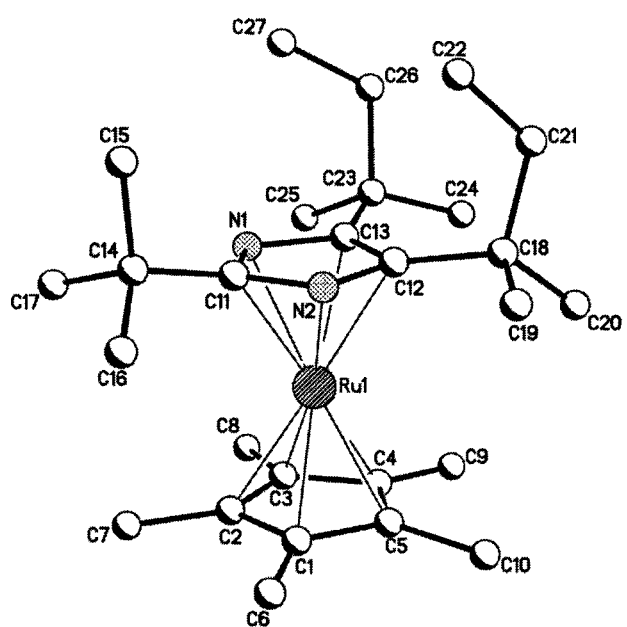
FIG. 21 shows ruthenium (2-tert-butyl-4,5-di-(1,1-dimethyl)imidazolate)(pentamethylcyclopentadienide), as determined by X-ray crystallography.

1.1 g (37 mmoles) of potassium(2-tert-butyl-4,5-di(1,1-dimethylpropyl)imidazolate) dissolved in 25 ml of THF were added to 1 g (0.0037 moles) of ruthenium (pentamethylcyclopentadienide) chloride dissolved in 75 ml of dry THF and the resulting mixture stirred overnight at room temperature. The solvent was then removed by vacuum, 100 ml of dry hexane then added and the resulting mixture thoroughly stirred then filtered. The hexane was then removed by vacuum to yield 1.13 g of crude ruthenium (2-tert-butyl-di(1,1-dimethylpropyl)imidazolate). (pentamethylcyclopentadienide). Structure confirmed by GCMS, parent ion detected at 499 mu. The structure was also confirmed by X-ray structural analysis of a sample of crude material which was sublimed then recrystallized from hexane. This shows the imidazolate and cyclopentadienide anions to both be coordinated eta-5 to ruthenium, see FIG. 21.

Example 35

Synthesis of ruthenium(pentamethylcyclopentadienide)(imidazolate)

To a suspension of 0.50 g (1.84 mmol) of ruthenium(II)(pentamethylcyclopentadienide) chloride tetramer in a mixture of 16 mL of THF and hexanes was added 0.21 g (1.84 mmol) lithium imidazolate. The reaction mixture turned a deep purple and was refluxed for 16 hours after which all volatiles were removed under vacuum. The residual solid was partially dissolved in warm hexanes and 0.25 g of a dark purple solid was filtered off. Solvent was removed from the hexane by vacuum to yield a purple foam-like solid weighing 0.13 g. Analysis of the filtrate by $^1$H-NMR showed many impurities. TGA of the insoluble solid showed a residual mass of 75%.

Example 36

Figure 22:
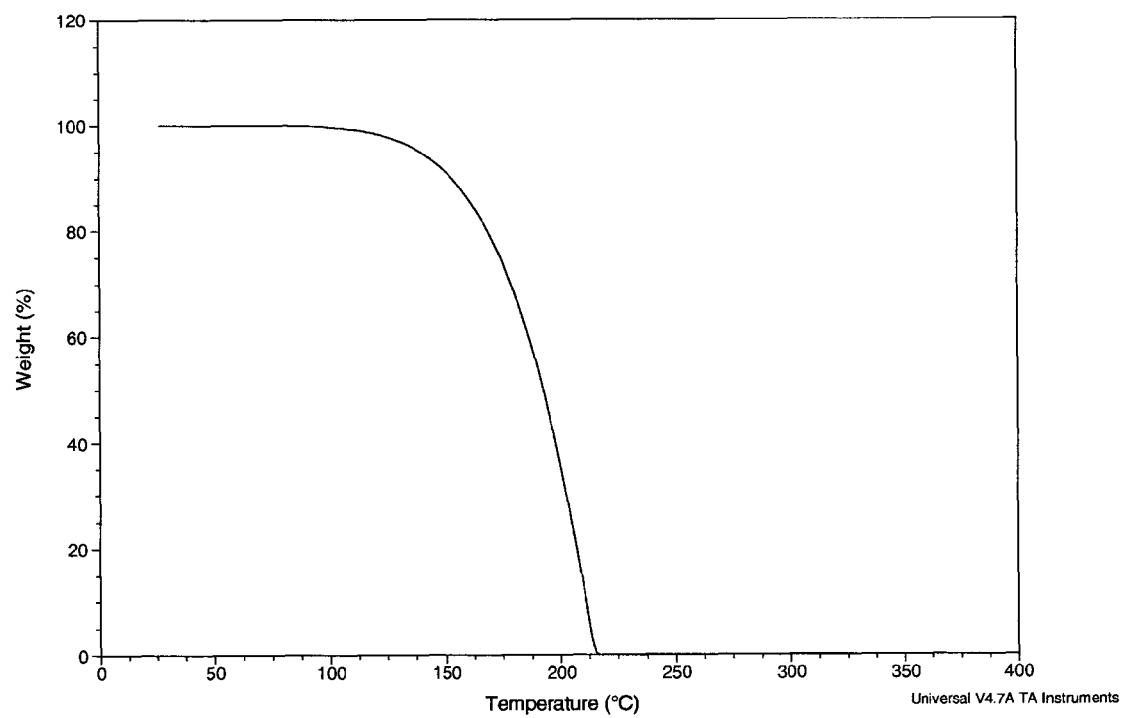
FIG. 22 shows the TGA/DSC for manganese (2-tert-butyl-4,5-di-(1,1-dimethylpropyl)imidazolate tricarbonyl.

Synthesis of manganese(2-tert-butyl-4,5-di-(1,1-dimethylpropyl)-imidazolate)I tricarbonyl Inside a nitrogen-purged glove box a 14/20 3-neck, 100 mL round bottom flask with a magnetic PTFE stir bar was charged with the 4.81 g (17.5 mmol) of 2-tert-butyl-4,5-di-tert-pentyl-imidazole and 50 ml of hexanes. The flask was fitted with a vacuum takeoff, pressure-equalizing drop funnel, and a rubber septum. The setup was moved to a nitrogen-purged Schlenk manifold where the contents were cooled to −40° C. in a cold acetone bath. 11.9 ml of 1.6 M solution of n-butyllithium in hexane (19.0 mmol) were added drop-wise via syringe over 15 minutes with rapid stirring wherein no temperature changes or exothermic activity were observed. The resulting solution was stirred at low temperature for one hour, then allowed to warm to room temperature by removing the cold bath. Upon standing for an additional hour, the solution remained colorless, but became very thick with a consistency similar to honey. The solution was cooled to 0° C. and treated drop-wise over 30 minutes with the solution of 5.00 g (18.2 mmol) of manganese pentacarbonyl bromide dissolved in 30 ml of anhydrous THF, and loaded to the drop funnel. The resulting mixture was allowed to warm to room temperature and stir for 16 hours. Under a nitrogen purge, the drop funnel was replaced with a ground-glass plug and the septum with a short-path distillation column. At a pressure of ~200 torr, the majority of the solvent was distilled into a receiver using a bath temperature of ~50° C. The receiver was exchanged with a clean, dry udder and the remaining solvent was removed under full vacuum. The distillation was continued under full vacuum (~50 mTorr) where at a bath temperature of 80-100° C. unreacted yellow-crystalline $BrMn(CO)_5$ was removed by sublimation. Distillation column was exchanged with a short path condenser and the vacuum takeoff was replaced with a glass plug. The bath was heated to 125° C. where over 2-3 hours an orange-red crystalline solid was distilled out and crystallized on the cold parts of condenser and receiver. 3.07 g (47 isolated yield) of manganese 2-tert-butyl-4,5-di-(1,1-dimethylpropyl)-imidazolate tricarbonyl was collected. IR (v (CO))=1960 and 2030 cm$^{-1}$. $^1$H NMR (d$_8$-toluene): 0.66 (t, 6H), 1.33 (s, 6H), 1.35 (s, 9H), 1.41 (m, 2H), 1.44 (s, 6H), 1.59 (m, 2H); $^{13}$C NMR (d$_8$-toluene): 9.28 (2C), 28.29 (2C), 29.66 (3C), 31.22 (2C), 32.74 (1C), 36.54 (2C), 36.81 (2C), 132.64 (2C), 144.01 (1C), 224.3 (3C(CO)). TGA (conditions 90 ccm of N$_2$ and 10° C./min heating rate) showed an involatile residue of <0.5 wt % and an estimated vapor pressure above 1 torr at 150° C., see FIG. 22.

Example 37

Figure 23:
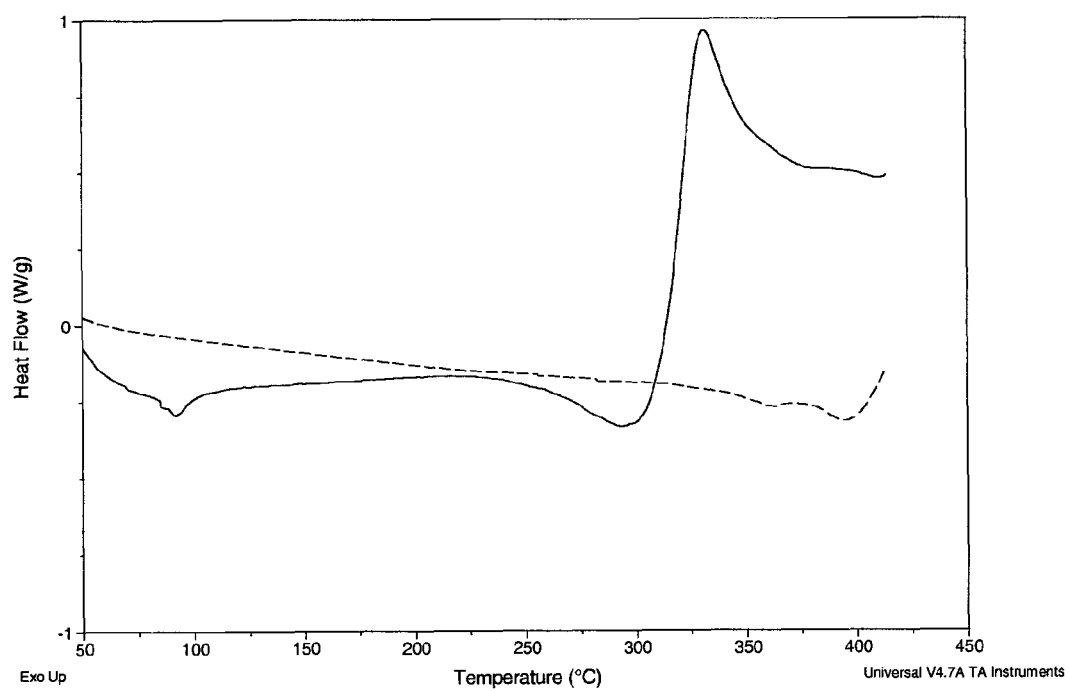
FIG. 23 shows DSC for manganese (2-tert-butyl-4,5-di-(1,1-dimethylpropyl)imidazolate tricarbonyl (solid line) superimposed with the DSC for manganese (methylcyclopentadienide)tricarbonyl (dashed line).

Differential scanning calorimetry of manganese(2-tert-butyl-4,5-di-(1,1-dimethylpropyl)-imidazolate)1 tricarbonyl In a sealed pressure capsule at 10 C/min heating rate indicated an onset on endothermal decomposition around 250° C. Lower onset of thermal decomposition manganese(2-tert-butyl-4,5-di-(1,1-dimethylpropyl)-imidazolate)tricarbonyl compare to prior art manganese tricarbonyl complex manganese (methycyclopentadieide0 tricarbonyl, onset of decomposition >300° C.) suggests higher reactivity of manganese imidazolate complexes of this invention in chemical vapor deposition reactions. FIG. 23 shows the thermal gravimetric analysis of manganese(2-tert-butyl-4,5-di-(1,1-dimethylpropyl)-imidazolate)I tricarbonyl (solid) and manganese(methylcyclopentadienide)tricarbonyl (dashed).

Example 38

Reactivity of manganese(2-tert-butyl-4,5-di-(1,1-dimethylpropyl)-imidazolate)tricarbonyl toward hydrogen 10 ml SS vessel was charged with 2.1 g of manganese 2-tert-butyl-4,5-di-tert-pentyl-imidazolate tricarbonyl and 121 psi of hydrogen. The vessel was heated to 250° C. at 2° C./min heating rate followed by 12 hour isothermal heating at 250° C. Pressure increase due to release of gas was observed during isothermal heating at 250° C. After cooling the reaction vessel to RT residual sample pressure was much higher than initial sample pressure (250 psig) indicating release of carbon monoxide from the sample at 250° C. GC analysis of the gases evolved during the experiment also indicated presence of carbon monoxide. No reaction between the prior art manganese tricarbonyl complex (manganese methycyclopentadienide tricarbonyl) and hydrogen was observed under identical condition as unchanged methylcyclopentadienyl-manganese tricarbonyl was recovered after heating under 145 psi of hydrogen for 16 hours at 250° C.

Example 39

Synthesis of lanthanum (2-tert-butyl-4,5-di-(1,1-dimethylpropyl)imidazolate)diiodide bis(tetrahydrofuran)

Lanthanum (III) iodide (1.0 g, 0.002 mol) was stirred in 50 mL of THF for 30 mins at room temperature. Potassium 2-tert-butyl-4,5-di-(1,1-dimethylpropyl)imidazolate (0.6 g, 0.002 mol) was added, and the resulting mixture was refluxed for 60 hours. THF was removed by vacuum, followed by hexane extraction, then filtration. The hexane was removed by vacuum, and the resulting solid was crystallized to isolate the final product.

Yield=1.18 g, 26.3%
NMR: 4.25 (4H, s), 1.70 (4H, q), 1.633 (21H, s), 1.415 (4H, m), 0.725 (6H, t).

Figure 24:
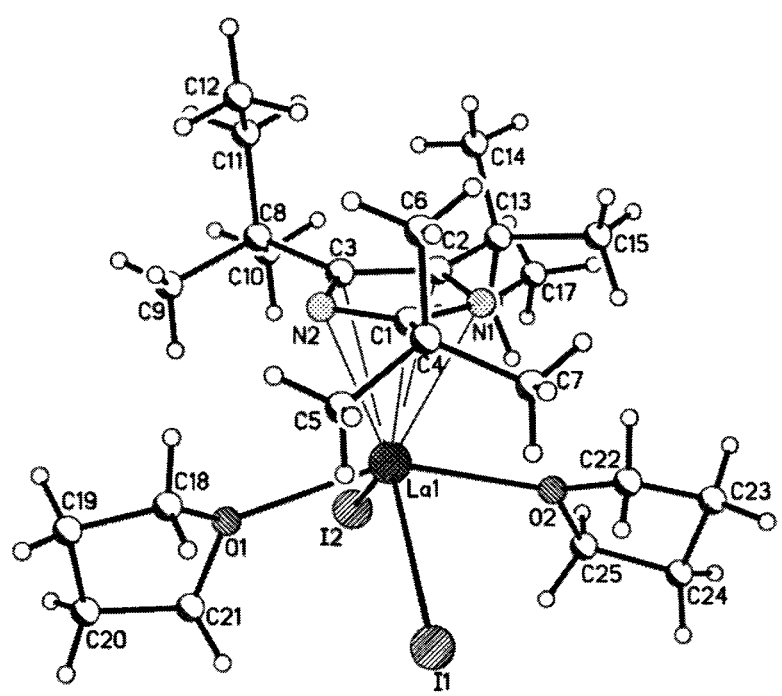
FIG. 24 shows lanthanum(2-tert-butyl-4,5-di-(1,1-dimethylpropyl)imidazolate)di-iodide bis(tetrahydrofuran), as determined by X-ray crystallography.

Structural determination by X-ray analysis showed a monomeric lanthanum complex where the metal center is coordinated to the 2-tert-butyl-4,5-di-(11-dimethylpropyl) imidazolate anion in an eta-5 fashion along with two iodide anions and two molecules of tetrahydrofuran, see FIG. 24.

Example 40

Synthesis of Cerium 2-tert-butyl-4,5-di(1,1-dimethylpropyl)imidazolate diiodide bis(tetrahydrofuran)

Cerium (III) iodide (2.0 g, 0.0038 mol) was stirred in 50 mL of dry THF for 30 mins at room temperature. Potassium 2-tert-butyl-4,5-di(1,1-dimethylpropyl)imidazolate (1.15 g, 0.0038 mol) was added, and the resulting mixture was refluxed for 90 hours. The solvent was removed by vacuum, followed by hexane extraction of the resulting solid. The hexane was removed by vacuum to yield the final product.

Figure 25:
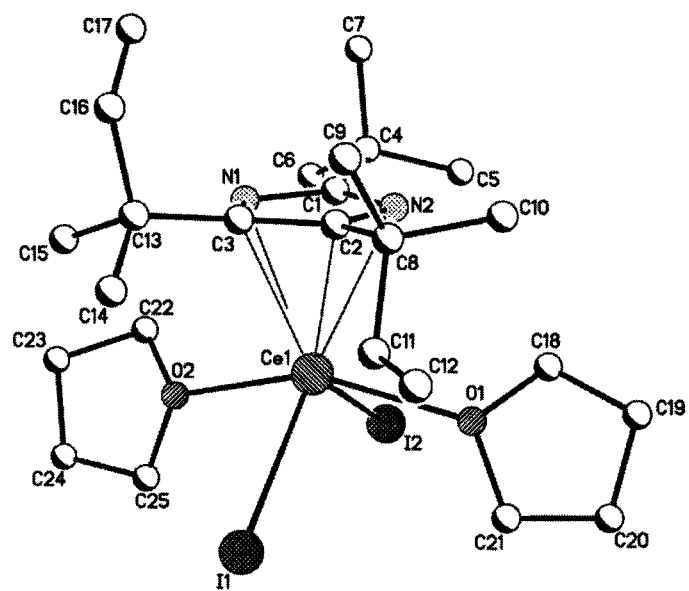
FIG. 25 shows cerium(2-tert-butyl-4,5-di-(1,1-dimethylpropyl)imidazolate)di-iodide bis(tetrahydrofuran), as determined by X-ray crystallography.

Yield=1.18 g, 47%. X-ray crystallography of the final product recrystallized from hexane showed it to be a monomer with the cerium ion coordinated to the imidazolate in an eta-5 mode in addition to two iodide ions and two molecules of THF, see FIG. 25

Example 41

Synthesis of Europium 2-tert-butyl-4,5-di-(1,1-dimethylpropyl)imidazolate iodide bis(tetrahydrofuran)

Figure 26:
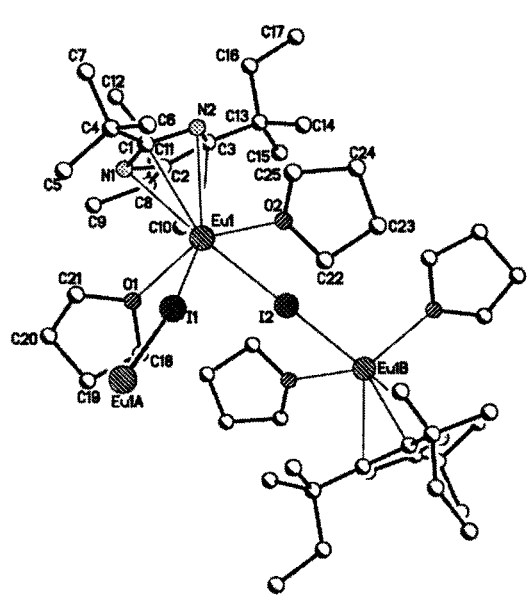
FIG. 26 shows europium (2-tert-butyl-4,5-di-(1,1-dimethylpropyl)imidazolate) iodide bis(tetrahydrofuran), as determined by X-ray crystallography.

Europium II iodide (1.0 g, 0.0025 mol) was stirred in 50 mL of THF for 30 mins at room temperature. Potassium 2-t-butyl-4,5-di-(1,1-dimethylpropyl)-imidazolate (1.51 g, 0.0050 mol) was added, and the resulting mixture was refluxed for 41 hours. THF was removed by vacuum, followed by hexane extraction, then filtration. The hexane was removed by vacuum to yield 1.32 g of solid crude product. Sublimation of a sample of this crude product followed by adding excess tetrahydrofuran, evaporating the solvent and then recrystallizing the resulting residue from hexane yielded crystals for X-ray analysis which confirmed the product to be a 1-D polymeric structure where the imidazolates bind eta-5 to the europium ions which are in turn bridged by iodide ions, see FIG. 26.

Example 42

Figure 27:
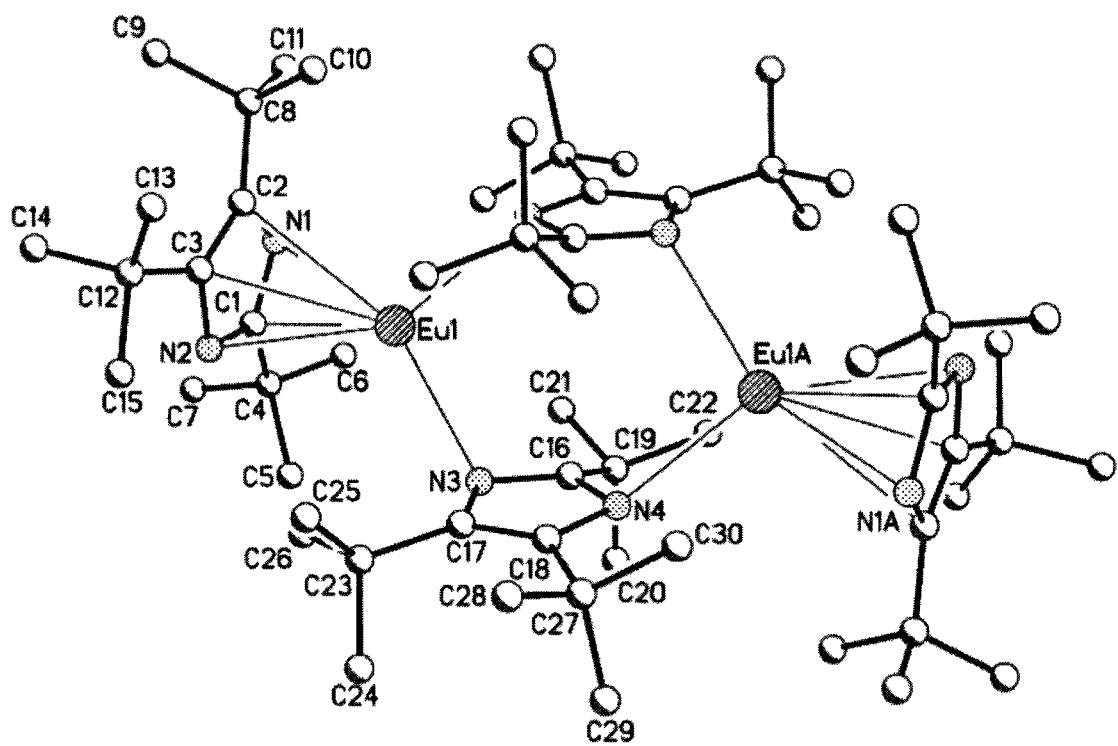
FIG. 27 shows di-europium tetra(2,4,5-tri-tert-butylimidazolate), as determined by X-ray crystallography.

Synthesis of di-Europium tetra-(2-tert-butyl-4,5-di-(1,1-dimethylpropyl)imidazolate Europium II iodide (1.0 g, 0.0025 mol) was stirred in 50 mL of THF for 30 mins at room temperature. Potassium 2,4,5-tri-tert-tbutylimidazolate (1.37 g, 0.0050 mol) was added, and the resulting mixture was refluxed for 60 hours. THF was then removed by vacuum, followed by hexane extraction, then filtration and solvent removal by vacuum. This yielded 0.985 g (79%) of crude product. A sample of this product was then sublimed at 150 C under vacuum to yield a yellow orange solid which was then crystallized in hexane. X ray analysis confirmed the structure of the product as a dimer containing two europium ions and four imidazolate anions. Two imidazolate anions are coordinated to europium in an eta-5 fashion and two imidazolate anions are bridging the metal ions, see FIG. 27.

The invention claimed is:
1. A ruthenium compound represented by Structure A:

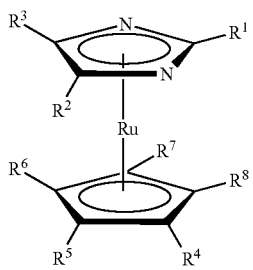

Structure A wherein $R^1$ can be same or different selected from group consisting of linear or branched $C_{1-10}$ alkyls, $C_{1-10}$ alkoxyalkyl, and $C_{1-10}$ aminoalkyl; $R^{2-3}$ are same or different selected from group consisting of hydrogen, methyl, ethyl, n-propyl, iso-propyl, n-butyl, iso-butyl, sec-butyl, tert-butyl, and isomers of pentyl; when $R^2$ is hydrogen, $R^1$ and $R^3$ can not be both C1 alkyl; when $R^3$ is hydrogen, $R^1$ and $R^2$ can not be both C1 alkyl; and $R^{4-8}$ can be same or different selected from group consisting of hydrogen, linear or branched $C_{1-10}$ alkyls, $C_{1-10}$ alkoxyalkyl, and $C_{1-10}$ aminoalkyl.

2. The ruthenium compound of claim 1 wherein $R^1$ is selected from the group consisting of methyl, ethyl, n-propyl, i-propyl, n-butyl, sec-butyl, tert-butyl, tert-amyl; $R^2$ is selected from the group consisting of ethyl, n-propyl, i-propyl, n-butyl, sec-butyl, tert-butyl, tert-amyl.

3. The ruthenium compound of claim 1 wherein $R^4$ is selected from the group consisting of methyl, ethyl, n-propyl, i-propyl, n-butyl, sec-butyl, tert-butyl, tert-amyl; $R^{5-8}$ are hydrogen.

4. The ruthenium compound of claim 1 selected from the group consisting of ruthenium(2,4,5-trimethylimidazolate)(pentamethylcyclopentadienide); ruthenium(2,4,5-trimethylimidazolate)(ethylcyclopentadienide); ruthenium(2,4,5-trimethylimidazolate)(n-propylcyclopentadienide); ruthenium(2,4,5-trimethylimidazolate)(i-propylcyclopentadienide); ruthenium(2,4,5-trimethylimidazolate)(n-butylcyclopentadienide); ruthenium(2,4,5-trimethylimidazolate)(sec-butylcyclopentadienide); ruthenium(2,4,5-trimethylimidazolate)(tert-butylcyclopentadienide); ruthenium(2-ethyl-4-methylimidazolate)(pentamethylcyclopentadienide); ruthenium(2-ethyl-4-methylimidazolate)(methylcyclopentadienide); ruthenium(2-ethyl-4-methylimidazolate)(ethylcyclopentadienide); ruthenium(2-ethyl-4-methylimidazolate)(n-propylcyclopentadienide); ruthenium(2-ethyl-4-methylimidazolate)(i-propylcyclopentadienide); ruthenium(2-ethyl-4-methylimidazolate)(n-butylcyclopentadienide); ruthenium(2-ethyl-4-methylimidazolate)(sec-butylcyclopentadienide); ruthenium(2-ethyl-4-methylimidazolate)(tert-butylcyclopentadienide); ruthenium(2-tert-butyl-4-methyl-5-ethylimidazoate)l(pentamethylcyclopentadienide); ruthenium(2-tert-butyl-4-methyl-5-ethylimidazoate)l(methylcyclopentadienide); ruthenium(2-tert-butyl-4-methyl-5-ethylimidazoate)l(ethylcyclopentadienide); ruthenium(2-tert-butyl-4-methyl-5-ethylimidazoate)l(n-propylcyclopentadienide); ruthenium(2-tert-butyl-4-methyl-5-ethylimidazoate)l(i-propylcyclopentadienide); ruthenium(2-tert-butyl-4-methyl-5-ethylimidazoate)l(n-butylcyclopentadienide); ruthenium(2-tert-butyl-4-methyl-5-ethylimidazoate)l(sec-butylcyclopentadienide); ruthenium(2-tert-butyl-4-methyl-5-ethylimidazoate)l(tert-butylcyclopentadienide); ruthenium(2-tert-butyl-di(1,1-dimethylpropyl)imidazolate)(pentamethylcyclopentadienide); ruthenium(2-tert-butyl-di(1,1-dimethylpropyl)imidazolate)(methylcyclopentadienide); ruthenium(2-tert-butyl-di(1,1-dimethylpropyl)imidazolate)(ethylcyclopentadienide); ruthenium(2-tert-butyl-di(1,1-dimethylpropyl)imidazolate)(n-propylcyclopentadienide); ruthenium(2-tert-butyl-di(1,1-dimethylpropyl)imidazolate)(i-propylcyclopentadienide); ruthenium(2-tert-butyl-di(1,1-dimethylpropyl)imidazolate)(n-butylcyclopentadienide); ruthenium(2-tert-butyl-di(1,1-dimethylpropyl)imidazolate)(sec-butylcyclopentadienide); and ruthenium(2-tert-butyl-di(1,1-dimethylpropyl)imidazolate)(tert-butylcyclopentadienide.

5. A ruthenium compound of the formula represented by Structure B:

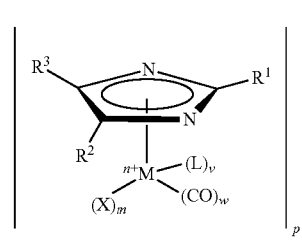

Structure B wherein $R^1$ is selected from group consisting of linear or branched $C_{1-10}$ alkyls, $C_{1-10}$ alkoxyalkyl, $C_{1-10}$ aminoalkyl; $R^{2-3}$ can be same or different selected from group consisting of hydrogen, linear or branched $C_{1-10}$ alkyls, $C_{1-10}$ alkoxyalkyl, $C_{1-10}$ aminoalkyl; (L) is a neutral coordinating ligand selected from ether, polyether, furans, amine, polyamine or alkoxyamine, pyridine, N-methylimidazole, olefin, diolefin, triolefin or polyolefin, alkyne, silylolefin, silyalkyne carbon monoxide, nitrile, isonitrile, silylnitrile or isocyanide, alkyl phosphine, and aromatic phosphine; (v) is 0-4; (X) is a mono anion selected from the group consisting of $C_{1-10}$ alkyls, $C_{1-10}$ alkoxyalkyl, $C_{1-10}$ aminoalkyl, halides; alkoxy, hydride, amide, beta-diketonates, acetates, ketoiminates, diimines, alkoxides, amides, beta-ketoesters, amidinates, guanidinates, cyclopentadienyl, cyanide, isocyanide, pyrrolyl, formate, acetate, cyanate, oxalate, malonate, phenoxide, thiolate, trialkylsiloxide, bis(trialkylsilyl)amide, sulfide, nitrate, alkyl, silylalkyl, fluoroalkyl, aryl, hydride, pyrrolyl, and halide; m=0, 1; (w)=2, 3; p=1, 2.

6. The ruthenium compound of claim 5 wherein $R^1$ is selected from the group consisting of methyl, ethyl, n-propyl, i-propyl, n-butyl, sec-butyl, tert-butyl, tert-amyl; $R^2$ and $R^3$ are selected from the group consisting of hydrogen, methyl, ethyl, n-propyl, i-propyl, n-butyl, sec-butyl, tert-butyl, tert-amyl.

7. The ruthenium compound of claim 5 wherein $R^{1-3}$ are selected from the group consisting of i-propyl, tert-butyl, tert-amyl; m=v=0; w=p=2.

8. The ruthenium compound of claim 5 wherein $R^{1-3}$ are selected from the group consisting of i-propyl, tert-butyl, tert-amyl; m=0; L is selected from the group consisting of Cl, Br, I; w=2, p=1.

9. The ruthenium compound of claim 5 wherein $R^{1-3}$ are selected from the group consisting of i-propyl, tert-butyl, tert-amyl; m=0; L is selected from the group consisting of methyl, ethyl, n-propyl, i-propyl, n-butyl, sec-butyl, tert-butyl, tert-amyl; w=2, p=1.

10. A process where a ruthenium compound of claim 1 is used as a volatile precursor for the deposition of metal containing thin films by a process selected from the group consisting of ALD, CVD, PECVD, pulsed CVD and molecular layer deposition; over a temperature range of 0° C. to 1000° C. and a pressure of 0.1 Torr to 1 atmosphere.

11. A process where a ruthenium compound of claim 5 is used as a volatile precursor for the deposition of metal containing thin films by a process selected from the group consisting of ALD, CVD, PECVD, pulsed CVD and molecular layer deposition; over a temperature range of 0° C. to 1000° C. and a pressure of 0.1 Torr to 1 atmosphere.

12. A process using the ruthenium compounds of claim 1 are used to grow thin metal containing films by spinning a solution of them onto a substrate and then reacting the resulting layer of precursor to give the desired metal containing film.

13. A process using the ruthenium compounds of claim 5 are used to grow thin metal containing films by spinning a solution of them onto a substrate and then reacting the resulting layer of precursor to give the desired metal containing film.

14. A process where a ruthenium compound of claim 1 is used as volatile precursors for the growth of phase change alloys by the processes selected from the group consisting of ALD, CVD, PECVD, pulsed CVD, and Molecular layer Deposition.

15. A process where a ruthenium compound of claim 5 is used as volatile precursors for the growth of phase change alloys by the processes selected from the group consisting of ALD, CVD, PECVD, pulsed CVD, and Molecular layer Deposition.

16. The process of claim 10 wherein these thin films are grown by deposition from a solution of these precursors in a super critical fluid.

17. The process of claim 11 wherein these thin films are grown by deposition from a solution of these precursors in a super critical fluid.

18. The process of claim 16 wherein the super critical fluid is carbon dioxide.

19. The process of claim 17 wherein the super critical fluid is carbon dioxide.

20. A process using a ruthenium compound of claim 1 wherein the process is selected from the group consisting of ALD, CVD, pulsed CVD, PECVD, and molecular layer deposition; using a reactor pressure between 0.001-1000 Torr; a temperature from 0-1000° C.; reacting the metal compound with an oxidant selected from the group consisting of water, alcohol, oxygen, ozone, nitrous oxide, nitrogen dioxide, hydrogen peroxide and combinations thereof, to grow a metal oxide containing film.

21. A process using a ruthenium compound of claim 10 wherein the process is selected from the group consisting of ALD, CVD, pulsed CVD, PECVD, molecular layer deposition; using a reactor pressure between 0.001-1000 Torr; a temperature from 0-1000° C.; reacting with an oxidant selected from the group consisting of water, alcohol, oxygen, ozone, nitrous oxide, nitrogen dioxide, hydrogen peroxide and combinations thereof, to grow a metal oxide containing film.

22. A process using a ruthenium compound of claim 1, wherein the process is selected from the group consisting of ALD, CVD, pulsed CVD, PECVD, and molecular layer deposition; using a reactor pressure between 0.001-1000 Torr; a temperature from 0-1000° C.; by reacting the metal compound with a reagent of nitrogen source molecules selected from the group consisting of ammonia, amines and mixtures thereof.

23. A process using a ruthenium compound of claim 5, wherein the process is selected from the group consisting of ALD, CVD, pulsed CVD, PECVD, molecular layer deposition; using a reactor pressure between 0.001-1000 Torr; a temperature from 0-1000° C.; by reacting the metal compound with a reagent of nitrogen source molecules selected from the group consisting of ammonia, amines and mixtures thereof.

24. A process using a ruthenium compound of claim 1, wherein the process is selected from the group consisting of ALD, CVD, pulsed CVD, PECVD, and molecular layer deposition; using a reactor pressure between 0.001-1000 Torr; a temperature from 0-1000° C.; by reacting the metal compound with a reducing agent selected from the group consisting of hydrogen, ammonia, formic acid, hydrazine, alkyl hydrazine, silane, alkyl silane, disilane, alkyldisilane, trisilane, alkyl trisilane, borane, alkylborane, alane, alkyl alane.

25. A process using a ruthenium compound of claim 5, wherein the process is selected from the group consisting of ALD, CVD, pulsed CVD, PECVD, molecular layer deposition; using a reactor pressure between 0.001-1000 Torr; a temperature from 0-1000° C.; by reacting the metal compound with a reducing agent selected from the group consisting of hydrogen, ammonia, formic acid, hydrazine, silane, alkylsilane, alkyl, alkyldisilane, trisilane, alkyltrisilane, borane, alkylborane, alane, alkyl alane.

26. A method of synthesizing the ruthenium compound of claim 1 by direct metallization of the imidazole ligands using a metal reagent selected from the group consisting of n-butyl lithium, n-hexyl lithium, sec-butyl lithium, tert-butyl lithium, lithium diisopropylamide, potassium hydride, sodium hydride, sodium metal, potassium metal, sodium t-butoxide, and potassium t-butoxide; and then reacting the resulting product with a compound selected from the group consisting of metal iodide, metal acetate, metal carboxylate, metal carbonate, metal formate, metal bromide, metal trifluoroacetate, metal hexafluoroacetylacetone, metal trifluoroacetylacetonate, metal acetyacetonate, metal diimine, metal ketoimine, metal amidinate, metal guanidinate and mixtures thereof.

27. A method of synthesizing the compounds of claim 5 by direct metallization of the imidazole ligands using a metal reagent selected from the group consisting of n-butyl lithium, n-hexyl lithium, sec-butyl lithium, tert-butyl lithium, lithium diisopropylamide, potassium hydride, sodium hydride, sodium metal, potassium metal, sodium t-butoxide, and potassium t-butoxide; and then reacting the resulting product with a compound selected from the group consisting of metal iodide, metal acetate, metal carboxylate, metal carbonate, metal formate, metal bromide, metal trifluoroacetate, metal hexafluoroacetylacetone, metal trifluoroacetylacetonate, metal acetyacetonate, metal diimine, metal ketoimine, metal amidinate, metal guanidinate and mixtures thereof.

28. A method of directly synthesizing compounds of claim 1 by reacting a an alkylated imidazole using a a compound selected from the group consisting of metal amide, metal phenoxide, metal hydroxide, metal alkyl, metal aryl and mixtures thereof.

29. A method of directly synthesizing a ruthenium compound of claim 5 by reacting a polylalkylated imidazole using a compound selected from the group consisting of metal amide, metal phenoxide, metal hydroxide, metal alkyl, metal aryl and mixtures thereof.

30. A method of synthesizing the ruthenium compound of claim 1 by reaction of the imidazole ligand with metal in the presence of ammonia.

31. A process of dissolving a ruthenium compound of claim 1 in a suitable solvent, and injecting a resulting solution into a direct liquid injection system for flash vaporization of the precursor and solvent and delivering a resulting vapor stream into a reactor for the growth of metal containing films by a process selected from the group consisting of; ALD, CVD, pulsed CVD, PECVD and Molecular Layer Deposition.

32. A process of dissolving a ruthenium compound of claim 5 in a suitable solvent, and injecting a resulting solution into a direct liquid injection system for flash vaporization of the precursor and solvent and delivering a resulting vapor stream into a reactor for the growth of metal containing films by a process selected from the group consisting of; ALD, CVD, pulsed CVD, PECVD and Molecular Layer Deposition.

* * * * *